(12) United States Patent
Romero et al.

(10) Patent No.: US 6,331,636 B1
(45) Date of Patent: Dec. 18, 2001

(54) THERAPEUTICALLY USEFUL 2-AMINOTETRALIN DERIVATIVES

(75) Inventors: Arthur G. Romero; William H. Darlington, both of Kalamazoo, MI (US)

(73) Assignee: The Upjohn Company, Kalamazoo, MI (US)

( * ) Notice: Subject to any disclaimer, the term of this patent is extended or adjusted under 35 U.S.C. 154(b) by 0 days.

(21) Appl. No.: 07/850,136

(22) Filed: Mar. 12, 1992

Related U.S. Application Data

(63) Continuation-in-part of application No. PCT/US91/06863, filed on Sep. 26, 1991, which is a continuation of application No. 07/596,923, filed on Oct. 15, 1990, now abandoned, which is a continuation-in-part of application No. 07/360,190, filed on May 31, 1989, now abandoned, application No. 07/850,136, which is a continuation-in-part of application No. 07/768,915, filed as application No. PCT/US90/02726 on May 22, 1990, now abandoned, which is a continuation of application No. 07/360,190, filed on May 31, 1989, now abandoned.

(51) Int. Cl.[7] .................... C07D 263/30; C07D 261/02; C07D 207/30
(52) U.S. Cl. ................. 548/235; 548/247; 548/560; 548/562; 564/428
(58) Field of Search ............ 540/650; 546/205, 546/206; 548/567, 560, 562, 247, 235; 54/105, 70; 514/374, 378, 427, 428, 657; 564/428

(56) References Cited

U.S. PATENT DOCUMENTS

| | | | |
|---|---|---|---|
| 2,352,020 | 6/1944 | Schening | 546/206 |
| 3,933,840 | * 1/1976 | Dahm | 548/235 |
| 4,010,202 | * 3/1977 | Sugihara | 548/235 |

FOREIGN PATENT DOCUMENTS

| | | |
|---|---|---|
| 260 555 | 5/1987 | (EP). |
| 399 982 | 11/1989 | (EP). |
| 2 399 406 | 3/1979 | (FR). |

OTHER PUBLICATIONS

Eisenbraun, E.J., Bansal, R.C., Hertzler, D.V., and Duncan, W.P., Metal–Amine Reactions. The Reductive Amination of Aromtic Hydrocarbons, 1970, The Journal of Organic Chemistry, vol. 35, No. 5, 1265–1271.

Dantchev D.K., Ivanov, I.C., Derivate des 2–Amino–1,2,3, 4–tetrahydronaphthalins, 1974, Archiv Der Pharmazie, D1358E, 596–602.

Chemical Abstract 89759a, Synthesis and potential neuroleptic activity of 2–amino–1–tetralones and 1–tetralols, Eirin, A, et al 1977, vol. 86, p. 539.

Chemical Abstract 189967d, Synthesis of aminotetralins; conformationally restricted analogs of ketamine, Yang, D, et al 1988, vol. 109, p. 670.

* cited by examiner

*Primary Examiner*—Ceila Chang
(74) *Attorney, Agent, or Firm*—Sidney B. Williams, Jr.; Donald L. Corneglio

(57) ABSTRACT

This invention is therapeutically useful 2-aminotetralins and pharmaceutically acceptable acid addition salts thereof of the formula

I

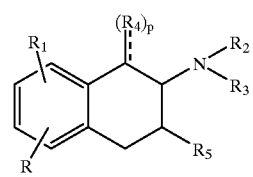

These compounds are useful to treat central nervous system disorders, hypertension, diabetes, sexual impotency and to control appetite.

6 Claims, No Drawings

THERAPEUTICALLY USEFUL 2-AMINOTETRALIN DERIVATIVES

The present application is a continuation-in-part of International Application Serial No. PCT/US91/06863 filed Sep. 26, 1991, now WO 92/06967, which is a continuation of U.S. application Ser. No. 07/596,923, filed Oct. 15, 1990, now abandoned, which is a continuation-in-part of U.S. application Ser. No. 07/360,190 filed May 31, 1989, now abandoned. This case is also a continuation in part of application Ser. No. 07/768,915 filed on Sep. 17, 1991, now abandoned which is the U.S. National case of PCT application Ser. No. PCT/US90/02726, filed May 22, 1990, now abandoned, which in turn was a continuation in part of U.S. application Ser. No. 07/360,190 filed May 31, 1989 now abandoned.

FIELD OF THE INVENTION

The present invention is related to new 1,2,3,4tetrahydro-2-naphthylamines, to processes for preparing such compounds, pharmaceutical preparation of such compounds and the use of such compounds in manufacture of a pharmaceutical preparation.

BACKGROUND OF THE INVENTION

Psychiatric diseases are thought to be due to dysfunctions in monoaminergic neuronal systems, particularly those involving serotonin (5-HT) and dopamine (DA).

Anxiety is associated with increased activity in 5-HT systems. In animals where 5-HT has been depleted, benzodiazepine anxiolytics are not active in anti-anxiety assays that they. otherwise are effective in. Seronotin neurons have autoreceptors that, when activated by agonists, depress firing rates of 5-HT cells. These receptors are of the 5-HT$_{1A}$ subtype. 5-HT$_{1A}$ agonists are anxiolytic. Buspirone is a marketed 5-HT$_{1A}$ agonist that is an anxiolytic. Gepirone is another 5-HT$_{1A}$ agonist with clinically demonstrated anti-anxiety activities.

Depression is a psychiatric condition thought to be associated with decreased 5-HT release. Many anti-depressants potentiate the effects of 5-HT by blocking the termination of activity through reuptake into nerve terminals. 5-HT$_{1A}$ agonists can activate postsynaptically; they thus may also be anti-depressants. Gepirone has already been demonstrated to have ameliorative effects on some depressive endpoints in some patients.

Serotonin is also involved in the regulation of feeding and sexual behavior and in cardiovascular regulation. Thus, 5-HT$_{1A}$ agonists may be useful in treating overeating and sexual dysfunction. These compounds have been shown to alter feeding and sexual behavior in animals. They may also be useful in the treatment of obsessive/compulsive disorders, alcohol abuse and violent behavior. 5-HT$_{1A}$ agonists are also known to depress sympathetic nerve discharge and thus lower blood pressure. Thus, they may be useful in treating hypertension, congestive heart failure (by reducing cardiovascular afterload) and heart attack (be removing sympathetic drive to the heart).

Schizophrenia is thought to be due to hyperactivity in DA systems. Thus, currently available anti-psychotics are DA antagonists. Dopamine autoreceptors depress DA neuron firing rates, DA synthesis and release. Thus DA autoreceptor agonists can also be expected to be anti-psychotics. DA agonists are also useful for treating Parkinsonism, a disease caused by degeneration of DA neurons, and hyperprolactinemia, since DA agonists depress prolactin release.

Dopamine autoreceptor antagonists are a new class of drugs that increase release of DA by releasing the DA neuron from autoreceptor control. Thus, these drugs can be expected to be useful in conditions treatable with amphetamine and other similar stimulants which directly release DA. However, DA autoreceptor agonists will be much milder stimulants because, rather than directly releasing DA, they simply increase the release associated with the normal DA activity by releasing the cell from autoreceptor control. Thus, DA autoreceptor antagonists can be expected to be useful in treating overeating, attention deficit disorders, psychiatric, cognitive and motor retardation in demented and elderly patients, and in treating nausea and dizziness with space travel.

The compounds of the present invention have a variety of effects at 5-HT$_{1A}$ and DA receptors, and offer a variety of utilities associated with those activities.

Clinically, 5-HT$_{1A}$ agonists have also demonstrated anxiolytic properties. The drug, Buspirone, is the only currently available marketed 5-HT$_{1A}$ agonist having anxiolytic activity. This compound antagonizes dopamine receptors at the same dose it stimulates 5-HT$_{1A}$ receptors. A similar drug, Gepirone, also has dopamine antagonist properties. These dopamine antagonist properties reduce the clinical utility of these compounds however because long term treatment with dopamine antagonists can produce tardive dyskinesia.

The search for new CNS active compounds is focused on finding compounds with selective 5-HT$_{1A}$ receptor agonist effects without detrimentally influencing central dopamine receptors.

Drugs acting on central dopamine transmission are clinically effective in treating a variety of central nervous system disorders such as parkinsonism, schizophrenia, and manic-depressive illness. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical anti-psychotic agents directly block the postsynaptic dopamine receptor. The same effect can be achieved by inhibition of intraneuronal presynaptic events essential for the maintenance of adequate neurotransmission, transport mechanism and transmitter synthesis.

In recent years a large body of pharmacological, biochemical and electrophysical evidence has provided considerable support in favor of the existence of a specific population of central autoregulatory dopamine receptors located in the dopaminergic neuron itself These receptors are part of a homeostatic mechanism that modulates nerve impulse flow and transmitter synthesis and regulates the amount of dopamine released from the nerve endings.

Direct dopamine redeptor agonists, like apomorphine, are able to activate the dopamine autoreceptors as well as the post synaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The anti-psychotic and anti-dyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

The following documents could be important in the examination of this application.

Arvidsson, L.-E., et al., J. Med. Chem., 24, 921 (1981), describes hydroxy-2-aminotetralins where the amine is substituted with one n-propyl, one benzyl or two n-propyl substituents. The 5-, 6-, and 7-hydroxy compounds are described as active central dopamine-receptor agonists and the 8-hydroxy compound is described as a central 5-HT receptor agonist devoid of dopamine receptor stimulating activity.

Arvidsson, L.-E., et al., J. Med. Chem., 27, 45 (1984), describes 2-aminotetralins where the amine is substituted with one or two methyl, ethyl, n-propyl, i-propyl, n-butyl, or benzyl substituents. The 2-piperidinyltetralin is also described. Several of these compounds were found to be potent 5-HT agonists devoid of dopamine-mimetic effects.

Arvidsson, L.-E., et al., J. Med. Chem., 30, 2105 (1987), describes 8-hydroxy-1-methyl-2-(di-n-propylamino) tetralins. These compounds were 5-HT receptor agonists.

The Arvidsson, L.-E. et al 8-hydroxy and 8-methoxy tetralin compounds are also disclosed in Derwent documents 00389J/47, 94981D/51 and 045535J.48.

McDermed, et al., J. Med. Chem., 18, 362 (1975) describes 5,6 dihydroxy-2-aminotetralins. In addition, the 5,8 and 7,8 disubstituted compounds are also disclosed. The amine can be a mono or di substituted with simple alkyl groups, benzyl groups alkylalkoxy groups or the amine can be a 5 or 6 membered hydrocarbon or heterocyclic amine. These compounds are indicated to have dopaminergic properties although certain compounds are reported to be inactive.

McDermed, et al., J. Med. Chem., 19, 547 (1976) describes 5-, 6-, or 7-hydroxy-2-dipropylaminotetralins. These compounds are described as dopaminergic compounds.

Rusterholz, et al., J. Med. Chem., 19, 99 (1976) describes 5,8 disubstituted-2-aminotetralins with the amine being substituted with hydrogen, methyl, or cyanopropyl groups. Some of these compounds are potent prolactin inhibitors and believed to be dopamine agonists.

Ames, et al., J. Chem. Soc, 2636 (1965) describes the preparation of a large number of compounds, where the aromatic ring is substituted by methoxy, ethoxy, n- or iso-propoxy, or n-, sec- or tert-butoxy group in the 5 or 8 position and the amine is substituted by hydrogen or alkyl groups having 1–4 carbon atoms. The compounds are indicated to be prepared for pharmacological testing. However, no utility or pharmacological activity is yet known for the compounds just mentioned.

EPO Application No. 89304935.3 discloses 2-amino 1,2,3,4-tetrahydronaphthalenes as selective inhibitors of serotonin reuptake. It has a publication date subsequent to filing date of the parent application of this case.

German Patent DE 2 803 582 describes 2-aminotetralins where the aromatic ring is substituted on the 5,6,7 or 8 position with the group $R_1$, where $R_1$ is hydrogen, alkanoyl having 1 to 20 carbon atoms or a group —CO—$(CH_2)_n$—$R_7$, n is a number 0 to 5, $R_7$ is a phenyl group with substituents as defined further, $R_2$ is hydrogen, hydroxy, halogen or alkylsulfonylamino, $R_3$ is hydrogen, $R_4$ is hydrogen, $CH_2OH$, $CH_2O$—CO—$R_8$ or $CH_2$—O—CO—$(CH_2)_n$—$R_7$ with further definition and $R_5$ and $R_6$ are hydrogen, alkyl or aryl or aralkyl groups further defined or $R_5$ and $R_6$ are together an alkylene with 4 to 6 carbon atoms. The compounds are disclosed as having pharmacodynamic activity in particular a stimulating effect on alpha- and beta-adrenoceptors and dopamine receptors. Among the compounds described are compounds having the group $R_{10}$ in the 8 position and having $R_2$ or $R_4$ other than hydrogen.

Great Britain Patent 1,377,356 describes 2-aminotetralins where the aromatic ring is substituted on the 5, 6,7 or 8 position by $R_1$, where $R_1$ is hydrogen or methyl, the aliphatic ring is substituted by $R_2$, where $R_2$ is alkyl having 1–6 carbon atoms, and the amine is substituted by $R_3$, where $R_3$ is hydrogen or alkyl having 1–6 carbon atoms are described. Such compounds are stated to possess analgesic activity. 1,1-Dimethyl-2-(N,N-dimethylamino)-7-hydroxytetralin is mentioned as one example of a compound covered by the patent. This compound is also described in Chem. Ab., 79: 146294b as having analgesic and intestinal movement accelerating actions.

J. Pharm. Sci., 67, 880–82 (1978) describes the compound 1-methyl-2-(cyclopropylamino)-5-methoxytetralin and indicates the compound possess local anesthetic activity.

Derwent documents 58,247B/32, 40 378A/23, 83-729388/32, 83-72987/32, 29348D/17 and 06733V/05 refer to 8mboxyamino tetralins. Additional 07833V/05 refers to 8-amido and 8-alkylamido tetralin.

EPO patent application EPO 270 947 (1988) discloses 8-hydroxy and 8-methoxy-tetralins.

EPO patent application EPO 272 534 (1988) discloses aminotetralins including 8-amido compounds.

The references cited herein are disclosures describing work related to the invention:

Hjorth, S.; Carlsson, A; Lindberg, P.; Sanchez, D.; Wikstrom, H.; Arvidsson, L.-E.; Hacksell, U.; Nilsson, J. L. G., *J. Neural Transm.,* 1982, 55, page 169.

Mellin, C.; Bjork, L.; Karlen, A.; Johansson, A. M.; Sundell, S.; Kenne, L.; Nelson, D. L.; Anden, N.-E.; Hacksell, U., *J. Med. Chem.,* 1988, 31, page 1130.

Cossery, J. M.; Gozlan, H.; Spampinato, U.; Perdicakis, C.; Guillaumet, G.: Pichat, L.; Hamon, M., European *J. Pharmacol.,* 1987, pages 140–143.

SUMMARY OF THE INVENTIfON

A compound having the formula I

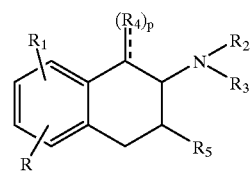

wherein R is hydrogen or halogen,
  wherein $R_1$ is
    (a) -hydrogen,
    (b) —$OR_6$,
    (c) —$SR_6$,
    (d) —$CONR_7R_8$,
    (e) —CN,
    (f) -het,
    (g) —C(O)het,
    (h) —$CF_3$,
    (i) —$SO_2NR_7R_8$,
    (j) -5-oxazolyl
    (k) —$CSNR_5R_6$
    (l) —$OSO_2CF_3$
  wherein $R_2$ and $R_3$ are independently
    (a) -hydrogen,
    (b) —$(C_1-C_8)$ alkyl,
    (c) —$(C_2-C_8)$ alkenyl,
    (d) —$(C_2-C_8)$ alkynyl, (e) —$(CH_2)_m$—$(C_3$-$C_8)$cycloalkyl,
(f) —$(CH_2)_m$—$(C_3$-$C_8)$cycloalkenyl,
(g) —$(CH_2)_m$-aryl,
(h) $R_2$ and $R_3$ taken together with the nitrogen atom are
   —N X wherein $R_4$ and $R_5$ are independently
   (a) -hydrogen,
   (b) —$(C_1$-$C_8)$alkyl,
   (c) —$(C_2$-$C_8)$alkenyl,
   (d) —$(C_2$-$C_8)$alkynyl,
   (e) —$(CH_2$—$)_m$—$(c_3$-$C_8)$cycloalkyl,
   (f) —$(CH_2)_m$—$(C_3$-$C_8)$cycloalkenyl,
   (g) —$(CH_2)_m$-aryl,
   (h) —$(CH_2)_m$—$CO_2R_6$,
   (i) —$(CH_2)_m$—$OR_6$, wherein $R_6$, $R_7$ and $R_8$ are independendy
   (a) -hydrogen,
   (b) —$(C_1$-$C_4)$alkyl,
   (c) —$(C_1$-$C_4)$alkenyl,
   (d) —$(C_3$-$C_8)$cycloalkyl wherein X is
   (a) —$(CR_6R_6)_n$—,
   (b) —$(CR_6R_6)_r$-alkenyl-$(CR_6R_6)_q$—,
   (c) —$(CR_6R_6)_r$—O—$(CR_6R_6)_q$—,
   (d) —$(CR_6R_6)_r$—S—$(CR_6R_6)_q$—,
   (e) —$(CR_6R_6)_r$—$NR_6(CR_6R_6)_q$—, wherein $R_9$ is
   (a) -hydrogen,
   (b) —$OR_6$,
   (c) —$SR_6$, wherein $R_{10}$ is
   (a) -hydrogen,
   (b) —$(C_1$-$C_4)$akyl,
   (c) -aryl,
   (d) —$(C_1$-$C_4)$alkyl
   (e) —C(O)alkyl,
   (f) —C(O)aryl wherein Y is hydrogen or halogen
   m is 0–4,
   n is 4–8,
   p is 0–1,
   q is 2–4,
   r is 2–4 with the provisos that when $R_1$ is hydroxy or methoxy and $R_4$ is hydrogen both $R_2$ and $R_3$ cannot be hydrogen, same alkyl, or cyclo-propylmethyl and that

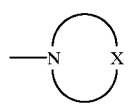

cannot be piperidino, piperazino or homopiperazino; that when $R_1$ is 8—$CONH_2$ or 8—CN, $R_2$ and $R_3$ cannot both be propyl; and that when $R_1$, $R_4$ and $R_5$ are hydrogen and either $R_2$ or $R_3$ is hydrogen, the other cannot be ethenyl.

Also provided are compounds having the formula

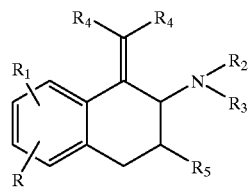

II wherein $R_1$, $R_2$, $R_3$ and $R_4$ are the same as above.

Selected compounds of this invention possess selective pharmacological properties and are useful in treating central nervous system disorders including anti-depression symptoms, anti-psychotic symptoms, anxiolytic symptoms, panic attacks, obsessive-compulsive disturbances, senile dementia, emotional disturbances related to dementia disorders, and stimulation of sexual activity. Selected compounds of this invention are also useful to alleviate aggressive behavior, confusional delirious states and impotence. Selected compounds of this invention are further useful as anti-diabetic, anti-obesity, anti-hypertensive agents and for treating sexual impotency.

Processes for preparation of these compounds, their pharmaceutical use and pharmaceutical preparations employing such compounds constitute further aspects of the invention.

An object of the invention is to provide compounds for therapeutic use, especially compounds having a therapeutic activity in the central nervous system. Another object is to provide compounds having an effect on the 5-$HT_{11A}$ receptor in mammals including man. A further object of this invention is to provide pounds having an effect on the subclass of dopamine receptors known as the $D_2$ receptor.

DETAILED DESCRIPTION OF THE INVENTION

The compounds of this invention are identified in two ways: by the descriptive name and reference to labelled structures contained in appropriate charts. In appropriate situations, the proper stereochemistry is also represented in the charts.

In this document the parenthetical term ($C_n$-$C_m$) is inclusive such that a compound of ($C_1$-$C_8$) would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl.

Alkoxy as represented by —$OR_1$ when $R_1$ is ($C_1$-$C_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, isohexoxy, n-heptoxy, isoheptoxy, and n-octoxy.

Alkenyl refers to a radical of an aliphatic unsaturated hydrocarbon having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4hexenyl, 1-methyl-4-hexenyl, 3-methyl-1-hexenyl, 3-methyl-2- hexenyl, 1-heptenyl, 2-heptenyl, 3-heptenyl, 4heptenyl, 1-methyl-4-heptenyl, 3-methyl-1-heptenyl, 3-methyl-2-heptenyl, 1-octenyl, 2-octenyl, or 3-octenyl.

Cycloalkyl refers to a radical of a saturated cyclic hydrocarbon such as cyclopropyl, cyclobutyl, cyclopentyl, cyclohexyl, cycloheptyl, or cyclooctyl.

Het refers to a five atom heterocyclic ring containing nitrogen, carbon and in some cases oxygen. It includes 2-pyrrolyl, 2-oxazolyl, 2-imidazolyl, 2-oxazolinyl, 2-imidazolinyl.

Halogen refers to bromine, chlorine or fluorine.

6Phenyl-4H-5-triazolo[4,3-a][1,4]benzodiazepinyl refers to residues of the benzodiazepines described in U.S. Pat. No. 3,987,052. It includes the residues of alprazolam and triazolam CNS compounds known in the art.

It will be apparent to those skilled in the art that compounds of this invention do contain chiral centers. The scope of this invention includes all enantiomeric or diastereomeric forms of Formula I compounds either in pure form or as mixtures of enantiomers or diastereomers. The compounds of Formula I contain 1–3 asymmetric carbon atoms in the aliphatic ring moiety, including the ring carbon atoms adjacent to the nitrogen atom. The therapeutic properties of the compounds may to a greater or lesser degree depend on the stereochemistry of a particular compound. Pure enantiomers as well as enantiomeric or diastereomeric mixtures are within the scope of the invention.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and outlined in the appropriate charts.

Compounds of the invention wherein $R_1$ is alkyl amido or dialkyl amido and $R_2$ and $R_3$ are hydrogen or alkyl can be made by the process illustrated in Chart A.

Chart A

In step 1 of Chart A, substituted 2-tetralone A-1 is treated with ethylene glycol in the presence of p-toluenesulfonic acid and a solvent such as benzene at a reflux temperature for about one to eight hours to yield A-2. The starting substituted tetralones, for example, 8-methoxy-tetralone, are readily available or can be prepared by methods well known in the art.

In Step 2, A-2 is converted to the corresponding hydroxy compound A-3 by refluxing in a reaction mixture of diphenyl- phosphine and n-butyllithium.

In Step 3, A-3 is reacted with trifluoromethanesulfonic anhydride in the presence of methylene chloride and pyridine to provide A-4 tetralin.

In Step 4 carbon monoxide is bubbled through a mixture of A-4, palladium acetate, bis(diphenylphosphino)propane, diisopropylethylamine, methanol and dimethyl sulfoxide to yield A-5.

In Step 5, A-5 is hydrolyzed with a base such as potassium hydroxide to yield A-6.

In Step 6, A-6 and carbonyldiimidazole is dissolved in a solvent, such as THF and the resulting solution reacted with ammonia saturated THF to yield A-7.

In Step 7, A-7 is dissolved in a solvent, such as acetic acid, and heated to yield A-8.

In Step 8, A-8 is reacted with the appropriate amine in the presence of sodium cyanoborohydride, methanol and acetic acid to yield the 2-N-alkylamino compound A-9.

In Step 9, A-9 is refluxed with n-haloalkane in the presence of sodium carbonate and acetonitrile to yield the 2-N,N-dialkylamino compound A-10.

Chart B

In addition compounds of A-5 (B-1) can be converted to compounds of Formula I wherein $R_1$ is arylcarbonyl by the process illustrated in Chart B. In Step 1 a solution of B-1(A-5) is reacted with the pyrrole-adduct in a solvent such as toluene in the presence of ethylmagnesium bromide to yield B-2.

In Step 2, B-2 is reacted with an N-alkylamine in the presence of acetic acid, platinum oxide and absolute ethanol under a hydrogen atmosphere to yield N-alkylamino compound B-3. Compounds wherein

is

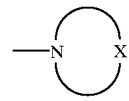

can be prepared by substituting a heterocyclic amine for the N-alkylamine in this step.

In Step 3, N,N-dialkylamino compound B-4 is prepared by reacting B-3 with an n-haloalkane in the presence of a base such as sodium carbonate and a solvent such as acetonitrile.

Methods for preparing compounds of Formula I wherein $R_1$ is hydrogen, $—OR_6$, or $—SR_6$ are illustrated by the processes illustrated in Charts C to F. In each of these processes, 2-tetralone derivatives are utilized as the starting material.

Chart C

In step 1 substituted 2-tetralone C-1, wherein $R_1$, $R_2$ and $R_3$ are defined as above, is subjected to reductive amination whose procedures are known in the art to yield C-3.

In step 2 an aqueous solution of C-2 wherein $R_1$ is methoxy is heated with an acid, for example hydrobromic acid to provide C-3.

Chart D

In step 1 substituted 2-tetralone D-1 is converted to substituted aminotetralin D-2 by reductive amination. In step 2, D-2 is converted to 2-aminotetralin, D-3, which is converted in Step 3 to D-4, a N-substituted aminotetralin via reductive amination.

Chart E

In step 1, substituted 2-tetralone E-1 is alkylated at the 2-position to produce E-2 by reaction with an alkyl halide utilizing base in accordance with alkylation methods well known in the art. In step 2, E-2 is subjected to reductive amination to produce E-3.

Chart F

In step 1, substituted tetralone F-1 is reacted with dimethylcarbonate in the presence of base such as LDA to produce F-2. In step 2 F-2 is reacted with alkyl halide in the presence of base to produce F-3. In step 3, F-3 is decarboxylated to produce F-4. In step 4, F-4 is subjected to reductive amination to produce F-5. In step 5, an aqueous solution of F-5 wherein $R_1$ is methoxy is heated with an acid, for example hydrobromic acid, to provide F-6.

Chart G

In step 1, substituted tetralone G-1 (F-2) is reductively aminated by procedure known in the art. G-2 is alkylated to form amide G-3 by reaction with propionic anhydride in pyridene. In step 3, G-3 is reduced in the presence of reducing agent such as LAH to produce G-4. G-4 is converted to G-5 in step 4 by tosylation then elimination with the appropriate base via methods well known in the art.

Chart H

In step 1, 2-bromophenylacetylchloride is substituted in the procedure detailed in A. H. Horn, C. J. Grol, D. Dijkstra and A. H. Mulder, J. Med. Chem. 11, 285 (1978) to yield H-2. In step 2, H-2 is reacted with ethylene glycol to yield H-3. In step 3, H-3 is reacted with sodium trifluoroacetate to provide H-4. In step 4, H-4 is heated in the presence of tetrahydrofuran to yield H-5. In step 5, H-5 is reacted with R-(+)-alpha-methylbenzylamine and acetic acid to provide H-6. In step 6, H-6 is reacted with sodium cyanaborahydride to provide diastereomers of H-7. In step 7, both diastereomer of H-7 are separately refluxed with borone dimethylsulfide complex to yield diastereomer of H-8. In step 8, diastereomer H-8 is subjected to hydrogenolysis to yield H-9 which in turn is N-alkylated in step 9 to yield H-10.

Chart I

In step 1, bromotetralone I-1 is reductively aminated using typical conditions with the appropriate amine to obtain I-2. In step 2, I-2 is treated with t-butyllithium followed by dimethylformamide to obtain aldehyde I-3. This aldehyde is condensed in step 3 with "TOSMIC" under typical conditions to obtain the oxazole I-4.

Chart J

In step 1, substrate J-1 is treated with t-butyllithium followed by sulfur dioxide to obtain sulfonic acid J-2. In step 2, J-2 is treated with sodium hydride to obtain J-3 followed by treatment with N-chlorosuccinimide in step 3 to obtain sulfonylchloride J-4. Treatment of J-4 with ammonia in step 4 gives J-5 which is hydrolysized with aqueous acid to J-6 in step 5. In step 6, reductive amination using typical conditions using the appropriate amine gives J-7.

Chart K

Bromo compound K-1 is treated with t-butyllithium followed by trimethylsilylisothiocyanate to give K-2.

Chart L

In step 1 of Chart L, the phenol L-1 is reacted with trifluoromethanesulfonic anhydride in the presence of a solvent according to methods well known in the art to yield the triflate L-2. The phenol L-1 can be prepared from the appropriately substituted tetralones by the process depicted in Chart C.

In step 2, a solution of L-2 in a solvent mixture such as methanol/DMF is reacted with carbon monoxide gas, palladium acetate, triethylamine and 1,3-bis (diphenylphosphino) propane to form the carboxylic acid methyl ester L-3.

In step 3, the methyl ester L-3 is hydrolyzed with sodium hydroxide in methanol.

The resulting acid L-4 then coupled in step 4 with ammonia in the presence of diethylcyanophosphonate and triethylamine in a solvent such as DMF to yield the carboxamide L-5.

Chart M

In step 1, acid chloride M-1 is treated with ethylene in the presence of aluminum trichloride to obtain tetralone M-2. M-2 is reductively aminated with the appropriate amine to yield M-3. M-3 is then dissolved in a solvent such as THF and reacted in the presence of t-butyllithium and trimethylsilyl isocyanate to yield amide M-4.

Chart N

In step 1, ketal N-2 is generated by stirring tetralone N-1 with ethylene glycol in the presence of an acid catalyst. In step 2, the 8-trifluoromethyl compound N-3 is easily obtained by heating a mixture of N-2, copper(I) iodide, sodium trifluoroacetate and N-methylpyrrolodone to 160° C. In step 3, hydrolysis using aqueous acid gives tetralone N-4 which is reductively aminated in step 4 using the known procedure of mixing the appropriate amine acetic acid, and sodium cyanoborohydride to yield N-5.

Methods for conducting reductive amination are well known in the art and any such methods may be used in the procedures described above. One such method involves reacting the tetralone with an amine in the presence of sodium cyanoborohydride and glacial acetic acid in tetrahydrofuran/methanol.

The 8-amido compounds of A-10 can be converted to the corresponding 8-cyano compounds by reacting A-10 with a "Burgess salt" utilizing conditions well known in the art. The Burgess salt can be prepared by the procedure described in *Organic Synthesis*, 56, page 40.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutical treatment the suitable daily doses of the compounds of the invention are 1–2000 mg for oral application, preferentially 50–500 mg, and 0.1–100 mg for parenteral application, preferentially 0.5–50 mg.

The compounds of this invention where $R_1$ is in the 8 position in the aromatic ring are very selective $5\text{-HT}_{1A}$ receptor agonists having little or no dopaminergic activity. The $IC_{50}$ ratio of dopamine $D_2$ to $5\text{-HT}_{1A}$ in vitro binding data shown in Table 1 for one compound of this invention, demonstrates the selectivity for the $5\text{-HT}_{1A}$ receptor. The compounds of this invention also have been shown to have high oral potency and a long duration of action. Both these features are beneficial to effective clinical treatment.

The utility of the compounds of this invention to treat central nervous system disorders is shown in behavioral, physiological and biochemical tests. The methods are given as follows:

Binding

Inhibition of 8OH-DPAT binding in a bovine brain homogenate. Potency is given as nM dose required to inhibit 50% of DPAT binding ($IC_{50}$). This test measures ability to bind to 5-hydroxytryptamine ($5\text{-HT}_{1A}$) receptor.

Hypothermia

Starting with a dose of 30 mg/kg, four mice are injected subcutaneously with test compound. Twenty minutes later, the number of animals whose body temperature has decreased by 2° C. or more are counted. If all four animals reach criteria, the drug is considered "active", and subsequent readings are taken at 60 and 120 minutes after drug. The time for last statistically significant drug affect on mean body temperature is indicated in minutes. For all "active" compounds, doses are lowered by 0.5 log intervals until a dose which does not lower body temperature by 2° C. in any animal is found. Potency is given as mg/kg ED50 (dose required to depress temperature in two of four mice) as measured by Spearman-Karber statistics.

Sympathetic Nerve Discharge (SND)

The i.v. mg/kg dose causing a 50% depression in SND in chloralose anesthetized cats and the maximum inhibition of sympathetic activity observed in the dose range tested (0.001–1.0 mg/kg i.v.).

BP SND/MAX

The blood pressure of the chloralose anesthetized cats in percent control at the dose causing 50% depression in SND and the maximum reduction in blood pressure as percent of the control blood pressure in the same animals observed in the dose range tested (0.001–1.0 mg/kg i.v.).

TABLE I

CNS BIOLOGICAL DATA

| Example No | Compound No | 5-HT$_{1A}$ Binding IC$_{50}$ (nM) | Hypothermia ED$_{50}$ (mg/kg) |
|---|---|---|---|
| 5 | 2 | 13 | 0.31 |
| 15 | 12 | 7.9 | 1.2 |
| 15 | 27 | 8.9 | 0.31 |
| 19 | 2 | 3.5 | 0.73 |
| 21 | 6 | 50.7 | 0.97 |
| 26 | 1 | 3.7 | 2.31 |
| 57 | 57-3 | 103.4 | 2.3 |
| 58 | 58-1 | 26 (>1000 Ic$_{50}$ (nm at D$_2$ receptor) | 2.3 |
| 59 | 59-1 | 4 | |
| 60 | 60-1 | 10.9 | |

TABLE II

ANTI-HYPERTENSIVE BIOLOGICAL DATA

| | | | Serotonin SND Assay | | |
|---|---|---|---|---|---|
| Example No. | Compound No. | SND ED$_{50}$ | Max. Decr. SND % Control | % BD (at SND ED$_{50}$) | Max Dec. BP |
| 5 | 2 | 0.33 | 1.5 | 40.0 | 40.0 |
| 15 | 12 | 0.012 | 0.0 | 79.0 | 37.0 |
| 15 | 27 | 0.1 | 0.0 | 62.0 | 28.0 |
| 19 | 2 | 0.01 | 0.0 | 78.0 | 38.0 |
| 21 | 6 | 0.6 | 5.0 | 52.0 | 53.0 |
| 26 | 1 | 0.16 | 18.0 | 70.0 | 58.0 |
| 57 | 57-3 | 0.62 | 31.0 | 75.0 | 68.7 |
| 58 | 58-1 | >. | 296 | — | 71.0 |

The compounds of this invention are useful as anti-diabetic and anti-obesity agents. While all of the compounds do not have all of these pharmacological activities the utility of a particular compound can be determined by one skilled in the art utilizing the following tests.

Anti-diabetic

A. Testing For Blood Glucose Lowering in the KKA$^y$ Mouse

All KKA$^y$ mice used for screening are produced and selected by methods outlined by T. Fujita et al., Diabetes, 32, pp. 804–10 (1983). The screening is done in groups of six animals per group.

Pre-treatment non-fasting blood glucose (NFBG) samples are measured five days prior to the start of a screening run by previously described methodologies. These blood sugar values are used to place animals into groups with equal mean blood glucose concentrations and to eliminate any mice with a NFBG value <250 mg/dl. On day 0, compounds chosen to be run are incorporated into ground mouse chow (Purina 5015). Compounds are included at a rate of 1 mg/gram of chow. Generally, 300 g of drugs containing diet is prepared for each group. Mice receiving ground chow only are the negative control.

Each screening run also uses ciglitazone (T. Fujita et al., supra) as a positive control (0.5 to 1.0 mg/gram chow).

Initial body and food weights are taken on day one. Food is placed in a crock which contains an adequate amount to last for the length of the study. In order to acclimate the mice from pelleted mouse chow to ground mouse chow, they are fed the ground chow for nine days prior to use in the screen. On day four of treatment, a NFBG sample is again measured, as well as food and body weights. Food consumption measurements are used to determine an average mg/kg dose the mice received over the testing period, and to evaluate the compound's effect on food consumption.

Acceptance and Activity Are Determined by the Following Criteria

A. Negative Control

This group must not show a significant change (p<0.05) from pre- to post-treatment. If there is a significant decrease in blood sugar, the run is not valid.

B. Positive Control

This group must show a significant depression in blood sugar mean levels from pre- to post-treatment. A lack of activity in this group would also invalidate the run.

C. Negative Control vs. Positive Control

This contrast must be significant. It is a further assurance that both control groups performed as expected.

D. Compound

A compound's activity is based on several criteria:

1. A significant decrease in blood sugar mean levels from pre- to post-treatment.

2. Negative control vs. compound: This contrast allows one to determine if these groups are dissimilar, which is required for the compound to be considered active.

II. Anti-obesity Activity

Upjohn Sprague-Dawley rats are housed individually and given food and water ad libitum. Food consumption is measured daily. The animals are orally dosed with 100 mg/kg or 200 mg/kg of the compound in Tween 80. Controls receive an equivalent volume of (0.25) of Tween 80. If the daily food consumption of the treated animals is in the range of 4 grams less than that of the control animals the compound is considered to have anorexic activity.

EXPERIMENTAL PROCEDURES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

8-Methoxy-2-[spiro-2-(1,3-dioxolyl)tetralin (A-2, Chart A)

Into a round bottom flask was placed 8-methoxy-2-tetralone (50 g, 284 mmol), ethylene glycol (35.2 g, 2 eq.), p-toluenesulfonic acid (80 mg) and benzene (600 ml.). The solution was refluxed for seven hours, removing water as it was generated with a Dean-Stark trap. The solution was cooled and poured into saturated aqueous sodium carbonate. Ether (500 ml) was added and the solutions were extracted.

The organic layer was washed with water (300 ml) and brine (300 ml). The aqueous layers were back extracted with ether (500 ml). The organic layers were combined and dried over anhydrous sodium sulfate and the solvent removed in vacuo to afford 56 g of the title compound (90% yield).

PREPARATION 2
8-Hydroxy-2-[spiro-2-(1,3dioxolyl)]tetralin (A3, Chart A)

To a 0° solution of diphenylphosphine (30.65 ml, 176 mmol) in THF (300 ml) was added n-butyllithium (170 mmol). The resulting red anion was stirred 30 minutes, then a solution of 8-methoxy-2-[spiro-(1,3dioxolyol)]tetralin (25 g, 113.6 mmol) dissolved in THF (100 ml. was added. The solution was heated to reflux for 24 hours, then cooled in an ice bath and saturated aqueous ammonium chloride added. Ether (800 ml) was added and the solutions were extracted. The organic layer was washed with saturated aqueous sodium bicarbonate (200 ml) followed by brine (400 ml) and dried over anhydrous sodium sulfate. The solvent was removed in vacuo and the residue placed on a flash silica gel column (6 cm×40 cm) and eluted with ethyl acetate/hexane (5:95, switching to 30:70 to elute off product). Solvent removal in vacuo afforded 21.2 g of a white solid (102.9 mmol, 90% yield).

PREPARATION 3
8-Trifluoromethanesulfonyl-2-[spiro-2-(1,3-dioxoyl)]tetralin (A-4, Chart A)

To a 0° C. solution of 8-hydroxy-2-[spiro-2-(1,3dioxolyl)]tetralin (52.2 g, 253 mmol) dissolved in methylene chloride (400 ml) and pyridine (200 ml) was added trifluoromethane-sulfonic anhydride (93 ml, 329 mmol). The solution was allowed to sit at 5° for 15 hours, then quenched by pouring into cold saturated aqueous sodium carbonate solution. Ether (80 ml) was added and the solution extracted. The organic layer was washed with brine (400 ml) and dried over anhydrous sodium sulfate, the solvent being removed in vacuo. The residue was placed on a flash silica gel column (6 cm×40 cm) and eluted with ether/hexane (2:98, changing to 7:93). Solvent removal in vacuo afforded 64.5 g of the title compound.

PREPARATION 4
8-Carbomethoxy-2-[spiro-2-(1,3dioxolyl)]tetralin (A-5, Chart A)

8-Trifluoromethylsulfonyl-2-[spiro-2-(1,3-dioxolyl)]tetralin (62 g, 183.4 mmol) was placed in a round bottom flask with palladium acetate (2.88 g, 7 mol %), bis(diphenylphosphino)propane (6.81 g, 9 mol %), diisopropylamine (70.3 ml, 2.2 eq.), methanol (183 ml) and dimethylsulfoxide (550 ml). The flask was thoroughly flushed with carbon monoxide, which was subsequently bubbled through the solution. The solution was heated to 70° and stirred for four hours. The solution was cooled and 400 ml. of methylene chloride and 800 ml of ether added. This solution was washed with water (4×500 ml) and brine (400 ml), and dried over anhydrous sodium sulfate. Solvent removal in vacuo and filtration through a plug of flash silica gel (6 cm×30 cm) with ethyl acetate/hexane (25:75), followed by solvent removal afforded 39 g of the title compound (85% yield) as an oil.

PREPARATION 5
1,2,3,4-Tetrahydrospiro[2-(1,3-dioxolane)-2-naphtha-lene-8-yl-carboxylic Acid (A-6, Chart A)

Methyl 1,2,3,4-tetrahydrospiro[2-(1,3dioxolane)-2-naphthalene]-8-yl-carboxylate (25 g, 101 mmol) and potassium hydroxide (28.2 g, 5 eq.) were dissolved in a solution of water (50 ml) and methanol (150 ml). This solution was heated to reflux for two hours. The solution was cooled and most of the solvent removed in vacuo. The residue was dissolved in water (300 ml) and extracted with ether (2×200 ml). The aqueous solution was cooled in an ice bath and acidified with concentrated hydrochloric acid to pH 2. The aqueous solution was quickly extracted with ether (2×600 ml). Combined the organic layers and washed with brine (2×300 ml), dried over anhydrous sodium sulfate and the solvent removed in vacuo to afford 21.5 g (91% yield) of the carboxylic acid as a white solid (m.p. 142° C.).

PREPARATION 6
1,2,3,4-Tetrahydrospiro[2-(1,3dioxolane)-2-naphtha-lene-8-yl-carboxamide (A-7, Chart A)

1,2,3,4-Tetrahydrospiro[2-(1,3-dioxolane)-2-naphthalene]-8-yl-carboxylic acid (12.34 g, 56.6 mmol and carbonyldiimidazole (11.0 g, 1.2 eq.) were dissolved in THF (100 ml) and stirred for six hours. While cooling to 0°, a solution of THF (40 ml) saturated at 0° with ammonia was added. The reaction was capped to contain the ammonia and warmed to 25° and stirred for five hours. Methylene chloride (200 ml) and ether (200 ml) were added and the solution was poured into water (500 ml) and extracted. The organic layer was washed with 2 N aqueous hydrochloric acid (300 ml), water (300 ml), saturated aqueous sodium bicarbonate (300 ml), brine (300 ml) and dried over anhydrous sodium sulfate. Solvent removal in vacuo afforded 7.88 g of the title compound (60% yield) as a white solid.

Utilizing a process similar to that of Preparation 6, but substitutes the appropriate amine for ammonia, there is obtained the corresponding N-alkylcarboxamide aminote-tralins.

PREPARATION 7
1,2,3,4-Tetrahydro-2-oxo-naphthalene-8-yl-carboxamide (A-8, Chart A)

1,2,3,4-Tetrahydrospiro[2-(1,3-dioxolane)-2-naphthalene]-8-yl-carboxamide (7.88 g, 33.8 mmol) was dissolved in acetic acid/THF/water (3:1:1) and heated to 60° for five hours. The solution was cooled and the solvent removed in vacuo to afford a white solid. This was recrystallized from 95% ethanol/cyclohexane to afford 6.0 g (94% yield) of white crystals (m.p. 243° C.).

PREPARATION 8
(1,2,3,4-Tetrahydro-2-oxonaphthalene-8-yl)(2-pyr-rolyl) Ketone (B-2, Chart B)

Pyrrole (3.17 ml) was dissolved in toluene (40 ml) and cooled to 0° while ethylmagnesium bromide (15.2 ml of a 3 M solution in ether) was added. This solution was allowed to warm to 25° and stirred for 30 minutes. A solution of methyl 1,2,3,4-tetrahydrospiro-2-[2-(1,3-dioxolane)] naphthalene-8-yl-carboxylate (5.15 g, 20.8 mmol) dissolved in toluene (20 ml) was added and the solution refluxed for 24 hours. The solution was cooled and quenched by the addition of saturated aqueous ammonium chloride. Ether (100 ml) was added and the solution extracted. The organic layer was washed with water (2×100 ml), saturated aqueous sodium bicarbonate (50 ml) and brine (50 ml). Drying over anhydrous sodium sulfate and solvent removal in vacuo afforded a dark oil. This was placed in a solution of acetic acid/THF/water (3:1:1) and heated to 50° for five hours. After cooling, the solvent was removed in vacuo and the residue placed on a flash silica gel column (3 cm×40 cm) and eluted with ethyl acetate/hexane (40:60) (added methylene chloride to dissolve crystallized product off the column. Solvent removal afforded 3.7 g of the title compound (74% yield) as light yellow needles (m.p. 174° C.).

PREPARATION 9
4-Iodo-N-butyl-(2,3-dihydro-1,1-dioxo-3-benziso-thiazole)

Sodium saccharrin (20 g), 1-chloro-4-bromobutane (16.8 ml) and DMF (150 ml) were stirred at 90° for 15 hours. The solution was cooled and ether (200 ml) and water (400 ml) were added. This was extracted and the organic layer was washed with water (4×300 ml) and brine (100 ml). The organic layer was dried over anhydrous sodium sulfate and the solvent removed in vacuo. The residue was placed on a flash silica gel column and eluted with ethyl acetate/hexane (20:80). Solvent removal in vacuo afforded an oil (24.5 g). This was dissolved in acetone, sodium iodide added (2 eq.) and refluxed for six hours. After filtration and solvent removal in vacuo, the residue was filtered through a plug of flash silica gel with ethyl acetate/hexane (30:70). Solvent removal afforded an oil which solidified upon standing.

PREPARATION 10
3-Iodo-N-propyl-(2,3-dihydro-1,1-dioxo-3-benziso-thiazole) and 5-iodo-N-pentyl-(2,3-dihydro-1,1-dioxo-3-benziso-thiazole as Made in a Manner Analogous to that of Preparation 9

1-Phenyl-2-imidazolidone, 1-(3-chlorophenyl)-2-imidazolidone and 1,(2-methoxyphenyl)-2-imidazolidone were prepared according to the reference: W. B. Wright, Jr., H. J. Brabander, R. A. Hardy, Jr. and A. C. Osterberg, *J. Med. Chem.*, 2, 852 (1966).

PREPARATION 11
1-Phenyl-(4-chlorobutyl)-2-imidazolidone

A mixture of 1-phenyl-2-imidazolidone (W. B. Wright, Jr., H. J. Brabander, R. A. Hardy, Jr. and A. C. Osterberg, *J. Med. Chem.*, 9, 852 (1966) (3.24 g, 0.020 mol), 1-bromo-4-chlorobutane (10.29 g, 0.060 mol), tetrabutylammonium bromide (0.64 g, 2.0 mmol) and 50% aqueous sodium hydroxide (60 mls) in toluene (100 mls) is stirred vigorously in an oil bath maintained at 60° C. for nine hours and at room temperature overnight. The mixture was diluted with water and diethylether and the layers were separated. The aqueous layer was extracted with diethylether and the combined organics were washed with brine and dried (MgSO$_4$). The solvent was removed in vacuo to leave an oil (9.2 g). Purification by flash chromatography (SiO$_2$, 230–400 mesh; 3:1 hexane/ethyl acetate) gave a colorless solid (4.83 g). A sample (0.50 g) was crystallized from diethylether/hexane to give colorless crystals of the title compound (0.489 g) (m.p. 47.5° C.).

PREPARATION 12
1-Phenyl-(4-iodobutyl)-2-imidazolidone

A mixture of the 1-phenyl-(4-chlorobutyl)-2-imidazolidone (1.87 g, 7.4 mmol) and sodium iodide (5.55 g, 37 mmol) in acetone (60 mls) was stirred at reflux for 16 hours. The mixture was stirred at reflux for 16 hours. The mixture was diluted with diethylether, filtered and evaporated to dryness. The residue was partitioned between diethylether and water and the aqueous layer was extracted with methylene chloride. The combined organics were washed with water and brine and dried (MgSO$_4$). The solvent was removed in vacuo to leave the title compound as a yellow solid (2.28 g, 90%).

1-Phenyl-(3-iodopropyl)-2-imidazolidone, 1-(3chlorophenyl)-(4-iodobutyl)-2-imidazolidone, 1,3-chlorophenyl)-(3-iodopropyl)-2-imidazolidone, 1-(2-methoxyphenyl)-(4-iodobutyl)-2-imidazolidone, 2,4-dihydro-2-(4-iodobutyl)-1H-[1,2,4]triazolo[3,4-c][1,4]benzoxazin-1-one and 2,4-dihydro-2-(3-iodopropyl)-1H-[1,2,4]triazolo[3,4-c][1,5]benzoxazin-1-one were prepared in an analogous fashion.

PREPARATION 13
1,2,3,4-Tetrahydro-2-oxo-1-(2-propenyl)-naphthalene (E-2, Chart E) and 1,2,3,4-Tetrahydro-2-oxo-1,1-di-(2-propenyl) naphthalene To a solution of 7.3 g (50 mmol) 2-tetralone in 75 mL THF in a 3-neck round-bottomed flask, equipped with a gas inlet and septum, was added 36.7 mL LDA (55 mmol, 1.5 M in cyclohexane) at −30° C. under a nitrogen atmosphere. The solution was allowed to warm to 0° C. over a 30-minute period and 5.6 mL (65 mmol) allyl bromide was added. TLC analysis was used to monitor the reaction. After stirring for 24 hours at room temperature, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The crude product was purified by liquid chromatography on 800 g of silica gel 60 (230–400 m), eluting with 1 L of hexane, followed by 5 L of 5% ethyl acetate/hexane, and collecting 40 mL fractions. Fractions 65–82 gave 3.1 g (33%) of pure 1,2,3,4-Tetrahydro-2-oxo-1-(2-propenyl)-naphthalene as a light yellow oil.

$^1$HNMR (CDCl$_3$, TMS): 7.27–7.16 (m, 4H); 5.81–4.95 (m, 3H); (s, 3H); 3.54–2.45 (m, 7H).

IR (film): ν$_{max}$ 1717, 1640 and 1582 cm$^{-1}$.

$^M$S: M+186, other ions at m/z 168, 145, 128, 117.

TLC (Silica Gel GF): R$_f$=0.51 in hexane/ethyl acetate (4:1). on. Fractions 41–64 gave 4.2 g (37%) of pure and 1,2,3,4-Tetrahydro-2-oxo-1,1-di-(2-propenyl)naphthalene as a colorless oil

PREPARATION 14
1,2,3,4-Tetrahydro-8-methoxy-2-oxo-1-(2-propenyl)-naphthalene and 1,2,3,4-Tetrahydro-8-methoxy-2-oxo-1-di-(2-propenyl)-naphthalene (E-2, Chart E)

To a solution of 8.8 g (50 mmol) 8-methoxy-2-tetralone in 250 mL THF in a three-neck round-bottomed flask, equipped with a gas inlet and septum, was added 40 mL LDA (60 mmol, 1.5 M in cyclohexane, at −30° C. under a nitrogen atmosphere. The solution was allowed to warm to 0° C. over a 30-minute period and 6.5 mL (75 mmol) allylbromide was added. TLC analysis was used to monitor the reaction. After stirring the mixture at room temperature for three hours and at 40° C. for one hour, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil (about 3b/22b=4 by LC purification in a small scale run) was used without purification in the next step. For the analytical purpose the small amount of the crude product (<1 g) was purified by liquid chromatography on 185 g of silica gel 60(230–400 m), eluting with hexane/acetone (19:1). Fractions homogeneous by TLC were combined and concentrated in vacuo. Pure title compounds were isolated as a light yellow oil.

Physical Data for 1,2,3,4-tetrahydro-8-methoxy-2-oxo-2-(2-propenyl)naphthalene $^1$HNMR (CDCl$_3$, TMS): 7.21–6.76 (m, 3H); 5.73–4.87 (m. 3H); 3.82 (s, 3H); 3.88–3.82 (m, 1H); 3.32–2.43 (m, 6H).

IR (film): ν$_{max}$ 1712,1640, 1586 cm$^{-1}$.

MS: Calcd for C$_{14}$H$_{16}$O$_2$: 216.1150. Found: 216.1151.

Analysis: Calcd for C$_{14}$H$_{16}$O$_2$: C, 77.75; H, 7.46. Found: C, 77.56; H, 7.68.

TLC (Silica Gel GF): Rf=0.32 in hexane/acetone (4:1)

Physical Data for 1,2,3,4-tetrahydro-8-methoxy-2-oxo-1-di-(2-propenyl)-naphthalene
$^1$HNMR (CDCl$_3$, TMS): 7.22–6.73 (m, 3H); 5.44–4.77 (m, 6H); 3.85 (s, 3H); 4.0–2.52 (m, 8H).
IR (film): $v_{max}$ 1712, 1639 and 1582 cm$^{-1}$.
MS: Calcd for C$_{17}$H$_{20}$O$_2$; 256.1463. Found: 256.1470
Analysis: Calcd for C$_{17}$H$_2$O$_2$: C, 79.65; H, 7.86. Found: C, 79.56; H, 8.29.
TLC (Silica Gel GF): Rf=0.46 in hexane/acetone (19:1).

PREPARATION 15
1,2,3,4-Tetrahydro-5-methoxy-2-oxo-1-(2-propenyl)-naphthalene (E-2, Chart E) and 1,2,3,4-Tetrahydro-5-methoxy-2-oxo-1,1-di-(2-pro-penyl)-naphthalene To a solution of 5.3 g (30 mmol) 5-methoxy-2-tetralone in 45 mL THF in a three-neck round-bottomed flask, equipped with a gas inlet and septum, was added 22 mL LDA (33 mmol, 1.5 M in cyclohexane, at −30° C. under a nitrogen atmosphere. The solution was allowed to warm to 0° C. over a thirty-minute period and 3.4 mL (39 mmol) allylbromide was added. TLC analysis was used to monitor the reaction. After five hours of stirring, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil was purified by liquid chromatography on 800 g of silica gel 60 (230–400 m), eluting with 1 L of hexane and 5 L of hexane-ethyl acetate (19:1), and collecting 40 mL fractions. Fractions 45–87 gave 2.5 g (32.5%) of pure 1,2,3,4-tetrahydro-5-methoxy-2-oxo-1,1-di-(2-propenyl)-naphthalene as a near colorless oil and fractions 88–140 gave 1.07 g (16.5%) of pure 1,2,3,4-tetrahydro-5-methoxy-2-oxo-1-(2-propenyl)naphthalene as a light yellow oil.
$^1$HNMR (CDCl$_3$, TMS): 7.23–6.77 (m, 3H); 5.75–4.97 (m, 3H); 3.85 (s, 3H); 3.52–2.49 (m, 7H).
IR (film): $v_{max}$ 1717, 1641 and 1586 cm$^{-1}$.
MS: M$^+$ 216, other ions at m/z 175, 159, 147.
TLC (Silica Gel GF): R$_f$=0.42 in hexane-ethyl acetate (4:1).

PREPARATION 16
1,2,3,4-Tetrahydro-8-methoxy-1-(cyclopropylmethyl)-2-oxo-naphthalene (E-2, Chart E)

To a solution of 3.52 g (20 mmol) 8-methoxy-2-tetralone in 50 mL THF in a three-neck round-bottomed flask, equipped with a gas inlet and septum, was added 14.3 mL LDA (22 mmol, 1.5 M in cyclohexane) at −30° C. under a nitrogen atmosphere. The solution was allowed to warm to 0° C. over a thirty-minute period and 2.4 mL (24 mmol) allyl bromide was added. TLC analysis was used to monitor the reaction. After stirring for two hours, the TLC analysis appeared to show little progress. The reaction mixture was therefore treated with 1.1 mL (12 mmol) allylbromide and the mixture was heated to reflux for 72 hours. The reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil was purified by liquid chromatography on 400 g of silica gel 60 (230–400 m), eluting with hexane/acetone (9:1) and collecting 40 mL fractions. Fractions homogeneous by TLC were combined and concentrated in vacuo to give 4.5 g (97.8%) of pure title compound as a near colorless oil.
$^1$HNMR (CDCl$_3$, TMS): 7.20–6.75 (m, 3H); 3.91 (t, J=7 Hz, 1H); 3.81 (s, 3H); 3.33–1.62 (m, 6H); 0.64–0.09 (m, 5H).
IR (film): $v_{max}$ 1711 cm$^{-1}$.
MS: Calcd for C$_{15}$H$_{18}$O$_2$; 230.1307. Found: 230.1290.
Analysis: Calcd for C$_{15}$H$_{18}$O$_2$: C, 78.23; H, 7.88. Found: C, 77.93; H, 8.06.
TLC (Silica Gel GF): R$_f$=0.46 in hexane-acetone (4:1).

PREPARATION 17
1,2,3,4-Tetrahydro-8-methoxy-2-oxo-1-naphthalene-carboxylic Acid Methyl Ester (F-2, Chart F)

To a solution of 17.6 g (0.1 mol) 8-methoxy-2-tetralone in 200 mL THF in a three-neck round-bottomed flask, equipped with a gas inlet and septum, was added 86.7 mL LDA (0.13 mol, 1.5 M in cyclohexane) at −30° C. under a nitrogen atmosphere. The solution was allowed to warm to 0° C. over a thirty-minute period and 84.3 mL (1.0 mol) dimethylcarbonate was added. After refluxing for 24 hours (bath temperature 70° C.), the TLC analysis indicated no starting material remaining. The reaction mixture was quenched with 1 N HCl to pH 2–3. After removal of THF under reduced pressure, the mixture was extracted with methylene chloride (2×1 L) and the combined organic layers were washed with brine, dried (MgSO$_4$), filtered and concentrated in vacuo. The resulting oil was purified by flash chromatography on 1 Kg of silica gel 60 (230–400 m), eluting with 1 L hexane, 2 L 10%, 8 L 20% ethyl acetate/hexane and collecting 500 mL fractions. Fractions 7–9 gave 0.5 g (2%) of a yellow oil which was shown to be 1,1-dicarbomethoxy product by $^1$HNMR. Fractions 11–22 afforded 21.1 g (90%) of pure title compound as a yellow oil.
$^1$HNMR (CDCl$_3$, TMS): 7.28–6.77 (m, 3H); 4.72 (s, 1H); 3.80 (s, 3H); 3.72–2.17 (m, 7H).
IR (film): $v_{max}$ 1750, 1718 and 1588 cm$^{-1}$.
MS: M$^+$ 234, other ions at m/z 202, 191, 174, 147, 131, 115, 103, 91.
Analysis: Calcd for C$_{13}$H$_{14}$O$_4$: C, 66.65; H, 6.02. Found: C, 66.49; H, 5.93.
TLC (Silica Gel GF): R$_f$=0.33 in hexane/ethyl acetate (3:1).

PREPARATION 18
1,2,3,4-Tetrahydro-8-methoxy-2-oxo-3-(2-propenyl)-1-naphthalene-carboxylic Acid Methyl Ester (F-3, Chart F)

A solution of 10.2 g (43.5 mmol) 1,2,3,4-tetrahydro-8-methoxy-2-oxo-1-naphthalene carboxylic acid methyl ester in 108 mL of THF in a three-neck, round-bottomed flask, equipped with a dropping funnel, was added dropwise 63.8 mL (95.7 mmol) of LDA (1.5 M in cyclohexane) at −30° C. to −40° C. under a nitrogen atmosphere. The solution was allowed to warm to 0° C. and 6.0 mL (69.6 mmol) of allylbromide was added. After stirring the mixture for one hour at room temperature, TLC analysis showed no starting material remaining. The reaction was quenched with 3N hydrochloric acid to pH 2–3 and extracted with ethyl acetate (2×1 L). The combined organic layers were washed with brine, dried (MgSO$_4$), filtered, and concentrated in vacuo. The resulting oil was purified by liquid chromatography on 800 g silica gel 60 (230–400 m), eluting with hexane-acetone (3: 1), and collecting 40 mL fractions. Fractions 36–63 gave 10.3 g (87%) of pure title compound as a yellow oil.
$^1$HNMR (CDCl$_3$, TMS): 7.27–6.76 (m, 3H); 5.89–5.02 (m, 3H); 4.75, 4.59 (two s, 1H); 3.80, 3.81 (two s, 6H); 3.32–1.64 (m, 5H).
IR (film): $v_{max}$ 1751, 1717 and 1589 cm$^{-1}$.
MS: M$^+$ 274, other ions at m/z 242, 233, 214, 201, 187, 173, 159, 145.
Analysis: Calcd for C$_{16}$H$_{18}$O$_4$: C, 70.05; H, 6.61. Found: C, 69.73; H, 6.65.

TLC (Silica Gel GF): Rf=0.34 in hexane-ethyl acetate (3:1).

PREPARATION 19
1,2,3,4-Tetrahydro-8-methoxy-3-(2-propenyl)-2-oxo-naphthalene (F-4, Chart F)

To a solution of 10.3 g (37.6 mmol) of 1,2,3,4-tetrahydro-8-methoxy-2-oxo-3-(2-propenyl)-1-naphthalene carboxylic acid methyl ester in 26.3 mL of DMSO and 1.1 mL of water was added 1.9 g (45.1 mmol) of lithium chloride. The reaction mixture was heated at 125° C. (bath temperature) for five hours. TLC analysis showed no starting material remaining. The mixture was cooled to room temperature and extracted with ethyl acetate (1 L). The organic layer was washed with 10% aqueous calcium sulfate (an efficient way of removing DMSO from organic layer), dried (MgSO$_4$), filtered and concentrated in vacuo. The crude product was purified by liquid chromatography on 800 g silica gel 60 (230–400 m), eluting with hexane-ethyl acetate (3:1), and collecting 40 mL fractions. Fractions 26–53 gave 7.65 g (94%) of pure title compound as a yellow oil.

$^1$HNMR (CDCl$_3$, TMS): 7.18–6.74 (m, 3H); 5.95–4.95 (m, 3H); 3.82 (s, 3H); 3.70–2.08 (m, 7H).

IR (film): $v_{max}$ 1756, 1710 and 1589 cm$^{-1}$.

MS: M$^+$ 216,other ions at m/z 185, 174, 159, 146, 134, 115, 104.

Analysis: Calcd for C$_{14}$H$_{16}$O$_2$: C, 77.75; H, 7.46. Found: C, 77.21; H, 7.65.

TLC (Silica Gel Gf): Rf=0.53 in hexane-ethyl acetate (3:1).

PREPARATION 20 (±)
1,2,3,4-Tetrahydro-8-methoxy-2-(2-propenyl-N-[Z-oxo] propyl-amino)-1-naphthalene Carboxylic Acid Methyl Ester (G-3, Chart G).

A solution of the free base of cis and trans isomers of 1,2,3,4-tetrahydro-8-methoxy-2-(2-propenyl amino)-1-naphthalene carboxylic acid methyl ester, in 5 ml pyridene and 10 ml of methylene chloride was treated with 2.5 ml (20 mol) of propionic anhydride. After 3 hours of stirring at room temperature, TLC analysis showed no starting material remaining. The mixture was quenched with 1 ml lactic acid to destroy excess reagent and extracted with methylene chloride. The organic layer was washed with 10% sodium bisulfate, brine 10% sodium hydroxide, brine, dried (MgSO$_4$), filtered and concentrated to give a light yellow oil. The oil was purified by LC eluting with acetone-hexane (2:1) collecting 40 ml fractions. Fraction 10–20 afforded 1.4 g (84%) of title compound.

$^1$HNMR (CDCl$_3$, TMS): 7.20–6.60(m, 3H); 5.92–5.10 (m, 3H); 4.85–4.30(m, 1H); 4.0–3.6(m, 2H); 3.75(s, 3H); 3.67(s, 3H); 3.10–1.82(m, 6H); 1.17(t, 3H)

PREPARATION 21
1,2,3,4-Tetrahydro-8-methoxy-T-hydroxy methyl-2-(2-propenyl-N-propyl)naphthaleneanene (G-4, Chart G).

1.33 g (4 mol) 1,2,3,4-Tetrahydro-8-methoxy-2-(2-propenyl-[2-oxopropyl]amino)naphthalene carboxylic acid methyl ester was dissolved in 40 ml THF and treated with 0.91 $_5$(24 mol) lithium aluminum hydride. The mixture was refluxed for 3 hours. The mixture was quenched with saturated sodium sulfate, diluted with 500 ml THF, dried (MgSO$_4$) filtered and concentrated to yield on oil. The oil was purified by LC eluting with hexane-aceton (2:1) and collecting 40 ml fractions. Fraction S24–28 afforded a light yellow oil as title compound which did not crystallize upon conversion to an HCl salt.

$^1$HNMR (CDU$_3$, TMS): 7.13–6.64 (m, 3H); 6.00–5.14 (m, 3H); 3.92–3.70 (m, 2H); 3.82 (s, 3H); 3.68–1.42 (m, 10H); 0.90 (t, 3H).

PREPARATION 22
8-bromo-2-tetralone (H-2, Chart H)

Substitute 2-bromophenylacetylchloride in the procedure detailed in A. H. Horn, C. J. Grol, D. Dijkstra, and A. H. Mulder, J. Med. Chem. 21, 825 (1978).

PREPARATION 23
8-bromo-2-(spiro-1,3-dioxolan-2-yl)tetralin (H-3, Chart H)

8-Bromo-2-tetralone (29 g), ethylene glycol (24 g), p-toluenesulfonic acid (0.5 g), and benzene (250 ml) were heated to reflux with azeotropic removal of water for 16 hr. The solution was cooled and extracted with aq. sodium carbonate, water, and then brine. The solution was dried over anhydrous sodium sulfate and the solvent removed under vacuum.

PREPARATION 24
8-trifluoromethyl-2-(spiro-1,3-dioxolan-2-yl)tetralin (H-4, Chart H)

8-Bromo-2-(spiro-1,3-dioxolan-2-yl)tetralin (12.4 g), sodium trifluoroacetate (25 g), copper (I) iodide (17.5 g) and N-methyl pyrrolidone (368 ml) were heated under nitrogen to 160° C. and maintained there for 4 hr. The solution was cooled and ether and hexane were added. The slurry was filtered through diatomaceous earth and the elutant was washed with water (3×) and brine. The solution was dried over anhydrous sodium sulfate and the solvent removed under vacuum. Flash chromatography was performed, eluting with ether/hexane (1:9) giving 9.9 g of a pure liquid.

PREPARATION 25
8-trifluoromethyl-2-tetralone (H-5, Chart H)

8-Trifluoromethyl-2-(spiro-1,3-dioxolan-2-yl)tetralin (9.9 g), water (15 ml), THF (120 ml), and 2 N aq. HCl (12 ml) were heated to 50° C. for 15 hr. This solution was cooled and extracted with ether, washing the organic layer with aq. sodium bicarbonate and then brine. Drying over anhydrous sodium sulfate and solvent removal afforded a clear liquid.

PREPARATION 26
8-trifluoromethyl-2-amino Compounds in Optically Active Form (H-6, Chart H)

8-Bromo-2-tetralone (15.2 g), (R)-(+)-alpha-methylbenzylamine (46 ml), acetic acid (add until pH reaches 5), methanol (100 ml), and THF (100 ml) were stirred at 0° C. for 30 min. Sodium cyanoborohydride (9 g) was added and the reaction was stirred for 3 hr at 0° C. The solvent was then removed under vacuum. The residue was placed on a 5 cm wide flash silica gel column and eluted with ethyl acetate/hexane (8:92 changing to 15:85). The higher Rf diastereomer solidified upon standing whereas the lower Rf diastereomer remained an oil.

PREPARATION 27
Optically Active 8-trifluoromethyl-2N-[(R)-alpha-methylbenzyl]propionamid-2-yl-tetralin (H-7, Chart H)

Note: both diastereomers were separately carried through this step. The product from the reductive amination (vide supra) (8.4 g) was dissolved in methylene chloride (50 ml) and triethylamine (4 ml) and cooled to 0°. Propionylchloride (2.5 ml) was added and the solution was stirred for 1 hr. Ether (75 ml) was added and the reaction was washed with water (2×), aq. sodium bicarbonate, and brine. The organic layer was dried over anhydrous sodium sulfate and the solvent removed under vacuum. A clear liquid (10.2 g) was obtained.

PREPARATION 28

Optically Active 8-trifluoromethyl-2N-[(R)-alpha-methylbenzyl-2N-n-propylaminotetralin (H-8, Chart H)

Note: both diastereomers were separately carried through this step. 8-Trifluoromethyl-2N-[(R)-alpha-methylbenzyl] propionamid-2-yl-tetralin (10.2 g) was dissolved in THF (60 ml). Borane dimethylsulfide complex (13.5 ml of a 10 M solution) was added and the solution brought to reflux for 3 hr. The reaction was cooled to 0° C. and 2N aq. HCl was added slowly. 3 N aq. sodium hydroxide was added to pH 12 and the solution was extracted with ether. The ether solution was washed with water and brine. The solvent was removed under vacuum and the residue placed on the head of a 1 cm flash silica gel column and eluted with ether. The solvent was removed to afford 9 g of pure title compound.

PREPARATION 29

8-Aminosulfonyl-2-(spiro-1,3-dioxolan-2-yl)tetralin (J-2, Chart J) Magnesium (3.83 g, 0.158 mol) was covered with dry tetrahydrofuran (250 mls), and 8-bromo-2-(spiro-1,3-dioxolan-2-yl)tetralin (28.29 g, 0.105 mol) was added. A few crystals of iodine were added, and the mixture was heated to reflux on the steam bath until the reaction became exothermic. The reaction was stirred at ambient temperature until the reaction subsided. The reaction mixture was refluxed gently on the steam bath for an additional 40 minutes. The Grignard solution was removed from the excess magnesium via needle stock and cooled to −15° C. Sulfur dioxide gas was bubbled through the solution for 30 minutes. The mixture was diluted with diethylether and washed with dilute hydrochloric acid and brine containing sodium bicarbonate. The solution was dried ($MgSO_4$), and the solvent was removed under vacuum to leave the sulfonic acid as (J-2) an off-white solid (27.26 g).

(J-3, Chart J) Sodium hydride (5.3 g, 50% in oil, 0.11 mol) was washed twice with hexane, and covered with dry tetrahydrofuran (400 mls). A solution of the sulfonic acid (26.38 g, 0.104 mol) in dry tetrahydrofuran (300 mls) was added via needle stock. The mixture was stirred at room temperature overnight and then heated at reflux for 15 minutes. The mixture was diluted with diethylether, and the precipitate was filtered while blowing argon over the surface of the compound. The compound was washed several times with diethylether, and dried under vacuum leaving the sodium sulfonate as a solid (26.77 g).

(J-4, Chart J) A suspension of the sodium sulfinate (26.77 g, 0.0969 mol) in methylene chloride (400 mls) was cooled in ice, and N-chlorosuccinimide (13.75 g, 0.103 mol) was added. The mixture was stirred at room temperature for 2 hours. Diethylether was added, and the mixture was washed with water and brine. The solution was dried ($MgSO_4$), and the solvent was removed under vacuum to leave the sulfonyl chloride as an amber solid (23.3 g).

(J-5, Chart J) A solution of the sulfonyl chloride (23.3 g) in tetrahydrofuran (80 mls) was added to an ice-cooled solution of ammonium hydroxide (100 mls) in acetone (500 mls). The cold bath was removed, and the mixture was stirred for 2 hours. The solvent was evaporated, and the residue was partioned between 4:1 diethylether/tetrahydrofuran and brine. The solution was washed twice with 2% hydrochloric acid, sat. sodium bicarbonate, and brine. The solution was dried ($MgSO_4$), and the solvent was removed under vacuum to leave the sulfonamide as a tan solid (19.8 g). A sample (0.75 g) was crystallized from ethyl acetate/hexane to give off-white crystals of the sulfonamide (0.68 g, m.p. 127–128° C).

PREPARATION 30

8-Aminosulfonyl-2-tetralone (J-6, Chart J)

8-Aminosulfonyl-2-(spiro-1,3-dioxolan-2-yl)tetralin (18.36 g, 0.0682 mol) was dissolved in acetone (400 mls), and p-toluenesulfonic acid (1.85 g, 9.7 mmol, 14 mol percent) was added. The mixture was stirred at room temperature for 21 hours. Saturated sodium bicarbonate (50 mls) was added, and the solvent was removed under vacuum. The residue was diluted with water and cooled in ice. The precipitate was filtered, washed with water, and dried under vacuum. The compound was boiled in ethyl acetate (350–400 mls) until most of the solid dissolved and then filtered. Hexane was added, and crystallization occurred leaving the ketone as an orange solid (10.34 g, m.p. 173–175° C.).

EXPERIMENTAL PROCEDURES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 31

7-(1-hexahydroazepinyl)-5,6,7,8-tetrahydronaphthalene-1-trifluoromethylsulfonate (L-2, Chart L)

A solution of 2.1 g 7-(1-hexahydroazepinyl)-5,6,7,8-tetrahydro-1-naphthalenol and 4.06 g pyridine in 100 mL $CH_2Cl_2$ was stirred and cooled to 0 °C. under a nitrogen atmosphere. The trifluoromethanesulfonic anhydride (4.32 g) was added dropwise over a 20 min period. The yellow solution was warmed to room temperature and stirred for 45 min. TLC aliquot showed no starting material present. The reaction was quenched with satd. $NaHCO_3$ to pH>8. The mixture was extracted with methylene chloride. The organic layers were washed with water, brine, dried ($MgSO_4$), filtered and concentrated to yield an oil. Flash chromatography on 1 kg silica gel eluting with hexane/ethyl acetate (1:1) (collecting 45 mL fractions) yielded a pale yellow oil (3.05 g, 95%)

PREPARATION 32

7-(1-Hexahydroazepinyl)-5,6,7,8-tetrahydronaphthalene-1-carboxylic Acid Methyl Ester (L-3, Chart L)

A solution of 2.9 g 7-(1-hexahydroazepinyl)-5,6,7,8-tetrahydronaphthalene-1-trifluoro-methylsulfonate and 2.13 mL triethylamine in 9 mL methanol and 27 mL DMF was degassed with nitrogen through a syringe for 10 min. Carbon monoxide was then bubbled through the solution for 10 min. During this time, a solution if 172 mg palladium acetate and 379 mg in 7 mL DMF was dissolved and degassed with nitrogen for 10 min. This solution was added to the reaction , heated to 7° C. and carbon monoxide gas bubbled through overnight. An aliquot was treated with satd. $NaHCO_3$ and EtOAc and showed no starting material. Nitrogen was bubbled through the solution and then quenched with satd. $NaHCO_3$. The mixture was extracted with ethyl acetate (3×500 ml) and the combined organic layers were washed with brine, dried ($MgSO_4$), filtered and concentrated to yield an oil. Flash chromatography using 400 g silica gel and eluting with hexane/ethyl acetate (1:1) to yield an oil (1.56 g, 71%).

PREPARATION 33
7-(1-Hexahydroazepinyl)-5,6,7,8-tetrahydronaphthalene-1-carboxylic Acid (L-4, Chart L)

A mixture of 1.56 g 7-(1-Hexahydroazepinyl)-5,6,7,8-tetrahydronaphthalene-1-carboxylic acid methyl ester, 1.57 mL 12 N NaOH, 1.57 mL water in 10 mL methanol was refluxed (70–80° C.) overnight. TLC showed no starting material remaining. The mixture was neutralized with 6 N HCl to pH 5–6 and concentrated to dryness using toluene and methanol. A white solid was recovered and used crude.

PREPARATION 34
8-bromo-2-tetralone (M-2, Chart M)

Substitute 2-bromophenylacetylchloride in the procedure detailed in A. H. Horn, C. J. Grol, D. Dijkstra, and A. H. Mulder, J. Med. Chem. 21, 825 (1978).

PREPARATION 35
8-bromo-2-(spiro-1,3-dioxolan-2-yl)tetralin (N-2, Chart N)

8-Bromo-2-tetralone (29 g), ethylene glycol (24 g), p-toluenesulfonic acid (0.5 g), and benzene (250 ml) were heated to reflux with azeotropic removal of water for 16 hr. The solution was cooled and extracted with aq. sodium carbonate, water, and then brine. The solution was dried over anhydrous sodium sulfate and the solvent removed under vacuum.

PREPARATION 36
8-trifluoromethyl-2-(spiro-1,3-dioxolan-2-yl)tetralin (N-3, Chart N)

8-Bromo-2-(spiro-1,3-dioxolan-2-yl)tetralin (12.4 g), sodium trifluoroacetate (25 g), copper (I) iodide (17.5 g) and N-methyl pyrrolidone (368 ml) were heated under nitrogen to 160° C. and maintained there for 4 hr. The solution was cooled and ether and hexane were added. The slurry was filtered through diatomaceous earth and the elutant was washed with water (3×) and brine. The solution was dried over anhydrous sodium sulfate and the solvent removed under vacuum. Flash chromatography was performed, eluting with ether/hexane (1:9) giving 9.9 g of a pure liquid.

PREPARATION 37
8-trifluoromethyl-2-tetralone (N-4, Chart N)

8-Trifluoromethyl-2-(spiro-1,3-dioxolan-2-yl)tetralin (9.9 g), water (15 ml), THF (120 ml), and 2 N aq. HCl (12 ml) were heated to 5° C. for 15 hr. This solution was cooled and extracted with ether, washing the organic layer with aq. sodium bicarbonate and then brine. Drying over anhydrous sodium sulfate and solvent removal afforded a clear liquid.

PREPARATION 38
1,2,3,4-Tetrahydro-2-oxo-1-(2-propenyl)-naphthalene (E-2, Chart E) and 1,2,3,4-Tetrahydro-2-oxo-1,1-di-(2-propenyl) naphthalene To a solution of 7.3 g (50 mmol) 2-tetralone in 75 ML THF in a 3-neck round-bottomed flask, equipped with a gas inlet and septum, was added 36.7 mL LDA (55 mmol, 1.5 M in cyclohexane) at −30° C. under a nitrogen atmosphere. The solution was allowed to warm to 0° C. over a 30-minute period and 5.6 mL (65 mmol) allyl bromide was added. TLC analysis was used to monitor the reaction. After stirring for 24 hours at room temperature, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The crude product was purified by liquid chromatography on 800 g of silica gel 60 (230–400 m), eluting with 1 L of hexane, followed by 5 L of 5% ethyl acetate/hexane, and collecting 40 mL fractions. Fractions 65–82 gave 3.1 g (33%) of pure 1,2,3,4Tetrahydro-2-oxo-1-(2-propenyl)-naphthalene as a light yellow oil.

$^1$HNMR (CDCl$_3$, TMS): 7.27–7.16 (m, 4H); 5.81–4.95 (m, 3H); (s, 3H); 3.54–2.45 (m, 7H).

IR (film): v$_{max}$ 1717, 1640 and 1582 cm$^{-1}$.

$^M$S: M$^+$ 186, other ions at m/z 168, 145, 128, 117.

TLC (Silica Gel GF): R$_f$=0.51 in hexane/ethyl acetate (4:1). on. Fractions 41–64 gave 4.2 g (37%) of pure and 1,2,3,4-Tetrahydro-2-oxo-1,1-di-(2-propenyl)naphthalene as a colorless oil

PREPARATION 39
1,2,3,4-Tetrahydro-8-methoxy-2-oxo-1-(2-propenyl)-naphthalene and 1,2,3,4-Tetrahydro-8-methoxy-2-oxo-1-di-(2-propenyl)-naphthalene (E-2, Chart E)

To a solution of 8.8 g (50 mmol) 8-methoxy-2-tetralone in 250 mL THF in a three-neck round-bottomed flask, equipped with a gas inlet and septum, was added 40 mL LDA (60 mmol, 1.5 M in cyclohexane, at −30° C. under a nitrogen atmosphere. The solution was allowed to warm to 0° C. over a 30-minute period and 6.5 mL (75 mmol) allylbromide was added. TLC analysis was used to monitor the reaction. After stirring the mixture at room temperature for three hours and at 40° C. for one hour, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil (about 3b/22b=4 by LC purification in a small scale run) was used without purification in the next step. For the analytical purpose the small amount of the crude product (<1 g) was purified by liquid chromatography on 185 g of silica gel 60(230–440 m), eluting with hexane/acetone (19:1). Fractions homogeneous by TLC were combined and concentrated in vacuo. Pure title compounds were isolated as a light yellow oil.

Physical Data For 1,2,3,4-tetrahydro-8-methoxy-2-oxo-2-(2-propenyl)naphthlene $^1$HNMR (CDCl$_3$, TMS): 7.21–6.76 (m, 3H); 5.73–4.87 (m. 3H); 3.82 (s, 3H); 3.88–3.82 (m, 1H); 3.32–2.43 (m, 6H).

IR (film): v$_{max}$ 1712,1640, 1586 cm$^{-1}$.

MS: Calcd for C$_{14}$H$_{16}$O$_2$; 216.1150. Found: 216.1151.

Analysis: Calcd for C$_{14}$H$_{16}$O$_2$: C, 77.75; H, 7.46. Found: C, 77.56; H, 7.68.

TLC (Silica Gel GF): Rf =0.32 in hexane/acetone (4:1)

Physical Data for 1,2,3,4-tetrahydro-8-methoxy-2-oxo-1-di-(2-propenyl)-naphthlene $^1$HNMR (CDCl$_3$, TMS): 7.22–6.73 (m, 3H); 5.44–4.77 (m, 6H); 3.85 (s, 3H); 4.0–2.52 (m, 8H).

IR (film): v$_{max}$ 1712, 1639 and 1582 cm$^{-1}$.

MS: Calcd for C$_{17}$H$_{20}$O$_2$; 256.1463. Found: 256.1470

Analysis: Calcd for C$_{17}$H20O$_2$: C, 79.65; H, 7.86. Found: C, 79.56; H, 8.29.

TLC (Silica Gel GF): Rf=0.46 in hexane/acetone (19:1).

PREPARATION 40
1,2,3,4Tetrahydro-5-methoxy-2-oxo-1-(2-propenyl)-naphthalene (E-2, Chart E) and 1,2,3,4-Tetrahydro-5-methoxy-2-oxo-1,1-di-(2-pro-penyl)-naphthalene To a solution of 5.3 g (30 mmol) 5-methoxy-2-tetralone in 45 mL THF in a three-neck round-bottomed flask, equipped with a gas inlet and septum, was added 22 mL LDA (33 mmol, 1.5 M in cyclohexane, at −30° C. under a nitrogen atmosphere. The solution was allowed to warm to 0° C. over a thirty-minute period and 3.4 mL (39 mmol) allylbromide was added. TLC analysis was used to monitor the reaction. After five hours of stirring, the reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil was purified by liquid chromatography on 800 g of silica gel 60 (230–400 m), eluting with 1 L of hexane and 5 L of hexane-ethyl acetate (19:1), and collecting 40 mL fractions. Fractions 45–87 gave 2.5 g (32.5%) of pure 1,2,3,4-tetrahydro-5-methoxy-2-oxo-1,1-di-(2-propenyl)-naphthalene as a near colorless oil and fractions 88–140 gave 1.07 g (16.5%) of pure 1,2,3,4-tetrahydro-5-methoxy-2-oxo-12-propenyl)naphthalene as a light yellow oil.

$^1$HNMR (CDCl$_3$, TMS): 7.23–6.77 (m, 3H); 5.75–4.97 (m, 3H); 3.85 (s, 3H); 3.52–2.49 (m, 7H).

IR (film): $v_{max}$ 1717, 1641 and 1586 cm$^{-1}$.

MS: M$^+$ 216, other ions at m/z 175, 159, 147.

TLC (Silica Gel GF): R$_f$=0.42 in hexane-ethyl acetate (4:1).

PREPARATION 41
1,2,3,4-Tetrahydro-8-methoxy-1-(cyclopropylmethyl)-2-oxo-naphthalene (E-2, Chart E)

To a solution of 3.52 g (20 mmol) 8-methoxy-2-tetralone in 50 mL THF in a three-neck round-bottomed flask, equipped with a gas inlet and septum, was added 14.3 mL LDA (22 mmol, 1.5 M in cyclohexane) at –30° C. under a nitrogen atmosphere. The solution was allowed to warm to 0° C. over a thirty-minute period and 2.4 mL (24 mmol) allyl bromide was added. TLC analysis was used to monitor the reaction. After stirring for two hours, the TLC analysis appeared to show little progress. The reaction mixture was therefore treated with 1.1 mL (12 mmol) allylbromide and the mixture was heated to reflux for 72 hours. The reaction mixture was quenched with 10% sodium bisulfate to pH 2–3. After removal of THF under reduced pressure, the mixture was extracted with ethyl acetate (2×1 L) and the combined organic layers were washed with brine, dried (MgSO$_4$), filtered and concentrated in vacuo. The resulting oil was purified by liquid chromatography on 400 g of silica gel 60 (230–400 m), eluting with hexane/acetone (9:1) and collecting 40 mL fractions. Fractions homogeneous by TLC were combined and concentrated in vacuo to give 4.5 g (97.8%) of pure title compound as a near colorless oil.

1HNMR (CDCl$_3$, TMS): 7.20–6.75 (m, 3H); 3.91 (t, J=7 Hz, 1H); 3.81 (s, 3H); 3.33–1.62 (m, 6H); 0.64–0.09 (m, 5H).

IR (film): $v_{max}$ 1711 cm$^{-1}$.

MS: Calcd for C$_{15}$H$_{18}$O$_2$; 230.1307. Found: 230.1290.

Analysis: Calcd for C$_{15}$H$_{18}$O$_2$: C, 78.23; H, 7.88. Found: C, 77.93; H, 8.06.

TLC (Silica Gel GF): R$_f$=0.46 in hexane-acetone (4:1).

PREPARATION 42
1,2,3,4-Tetrahydro-8-methoxy-2-oxo-1-naphthalene-carboxylic Acid Methyl Ester (F-2, Chart F)

To a solution of 17.6 g (0.1 mol) 8-methoxy-2-tetralone in 200 mL THF in a three-neck round-bottomed flask, equipped with a gas inlet and septum, was added 86.7 mL LDA (0.13 mol, 1.5 M in cyclohexane) at –30° C. under a nitrogen atmosphere. The solution was allowed to warm to 0° C. over a thirty-minute period and 84.3 mL (1.0 mol) dimethylcarbonate was added. After refluxing for 24 hours (bath temperature 70° C.), the TLC analysis indicated no starting material remaining. The reaction mixture was quenched with 1 N HCl to pH 2–3. After removal of THF under reduced pressure, the mixture was extracted with methylene chloride (2×1 L) and the combined organic layers were washed with brine, dried (MgSO$_4$), filtered and concentrated in vacuo. The resulting oil was purified by flash chromatography on 1 Kg of silica gel 60 (230–400 m), eluting with 1 L hexane, 2 L 10%, 8 L 20% ethyl acetate/hexane and collecting 500 mL fractions. Fractions 7–9 gave 0.5 g (2%) of a yellow oil which was shown to be 1,1-dicarbomethoxy product by $^1$HNMR. Fractions 11–22 afforded 21.1 g (90%) of pure title compound as a yellow oil.

$^1$HNMR (CDCl$_3$, TMS): 7.28–6.77 (m, 3H); 4.72 (s, 1H); 3.80 (s, 3H); 3.72–2.1 (m, 7H).

IR (film): $v_{max}$ 1750, 1718 and 1588 cm$^{-1}$.

MS: M$^+$ 234, other ions at m/z 202, 191, 174, 147, 131, 115, 103, 91.

Analysis: Calcd for C$_{13}$H$_{14}$O$_4$: C, 66.65; H, 6.02. Found: C, 66.49; H, 5.93.

TLC (Silica Gel GF): R$_f$=0.33 in hexane/ethyl acetate (3:1).

PREPARATION 43
1,2,3,4Tetrahydro-8-methoxy-2-oxo-3-(2-propenyl)-1-naphthalene-carboxylic Acid Methyl Ester (F-3, Chart F)

A solution of 10.2 g (43.5 mmol) 1,2,3,4-tetrahydro-8-methoxy-2-oxo-1-naphthalene carboxylic acid methyl ester in 108 mL of THF in a three-neck, round-bottomed flask, equipped with a dropping funnel, was added dropwise 63.8 mL (95.7 mmol) of LDA (1.5 M in cyclohexane) at –30° C. to –40° C. under a nitrogen atmosphere. The solution was allowed to warm to 0° C. and 6.0 mL (69.6 mmol) of allylbromide was added. After stirring the mixture for one hour at room temperature, TLC analysis showed no starting material remaining. The reaction was quenched with 3N hydrochloric acid to pH 2–3 and extracted with ethyl acetate (2×1 L). The combined organic layers were washed with brine, dried (MgSO$_4$), filtered, and concentrated in vacuo. The resulting oil was purified by liquid chromatography on 800 g silica gel 60 (230–400 m), eluting with hexane-acetone (3:1), and collecting 40 mL fractions. Fractions 36–63 gave 10.3 g (87%) of pure title compound as a yellow oil.

$^1$HNMR (CDCl$_3$, TMS): 7.27–6.76 (m, 3H); 5.89–5.02 (m, 3H); 4.75, 4.59 (two s, 1H); 3.80, 3.81 (two s, 6H); 3.32–1.64 (m, 5H).

IR (film): $v_{max}$ 1751, 1717 and 1589 cm$^{-1}$.

MS: M$^+$ 274, other ions at m/z 242, 233, 214, 201, 187, 173, 159, 145.

Analysis: Calcd for C$_{16}$H$_{18}$O$_4$: C, 70.05; H, 6.61. Found: C, 69.73; H, 6.65.

TLC (Silica Gel GF): Rf=0.34 in hexane-ethyl acetate (3:1).

PREPARATION 44
1,2,3,4Tetrahydro-8-methoxy-3-(2-propenyl)2-oxo-naphthalene (F-4, Chart F)

To a solution of 10.3 g (37.6 mmol) of 1,2,3,4-tetrahydro-8-methoxy-2-oxo-3-(2-propenyl)-1-naphthalene carboxylic acid methyl ester in 26.3 mL of DMSO and 1.1 mL of water was added 1.9 g (45.1 mmol) of lithium chloride. The reaction mixture was heated at 125° C. (bath temperature) for five hours. TLC analysis showed no starting material remaining. The mixture was cooled to room temperature and extracted with ethyl acetate (1 L). The organic layer was washed with 10% aqueous calcium sulfate (an efficient way of removing DMSO from organic layer), dried (MgSO$_4$), filtered and concentrated in vacuo. The crude product was purified by liquid chromatography on 800 g silica gel 60 (230–400 m), eluting with hexane-ethyl acetate (3:1), and collecting 40 mL fractions. Fractions 26–53 gave 7.65 g (94%) of pure title compound as a yellow oil.

$^1$HNMR (CDCl$_3$, TMS): 7.18–6.74 (m, 3H); 5.95–4.95 (m, 3H); 3.82 (s, 3H); 3.70–2.08 (m, 7H).

IR (film): $v_{max}$ 1756, 1710 and 1589 cm$^{-1}$.

MS: M+ 216, other ions at m/z 185, 174, 159, 146, 134, 115, 104.

Analysis: Calcd for C$_{14}$H$_{16}$O$_2$: C, 77.75; H, 7.46. Found: C, 77.21; H, 7.65.

TLC (Silica Gel Gf): Rf=0.53 in hexane-ethyl acetate (3:1).

PREPARATION 45

8-Aminosulfonyl-2-(spiro-1,3-dioxolan-2-yl)tetralin. (J-2, Chart J)

Magnesium (3.83 g, 0.158 mol) was covered with dry tetrahydrofuran (250 mls), and 8-bromo-2-(spiro-1,3-dioxolan-2-yl)tetralin (28.29 g, 0.105 mol) was added. A few crystals of iodine were added, and the mixture was heated to reflux on the steam bath until the reaction became exothermic. The reaction was stirred at ambient temperature until the reaction subsided. The reaction mixture was refluxed gently on the steam bath for an additional 40 minutes. The Grignard solution was removed from the excess magnesium via needle stock and cooled to −15° C. Sulfur dioxide gas was bubbled through the solution for 30 minutes. The mixture was diluted with diethylether and washed with dilute hydrochloric acid and brine containing sodium bicarbonate. The solution was dried (MgSO$_4$, and the solvent was removed under vacuum to leave the sulfinic acid as an off-white solid (27.26 g).

(H-3, Chart H) Sodium hydride (5.3 g, 50% in oil, 0.11 mol) was washed twice with hexane, and covered with dry tetrahydrofuran (400 mls). A solution of the sulfinic acid (26.38 g, 0.104 mol) in dry tetrahydrofuran (300 mls) was added via needle stock. The mixture was stirred at room temperature overnight and then heated at reflux for 15 minutes. The mixture was diluted with diethylether, and the precipitate was filtered while blowing argon over the surface of the compound. The compound was washed several times with diethylether, and dried under vacuum leaving the sodium sulfinate as a solid (26.77 g).

(H$_4$, Chart H) A suspension of the sodium sulfinate (26.77 g, 0.0969 mol) in methylene chloride (400 mls) was cooled in ice, and N-chlorosuccinimide (13.75 g, 0.103 mol) was added. The mixture was stirred at room temperature for 2 hours. Diethylether was added, and the mixture was washed with water and brine. The solution was dried (MgSO$_4$), and the solvent was removed under vacuum to leave the sulfonyl chloride as an amber solid (23.3 g).

(H-5, Chart H) A solution of the sulfonyl chloride (23.3 g) in tetrahydrofuran (80 mls) was added to an ice-cooled solution of ammonium hydroxide (100 mls) in acetone (500 mls). The cold bath was removed, and the mixture was stirred for 2 hours. The solvent was evaporated, and the residue was partioned between 4:1 diethylether/tetrahydrofuran and brine. The solution was washed twice with 2% hydrochloric acid, sat. sodium bicarbonate, and brine. The solution was dried (MgSO$_4$), and the solvent was removed under vacuum to leave the sulfonamide as a tan solid (19.8 g). A sample (0.75 g) was crystallized from ethyl acetate/hexane to give off-white crystals of the sulfonamide (0.68 g, m.p. 127–128° C.).

PREPARATION 46

8-Aminosulfonyl-2-tetralone (J-6, Chart J)

8-Aminosulfonyl-2spiro-1,3-dioxolan-2-yl)tetralin (18.36 g, 0.0682 mol) was dissolved in acetone (400 mls), and p-toluenesulfonic acid (1.85 g, 9.7 mmol, 14 mol percent) was added. The mixture was stirred at room temperature for 21 hours. Saturated sodium bicarbonate (50 mls) was added, and the solvent was removed under vacuum. The residue was diluted with water and cooled in ice. The precipitate was filtered, washed with water, and dried under vacuum. The compound was boiled in ethyl acetate (350–400 mls) until most of the solid dissolved and then filtered. Hexane was added, and crystallization occurred leaving the ketone as an orange solid (10.34 g, m.p. 173–175° C.).

PREPARATION 47

8-Carbomethoxy-2-[spiro-2-(1,3-dioxolyl)]tetralin (B-1, Chart B)

8-Trifluoromethylsulfonyl-2-[spiro-2-(1,3-dioxolyl)]tetralin (62 g, 183.4 mmol) was placed in a round bottom flask with palladium acetate (2.88 g, 7 mol %), bis(diphenylphosphino)propane (6.81 g, 9 mol %), diisopropylamine (70.3 ml, 2.2 eq.), methanol (183 mi) and dimethylsulfoxide (550 ml). The flask was thoroughly flushed with carbon monoxide, which was subsequently bubbled through the solution. The solution was heated to 70° and stirred for four hours. The solution was cooled and 400 ml. of methylene chloride and 800 ml of ether added. This solution was washed with water (4×500 ml) and brine (400 ml), and dried over anhydrous sodium sulfate. Solvent removal in vacuo and filtration through a plug of flash silica gel (6 cm×30 cm) with ethyl acetate/hexane (25:75), followed by solvent removal afforded 39 g of the title compound (85% yield) as an oil.

PREPARATION 48

(1,2,3,4-Tetrahydro-2-oxonaphthalene-8-yl)(2-pyrrolyl) Ketone (B-2, Chart B)

Pyrrole (3.17 ml) was dissolved in toluene (40 ml) and cooled to 0° while ethylmagnesium bromide (15.2 ml of a 3 M solution in ether) was added. This solution was allowed to warm to 25° and stirred for 30 minutes. A solution of methyl 1,2,3,4-tetrahydrospiro-2-[2-(1,3-dioxolane)]naphthalene-8-yl-carboxylate (5.15 g, 20.8 mmol) dissolved in toluene (20 ml) was added and the solution refluxed for 24 hours. The solution was cooled and quenched by the addition of saturated aqueous ammonium chloride. Ether (100 ml) was added and the solution extracted. The organic layer was washed with water (2×100 ml), saturated aqueous sodium bicarbonate (50 ml) and brine (50 ml). Drying over anhydrous sodium sulfate and solvent removal in vacuo afforded a dark oil. This was placed in a solution of acetic acid/THF/water (3:1:1) and heated to 50° for five hours. After cooling, the solvent was removed in vacuo and the residue placed on a flash silica gel column (3 cm×40 cm) and eluted with ethyl acetate/hexane (40:60) (added methylene chloride to dissolve crystallized product off the column. Solvent removal afforded 3.7 g of the title compound (74% yield) as light yellow needles (m.p. 174° C.).

EXAMPLE 1

1,2,3,4-Tetrahydro-2-N-propylaminonaphthalene-8-yl-carbox-amide (A-9, Chart A)

1,2,3,4-Tetrahydro-2-oxo-naphthalene-8-yl-carboxamide (1.8 g, 9.5 mmol), acetic acid (2.27 ml, 4 eq.), N-propylamine (3.12 ml, 4 eq.), sodium cyanoborohydride (900 mg) and methanol (15 ml) were stirred at 25° for two hours. Ether (100 ml) was added and the solution was washed with saturated aqueous sodium carbonate (30 ml), water (50 ml) and brine (30 ml), and dried over anhydrous sodium sulfate. Solvent removal in vacuo afforded a white foam. Crystallization as the hydrochloride salt from methanol/ether afforded the title compound as white needles (m.p. 225° C.).

Utilizing a procedure similar to that of Example 1, but substituting the appropriate amine for N-propylamine there is obtained 1,2,3,4-tetrahydro-2-N-(2-propenyl)aminonaphthalene-8-yl carboxamide crystallized as the maleic acid salt from acetonitrile (m.p. 136° C.);

1,2,3,4-tetrahydro-2-N-cyclopropylmethylaminonaphthalene8-yl-carboxamide crystallized as the maleic acid salt from methanol/diethylether (m.p. 112° C.).

EXAMPLE 2

1,2,3,4-tetrahydro-2-N-cyclopropylmethylaminonaphthalene-8-yl-N-methylcarboxamide Oxalate Utilizing a procedure similar to that of Example 1 but substituting the appropriate N-methylcarboxamide for the carboxamide the title compound is crystallized as the oxalate salt from methanol/diethylether (m.p. 225° C. dec).

EXAMPLE 3

1,2,3,4-Tetrahydro-2-N,N-dipropylaminonaphthalene-8-yl-carboxamide (A-10, Chart A)

1,2,3,4-Tetrahydro-2-N-propylaminonaphthalene-8-yl-carboxamide (1.3 g, 5.6 mmol), sodium carbonate (712 mg), n-bromopropane (0.66 ml) and acetonitrile (15 ml) were refluxed for 30 hours. The reaction was cooled and poured into a solution of methylene chloride (50 ml) and ether (50 ml). This was extracted with water (2×50 ml) and brine (50 ml), and dried over anhydrous sodium sulfate. Solvent removal in vacuo afforded 1.38 g (90% yield) of product. The title compound was crystallized as its hydrochloride salt from methanol/ether (m.p. 142° C.).

Utilizing a procedure similar to that of Example 2, there is obtained 1,2,3,4-tetrahydro-2-N,N-cyclopropylmethylaminonaphthalene-8-yl-carboxamide as the fumarate salt from methanol/ether (m.p. 109° C.).

EXAMPLE 4

1,2,3,4-tetrahydro-2-N,N-dicyclopropylmethylaminonaphtha-lene-8-yl-N-methylcarboxamide Utilizing procedure similar to Example 3 but utilizing the 1,2,3,4tetrahydro-2-N-cyclopropylmethylaminonaphthalene-8-yl-carboxamide and bromomethylcyclopropane, there is obtained the title compound, m.p. 120° C. from ethyl acetate/hexane.

Also utilizing a procedure similar to that of Example 3, but substituting the appropriate carboxamide and halo substituted compound there is obtained 1,2,3,4-tetrahydro-2-N,N-di-n-propylaminonaphthalene-8-yl-N-benzyloxycarbonylcarboxamide, maleic acid salt (m.p. 147 °C.);

1,2,3,4-2-N,N-di-cyclopropylmethylaminonaphthalene-o-yl-N-methylcarboxamide (m.p. 120° C.).

EXAMPLE 5

Utilizing a procedure similar to that of Example 2, but substituting the appropriate haloalkane for n-bromopropane and where necessary the appropriate N-alkyl-aminotetralin for the N-propyl aminotetralin there is obtained 1,2,3,4-tetrahydro-2-N-n-propyl-2-N-[4-(2,3-dihydro-1,1-dioxo-3-benziso-thiazolyl)]butyl-8-yl-carboxamide: Crystallized as a white foam (m.p. 80° C.).

1,2,3,4-Tetrahydro-2-N-cyclopropylmethyl-2-N-propyl-8-yl-carboxamide: Crystallized from methanol/ether (m.p. 97° C.).

1,2,3,4-tetrahydro-2-N-n-propyl-2-(N-trimethylsilyl) aminonaphthalene-8-yl-carboxamide (m.p. 229° C.).

EXAMPLE 6

(1,2,3,4-Tetrahydro-2-N-propylaminonaphthalene-8-yl)(2-pyrrolyl)ketone (B-3, Chart B)

(1,2,3,4-Tetrahydro-2-oxo-naphthalene-8-yl)(2-pyrrole) ketone (2.27 g, 9.5 mmol), as prepared in Preparation 8, N-propylamine (3.12 ml, 4 eq.), acetic acid (2.17 ml, 4 eq.), platinum oxide (200 mg), and absolute ethanol (30 ml) were combined in a Parr flask and allowed to stir for three hours. A hydrogen atmosphere (50 psi) was introduced and the mixture was shaken for three hours, then filtered and the solvent removed in vacuo. The residue was extracted with ether (150 ml) and saturated aqueous sodium carbonate (25 ml). The organic layer was washed with water (50 ml) and brine (50 ml), and dried over anhydrous sodium sulfate. Solvent removal in vacuo accorded an oil which was placed on a flash silica gel column (2 cm×40 cm) and eluted with methanol/methylene chloride (2:98, switching to 10:90 to elute off product). Solvent removal afforded a foam which was crystallized as its hydrochloride salt from methanol/ether to obtain needles of the title compound (m.p. 256° C.).

EXAMPLE 7

(1,2,3,4-Tetrahydro-2-N,N-dipropylaminonaphthalene-8-yl) 2-pyrrole)ketone (B4, Chart B)

(1,2,3,4-Tetrahydro-2-N-propylaminonaphthalene-8-yl) (2-pyrrole) ketone (1.58 g, 5.6 mmol), sodium carbonate (712 mg), n-bromopropane (0.66 ml) and acetonitrile (10 ml) were refluxed for 24 hours. This mixture was added to ether (150 ml) and saturated aqueous sodium carbonate (20 ml) and extracted. The organic layer was washed with water (2×50 ml), brine (50 ml) and dried over anhydrous sodium sulfate and the solvent removed in vacuo. The residue was placed on a flash silica gel column (2 cm×40 cm) and eluted with ethyl acetate/hexane (successively going from 15:85, 20:80 and 40:60). Solvent removal in vacuo afforded a dark oil. This solidified on standing to yield the title compound (m.p. 75° C.).

EXAMPLE 8

8-Methoxy-N-propyl-N-[3-(2,3dihydro-1,1-dioxo-3oxo-1,2-benzisothiazolyl)propyl]-2-aminotetralin 8-Methoxy-N-propyl-2-aminotetralin (Arvidsson L.-E. et al., *J. Med. Chem.*, 27, 45 (1984) (2 g, 10 mmol), N-(3-iodopropyl)-2,3-dihydro-1,1-dioxo-3-benzisothiazolone (7.5 g), sodium carbonate (2.5 g), and acetonitrile (25 ml) were heated to reflux for 24 hours. After cooling, the solvent was removed in vacuo and the residue placed on a flash silica gel column (3 cm×35 cm) and eluted with ethyl acetate/hexane (5:95, 10:90, 15:85, 20:80, successively). Solvent removal in vacuo afforded the title compound as a white powder (m.p. 131° C.).

EXAMPLE 9

8-Methoxy-N-propyl-N-[4-(2,3-dihydro-1,1-dioxo-3-oxo-1,2-benzisothiazolyl)butyl]-2-aminotetralin Using a procedure similar to that used in Example 8, there is obtained 8-Methoxy-N-propyl-N-[4-(2,3-dihydro-1,1-dioxo-3oxo-1,2-benziso-thiazolyl)butyl]-2-aminotetralin as an oil;

EXAMPLE 10
8-Methoxy-N-propyl-N-[5-(2,3-dihydro-1,1-dioxo-3-oxo-1, 2-benzisothiazolyl)]pentyl-2-aminotetralin Using a procedure similar to that of Example 8 there is obtained 8-Methoxy-N-propyl-N-[5-(2,3-dihydro-1,1-dioxo-3-oxo-1,2-benzisothiazolyl)]-pentyl-2-aminotetralin as an oil.

EXAMPLE 11
8-Hydroxy-N-propyl-N-[3-(2,3-dihydro-1,1-dioxo-3-oxo-1, 2-benzoisothiazolyl)]propyl-2-aminotetralin 8-Methoxy-N-propyl-N-13-(2,3-dihydro-1,1-dioxo-3-oxo-1,2-benziso-thiazolyl)propyl-2-aminotetralin (2.12 g, 4.65 mmol) and 48% hydrobromic acid (20 ml) were heated to 135° for 90 minutes. The solvent was removed in vacuo and the residue partitioned between ether (100 ml) and ammonium hydroxide (100 ml). The organic layer was washed with water (2×100 ml) and brine (50 ml) and dried over anhydrous sodium sulfate. Solvent removal in vacuo afforded an oil which was placed on a flash silica gel column (3 cm×35 cm) and eluted with ethyl acetate/hexane (25:75). Solvent removal in vacuo followed by crystallization of the hydrochloride salt from methanol/ether afforded the title compound as a fine white powder (m.p. 191° C.).

EXAMPLE 12
8-Hydroxy-N-propyl-N-[4-(2,3-dihydro-1,1-dioxo-3-oxo-1, 2-benzisothiazolyl)]butyl-2-aminotetralin, Hydrochloride Utilizing the procedure of Example 11, but starting with the appropriate aminotetralin there is obtained
8-Hydroxy-N-propyl-N-[4(2,3-dihydro-1,1-dioxo-3-oxo-1, 2-benzisothiazolyl)]butyl-2-aminotetralin crystallized as the hydrochloride salt (m.p. 262° C.), and
8-Hydroxy-N-Propyl-N-[5-(2,3-dihydro-1,1-dioxo-3-oxo-1, 2-benzoiso-thiazolyl)]pentyl-2-aminotetralin crystallized as the hydrobromide salt (m.p. 169° C.).

EXAMPLE 13
8-Cyano-N,N dipropyl-2-aminotetralin

8Carboxamide-N,N dipropyl-2-aminotetralin (1.0 g, 3.6 mmol) was dissolved in methylene chloride (15 ml). Burgess Salts (the inner salt of methyl[carboxysulfamoyl] triethylammonium hydroxide; *Organic Synthesis*, 56, page 40) (2.4 g) was added in portions over 20 minutes. The reaction was allowed to stir for three hours, then placed directly on a flash silica gel column (2 cm×35 cm) and eluted with ethyl acetate/hexane (30:70). Solvent removal in vacuo afforded 0.87 g of an oil which was crystallized from methanol/ether (m.p. 158° C.).

EXAMPLE 14
8Cyano-N-cyclopropyl-N-propyl-2-aminotetralin

Synthesized using the above procedure (m.p. 158° C.).

EXAMPLE 15
(±)-Octahydro-1-(1,2,3,4 tetrahydro-8-methoxy-2-naphthalenyl)-azocine Hydrochloride (C-2, Chart C).

To a solution of 1.76 g (10 mmol) 8-methoxy tetralone and 5.66 g (50 mmol) heptamethylenamine in 30 mL MeOH/TiF (1:1) was added HOAc dropwise to adjust the pH to 4–5. The reaction mixture stirred for 15 minutes under $N_2$, then 1.26 g (20 mmol) $NaCNBH_3$ was added. When the reaction was complete by TLC (24 h), 1 N NaOH (25 mL) and $H_2O$ (200 mL) was added to quench the reaction. The solution was extracted with $CH_2Cl_2$ (2×500 mL) and the combined organic layers were washed with brine, dried ($MgSO_4$), filtered and concentrated in vacuo. The resulting was purified by liquid chromatography on 400 g of silica gel 60 (230–400m), eluting with hexane/acetone (5:1). Fractions homogeneous by TLC were combined and concentrated in vacuo to give pure compound as an oil. The HCl salt was formed by using a MeOH/HCl solution. The title compound was recovered as a white solid by recrystallization using EtOAc/MeOH (2.65 g, 86%): mp. 211–213° C.

$^1$HNMR ($CDCl_3$, TMS): 7.13(t, 1H); 6.69 (t, 2H); 3.81 (s, 3H); 3.54 (m, 3H), 3.31–3.18 (m, 3H); 2.94–2.67 (m, 4H); 2.17 (m, 2H); 2.1–1.46 (m, 8H).

IR (mull): $v_{max}$ 2529, 2503, 1585, 1470, 1463, 1453, 1251 $cm^{-1}$.

Analysis: Calcd for $C_{18}H_{27}NO.HCl$: C, 69.769; H, 9.108; N, 4.521. Found: C, 69.6; H, 9.24; N, 4.65.

Utilizing a procedure similar to Example 15, but substituting the appropriate amine for heptamethyleneamine there is obtained the following compounds.

(±)-1,2,3,4-Tetrahydro-8-methoxy-N-methyl-N-(2-methyl-2-propenyl)-2-naphthalenamine Hydrochloride as a White Solid, m.p. 184°–184° C.

$^1$HNMR ($CDC_3$, TMS): 7.15 (t, 1H); 6.70 (q, 2H); 5.29 (s, 2H); 3.83 (s, 3H); 3.65 (m, 2H); 3.4–3.2 (m, 3H); 2.97 (m, 2H); 2.80–2.77 (m, 3H); 2.16 (t, 2H); 1.6 (s, 3H).

IR (mull): $v_{max}$ 2867, 2855, 2556, 2541, 1648, 1589, 1443 $cm^{-1}$.

Analysis: Calcd for $C_{16}H_{23}NO.HCl$: C, 68.435; H, 8.256; N, 4.988. Found: C, 68.23; H, 8.46; N, 5.21.

(±)-N-(1,2,3,4-Tetrahydro-8-methoxy-2-naphthalenyl)-glycine Ethyl Ester Hydrochloride as a White Solid $^1$HNMR ($CDCl_3$, TMS): 7.10 (t, 1H); 6.67 (q, 2H); 4.30 (m, 2H); 4.12–3.9 (m, 2H); 3.78 (s, 3H); 3.60–3.30 (m, 2H); 2.92 (m, 3H); 2.6 (m, 1H); 2.12 (m, 1H); 1.52 (m, 1H), 1.32 (m, 3H).

IR (mull): $v_{max}$ 2810, 2620, 1763, 1758, 1593, 1583, 1471, 1464 $cm^{-1}$.

Analysis: Calcd for $C_{15}H_{21}NO^3.HCl$: C, 60.096; H, 7.397; N, 4.673. Found: C, 58.07; H, 7.36; N, 5.17.

(±)-1,2,3,4-Tetrahydro-8-methoxy-N-propyl-2-naphthalenamine Hydrochloride, White Solid; m.p. 192°–195° C.

$^1$HNMR ($CDCl_3$, TMS): 7.13 (t, 1H); 6.78–6.77 (q, 2H); 3.82 (s, 3H); 3.47 (m, 1H); 3.30–3.29 (m, 3H); 3.09 (m, 2H); 2.92 (m, 2H); 2.52 (q, 1H); 2.28 (m, 1H); 1.85–1.72 (m, 3H); 1.09–1.04 (t, 3H).

IR (mull): $v_{max}$ 2954, 2397, 1615, 1587, 1461 $cm^{-1}$.

Analysis: Calcd for $C_{14}H_{21}NO.HCl$: C, 65.74; H, 8.67; N, 5.4762 Found: C, 64.56; H, 8.64; N, 5.47.

(±)-1,2,3,4 Tetrahydro-8-methoxy-N-methyl-N-2-propynyl-2-naphthalenamine Hydrochloride as a White Solid: m.p. 210°–211° C.

$^1$HNMR ($CDC_3$, TMS): 7.15 (t, 1H); 6.70 (t, 2H); 4.25 (m, 1H); 3.9 (m, 1H); 3.81 (s, 3H); 3.7–3.2 (m, 3H); 3.7–3.3 (m, 2H); 2.99–2.94 (m, 5H); 2.66 (m, 1H); 2.5 (m, 1H); 1.63 (t, 2H).

IR (mull): $v_{max}$ 3194, 2515, 2490, 1590, 1468, 1457, 1443 $cm^{-1}$.

Analysis: Calcd for $C_{15}H_{19}NO.HCl$: C, 67.787; H, 7.585; N, 5.270. Found: C, 67.51; H, 7.81; N, 5.41.

(±)-N-(2,2-dimethylpropyl)-1,2,3,-tetrahydro-8-methoxy-2-naphthalenamine Hydrochloride White Solid: m.p. 240°–244° C.

$^1$HNMR ($CDCl_3$, TMS): 7.09 (t, 1H); 6.65 (q, 2H); 3.73 (s, 3H); 3.6–3.45 (m, 2H); 2.85 (m, 5H); 1.64 (d, 4H); 1.21 (s, 9H).

IR (mull): $v_{max}$ 2668, 2436, 1589, 1462, 1447, 1406 $cm^{-1}$.
Analysis: Calcd for $C_{16}H_{25}NO.HCl$: C, 67.70; H, 9.23; N, 4.93. Found: C, 65.29; H, 9.20; N, 5.76.

(±)-5-Methoxy-N-(1,2,3,4-tetrahydro-8-methoxy-2-naphthalenyl)1-H-indole-3-ethanamine Monohydrochloride White Solid: m.p. 203°–204° C.

¹HNMR (CDCl₃, TMS): 7.28–6.70 (m, 7H); 3.84 (s, 3H); 3.81 (s, 3H); 3.62–1.72 (m, 11H).

IR (mull): $v_{max}$ 3260, 1608, 1590 cm⁻¹.

Analysis: Calcd for $C_{22}H26N_2O_2 \cdot HCl$: C, 68.29; H, 7.03; N, 7.24. Found: C, 68.31; H, 7.09; N, 7.24.

(±)-Trans-3,5-dimethyl-1-(1,2,3,4-tetrahydro-8-methoxy-2-naphthalenyl)-piperidine Hydrochloride as a White Solid, 1.78 g, 33% (m.p. 230–232° C.).

¹HNMR (CDCl₃, TMS): 7.09–7.04 (t, 1H); 6.71–6.6 (q, 2H); 3.82 (s, 3H); 2.87–2.27 (m, 9H); 1.91 (m, 2H); 1.60 (m, 2H); 1.32–1.28 (m, 2H); 0.98 (s, 3H); 0.97 (s, 3H).

IR (mull): $v_{max}$ 3005, 3035, 2200, 1590 and 1460 cm⁻¹.

Analysis: Calcd for $C_{18}H_{27}NO \cdot HCl$: C, 67.77; H,9.11; N, 4.52. Found: C, 69.61; H, 9.05; N, 4.57.

cis-3,5-dimethyl-1-(1,2,3,4-tetrahydro-8-methoxy-2-naphthalenyl)piperidine Hydrochloride as a White Solid, 2.36 g, 43% (m.p. 231–233° C.).

¹HNMR (CDCL₃,TMS): 7.14 (t, 1H); 6.77–6.67 (q, 2H); 3.82 (s, 3H); 3.6–3.36 (m, 4H); 2.96 (m, 2H); 2.75 (m, 4H); 2.45 (q, 1H); 2.3 (q, 1H); 1.9 (m, 2H); 1.68 (m, 1H); 0.99 (s, 3H); 0.97 (s, 3H).

IR (mull): $v_{max}$ 3005, 3035, 2200, 1590, 1460 cm⁻¹.

Analysis: Calcd for $C_{18}H_{27}NO \cdot HCl$: C, 69.77; H, 9.11; N, 4.52. Found: C, 69.71; H, 9.08; N, 4.77.

3,5-Dimethyl-1-(1,2,3,4-tetrahydro-8-methoxy-2-naphthalenyl)-piperidine Hydrochloride White Solid: m.p. >200° C. ¹HNMR (CDCl₃, TMS): 7.15 (t, 1H); 6.69 (t, 2H); 3.83 (s, 3H); 3.71 (m, 1H); 3.5–2.3 (m, 9H); 1.60 (s, 6H); 1.53 (m, 2H); 0.98 (m, 3H).

IR (mull): $v_{max}$ 3000, 2450 cm⁻¹.

Analysis: Calcd for $C_{18}H_{27}NO \cdot HCl$: C, 68.77; H, 9.11; N, 4.52. Found: C, 68.99; H, 9.07; N, 4.67.

(±)-N-ethyl-1,2,3,4-tetrahydro-8-methoxy-N-2-propenyl-2-naphthalenamine Hydrochloride White Solid ¹HNMR (CDCl₃, TMS): 7.14 (t, 1H); 6.70 (q, 2H); 6.35(m, 1H); 5.54–5.46 (m, 2H); 3.82 (s, 3H); 3.75–3.49 (m, 2H); 3.19 (m, 2H); 2.96 (m, 2H); 1.99 (m, 1H); 1.66 (m, 2H); 1.57–1.49 (m, 3H); 2.75–2.70 (m, 2H).

IR (mull): $v_{max}$ 2474, 1647, 1603, 1584, 1473, 1466, 1400, and 1257 cm⁻¹.

Analysis: Calcd for $C_{16}H_{23}NO \cdot HCl$: C, 68.190; H, 8.584; N, 4.970. Found: C, 67.76; H, 8.60; N, 5.03.

TLC (Silica Gel GF): $R_f$=0.59 in hexane/acetone (3:1).

1,2,3,4Tetrahydro-8-methoxy-N-methyl-N-2-propenyl-2-Naphthalenamine Hydrochloride White Solid: m.p. 191°–192° C.

¹HNMR (CDCl₃, TMS): 7.16 (m, 1H); 6.75–6.69 (m, 2H); 6.45 (m, 1H); 5.55 (m, 2H); 3.83 (s; 3H); 3.81–3.50 (m, 2H); 3.1–2.5 (m, 6H); 1.9 (m, 1H); 1.61 (s, 3H).

IR (mull): $v_{max}$ 2469, 1644, 1604, 1586, 1472, 1434 and 1251 cm⁻¹.

Analysis: Calcd for $C_{15}H_{21}NO \cdot HCl$: C, 67.277; H, 8.281; N, 5.231. Found: C, 67.33; H, 8.25; N, 5.58.

TLC (Silica Gel GF): $R_f$=0.5 in hexane/acetone (3:1).

(±)-1,2,3,4-Tetrahydro-8-methoxy-N-(phenylmethyl)-2-naphthalenamine Hydrochloride White Solid: m.p. 219.8° C.

¹HNMR (CDCl₃, TMS): 7.37–7.24 (m, 5H); 7.08 (t, 1H); 6.68 (q, 2H); 3.97 (s, 2H); 3.81 (s, 3H); 3.10 (dd, 1H); 2.99–2.7 (m, 3H); 2.38 (q, 1H); 1.66–1.55 (m, 3H).

IR (mull): $v_{max}$ 2440, 1604, 1590, 1500, 1469, 1313, 1300, and 1264 cm⁻¹.

Analysis: Calcd for $C_{18}_{21}HNO \cdot HCl$: C, 71.57; H, 7.29; N, 4.61. Found: C, 70.68; H, 7.47; N, 4.76.

TLC (Silica Gel GF): $R_f$=0.38 in hexane/acetone (4:1).

(±)-N-cyclohexyl-1,2,3,4-tetrahydro-8-methoxy-2-naphthalenamine Hydrochloride White Solid: m.p. 247°–248° C.

¹HNMR (CDCl₃, TMS): 7.13 (t, 1H); 6.78 (q, 2H); 3.83 (s, 3H); 3.59 (m, 1H); 3.29 (m, 1H); 2.94 (m, 2H); 2.49 (q, 1H); 2.24 (m, 1H); 2.09 (m, 2H); 1.89 (m, 2H); 1.69 (m, 2H); 1.39–1.29 (m, 5H).

IR (mull): $v_{max}$ 2645, 2582, 2487, 2390, 1931, 1604, 1589, 1472, 1437, and 1253 cm⁻¹.

Analysis: Calcd for $C_{17}H_{25}NO \cdot HCl$: C, 69.067; H, 8.859; N, 4.735. Found: C, 68.46; H, 8.99; N, 4.82.

TLC (Silica Gel GF): $R_f$=0.39 in hexane/acetone (4:1).

N-cycloheptyl-1,2,3,4-tetrahydro-8-methoxy-2-naphthalenamine Hydrochloride White Solid: m.p. 234°–236° C.

¹HNMR (CDCl₃, TMS): 7.12–7.07 (t, 1H); 6.69–6.63 (q, 2H); 3.78 (s, 3H); 3.4–3.30 (m, 3H); 2.96–2.87 (m, 3H); 2.60 (m, 1H); 2.45 (m, 1H); 2.25–2.1 (m, 2H); 2.1–1.87 (m, 4H); 1.65–1.40 (m, 8H).

IR (mull): $v_{max}$ 2490, 1602, 1586, 1569, 1470, 1455, 1436, and 1257 cm⁻¹.

Analysis: Calcd for $C_{18}H_{27}NO \cdot HCl$: C, 69.77; H, 9.10; N, 4.52. Found: C, 69.76; H, 9.17; N, 4.76.

N-(1,1-dimethyl-2-propynyl)-1,2,3,4-tetrahydro-8-methoxy-2-naphthalenamine Hydrochloride White Solid: m.p. 225°–227° C.

¹HNMR (CDCl₃, TMS): 7.17–7.12 (t, 1H); 6.7–6.6 (t, 2H); 3.87 (s, 3H); 3.67 (m, 1H); 3.37 (m, 1H); 2.97–2.80 (m, 3H); 2.56 (m, 1H); 2.05 (m, 1H); 1.83 (s, 3H); 1.82 (s, 3H).

Analysis: Calcd for $C_{16}H_{21}NO \cdot HCl$: C, 68.681; H, 7.926; N, 5.006. Found: C, 68.46; H, 8.26; N,5.15.

(±)-1,2,3,4-Tetrahydro-8-methoxy-N-(2-methyl-2-propenyl)-2-naphthalenamine Hydrochloride White Solid: m.p. 175°–177° C.

¹HNMR (CDCl₃, TMS): 7.13–7.09 (t, 1H); 6.70–6.63 (q, 2H); 5.31 (s, 1H); 5.20 (s, 1H); 3.76 (s, 3H); 3.7 (m, 2H); 3.4 (m, 2H); 2.98 (m, 3H); 2.59 (m, 1H); 2.1 (m, 1H); 2.03 (s, 3H).

IR (mull): $v_{max}$ 2950, 2655, 2409, 1610, 1600, 1440 cm⁻¹.

Analysis: Calcd for $C_{15}H_{21}NO \cdot HCl$: C, 67.277; H, 8.281; N, 5.23. Found: C, 67.37; H, 8.46; N, 5.21.

(±)-N-1-Ethylpropyl)1,2,3,4-tetrahydro-8-methoxy-2-naphthalenamine Hydrochloride White Solid: m.p. 174°–175° C.

¹HNMR (CDCl₃, TMS): 7.10 (t, 1H); 6.70–6.63 (q, 2H); 3.77 (s, 3H); 3.49–3.3 (m, 2H); 3.25 (m, 2H); 3.05–2.89 (m, 3H); 2.27–2.10 (m, 1H).

IR (mull): $v_{max}$ 2900, 2850, 2519, 2467, 1600, 1475, and 1460 cm⁻.

Analysis: Calcd for $C_{16}H_{25}NO \cdot HCl$: C, 67.706; H, 9.234; N, 4.935. Found: C, 67.79; H, 9.46; N, 5.06.

N-cyclobutyl-1,2,3,4-tetrahydro-8-methoxy-2-naphthalenamine Hydrochloride White Solid: m.p. 198°–202° C.

¹HNMR (CDCl₃, TMS): 7.12–7.06 (t, 1H); 6.70–6.66 (q, 2H); 3.81 (s, 3H); 3.57 (d, 2H); 3.2–3.03 (m, 2H); 2.86 (m, 2H); 2.21 (t, 1H); 2.0 (m, 1H); 1.61 (m, 1H).

IR (mull): $v_{max}$ 2950, 2910, 2860, 2400, 1600, 1460 cm⁻¹.

Analysis: Calcd for $C_{15}H_{21}NO \cdot HCl$: C, 67.277; H, 8.281; N, 5.231. Found: C, 67.18; H, 8.39; N, 5.16.

N-(1,2,3,4-tetrahydro-8-methoxy-2-naphthalenyl)-bicyclo-[2.2.1]heptane-2-amine Hydrochloride, White Solid: 254°–256° C.

¹HNMR (MeOH, TMS): 7.15–7.10 (t, 1H); 6.78–6.71 (q, 2H); 3.82 (s, 3H); 3.55 (m, 1H); 3.30 (m, 3H); 2.9 (m, 2H); 2.6–2.3 (m, 4H); 1.7–1.63 (m, 6H); 1.4–1.2 (m,3H).

IR (mull): $v_{max}$ 2945, 2600, 2455, 2420, 1602, 1587 and 1460 cm⁻.

Analysis: Calcd for $C_{18}H_{25}NO \cdot HCl$: C, 70.226; H, 8.513; N, 4.550. Found: C, 69.92; H, 8.73; N, 4.59.

(±)-Hexahydro-1-(1,2,3,4-tetrahydro-8-methoxy-2-naphthalenyl)-1H-azepine Hydrochloride White Solid: m.p. 236°–237° C.

$^1$HNMR (CDCl$_3$, TMS): 7.12–7.04 (t, 1H); 6.71–6.64 (q, 2H); 3.81 (s, 3H); 3.0–2.76 (m, 7H); 2.45 (q, 1H); 2.0 (m, 1H); 1.62 (m, 10H).

IR (mull): $v_{max}$ 3000, 2600, 2550, 1590, 1480 cm$^{-1}$.

Analysis: Calcd for C$_{17}$H$_{25}$NO.HCl: C, 69.017; H, 8.859; N, 4.735. Found: C, 68.91; H, 9.04; N, 4.67.

TLC (Silica Gel GF): R$_f$=0.3 in hexane/acetone (4:1).

(±)-N-ethyl-1,2,3,4-tetrahydro-8-methoxy-N2-methyl-2-propenyl)-2-naphthalenamine, Hydrochloride, White Solid: m.p. 155°–156° C.

$^1$HNMR (CDCl$_3$, TMS): 7.10–7.04 (t, 1H); 6.71–6.64 (q, 2H); 4.93 (s, 1H); 4.79 (s, 1H); 3.82 (s, 3H); 3.06 (s, 2H); 2.93–2.86 (m, 4H); 2.59–2.53 (m, 4H); 2.0 (m, 1H); 1.74 (s, 3H); 1.56 (s, 3H); 1.06–1.01 (t, 3H).

IR (mull): $v_{max}$ 3078, 2950, 2420, 1648, 1591 cm$^1$.

Analysis: Calcd for C$_{17}$H$_{25}$NO.HCl: C, 69.017; H, 8.859; N, 4.735. Found: C, 67.76; H, 8.77; N, 4.73. (1.6% residue)

(±)-1,2,3,4-Tetrahydro-8-methoxy-N-[[3(trifluoromethyl)-phenyl]methyl]-2-naphthalenamine Hydrochloride, White Solid: m.p. 204°–297° C.

IR (mull): $v_{max}$ 3000, 2950, 2800, 2600, 2550, 2400, 1570 and 1460 cm$^{-1}$.

Analysis: Calcd for C$_{19}$H$_{20}$NOF$_3$.HCl: C, 67.844; H, 6.293; N, 4.164. Found: C, 58.50; H, 5.29; N, 4.01.

3,3-Dimethyl-1(1,2,3,4-tetrahydro-8-methoxy-2-naphthalenyl)-piperidine Hydrochloride, White Solid: m.p. 223°–229° C.

$^1$HNMR (CDCl$_3$, TMS): 7.09–7.04 (t, 1H); 6.71–6.63 (q, 1H); 3.81 (s, 3H); 2.80 (m, 4H); 2.56 (m, 3H); 2.23 (s, 2H); 2.0 (m, 1H); 1.60 (m, 4H); 1.25(m, 2H); 0.95 (s, 3H); 0.94 (s, 3H).

IR (mull): $v_{max}$ 2500 and 1590 cm$^{-1}$.

Analysis: Calcd for C$_{18}$H$_{28}$NO.HCl: C, 69.543; H, 9.403; N, 4.506. Found: C, 69.53; H, 9.18; N, 4.88.

4-(1,2,3,4-Tetrahydro-8-methoxy-2-naphthalenyl)-thiomorpholine Hydrochloride, White Solid: m.p. 259°–260° C.

$^1$HNMR (CDCl$_3$, TMS): 7.11–7.05 (t, 1H); 6.71–6.64 (q, 2H); 3.81 (s, 3H); 2.97–2.70 (m, 12H); 2.53–2.44 (q, 1H); 1.98 (m, 1H); 1.70–1.49 (m, 2H).

IR (mull): $v_{max}$ 2609, 2474, 1602, 1590, 1473, 1417 and 1257 cm$^{-1}$.

Analysis: Calcd for C$_{15}$H$_{21}$NOS.HCl: C, 60.084; H, 7.396; N, 4.672. Found: C, 59.15; H, 7.50; N, 4.70.

1,2,3,4-Tetrahydro-8-methoxy-N,N-di-2-propenyl-2-naphthalenamine Hydrochloride (2.1 g, 83%) m.p. Hygroscopic Foam $^1$HNMR (CDCl$_3$, TMS): 7.10–7.05 (t, 1H); 6.71–6.6 (q, 2H); 5.95–5.81 (m, 2H); 5.24–2.09 (m, 4H); 3.91 (s, 3H); 3.27–3.24 (m, 4H); 3.04–2.90 (m, 2H); 2.85–2.80(m, 2H); 2.51 (m, 1H); 2.00 (m, 1H); 1.64–1.58 (m, 1H).

IR (mull): $v_{max}$ 3400, 3000, 2990, 2200, 1590 and 1460 cm$^1$.

Analysis: Calcd for C$_{17}$H$_{23}$NO.HCl: C, 69.40; H, 8.23; N, 4.76. Found: C, 67.65; H, 7.48; N, 5.86.

1,2,3,4-Tetrahydro-8-methoxy-N-2-propenyl-2-naphthalenamine Hydrochloride, White Solid: m.p. 179°–181° C.

$^1$HNMR (CDCl$_3$, TMS): 7.11–7.06 (t, 1H); 6.73–6.64 (q, 2H); 6.02–5.89 (m, 1H); 5.24–5.08 (q, 2H); 3.81 (s, 3H); 3.40–3.38 (d, 2H); 3.12–3.05 (dd, 1H); 2.95–2.83 (m, 3H); 2.36–2.28 (q, 1H); 2.01 (m, 1H); 1.63–1.54 (m, 1H).

IR (mull): $v_{max}$ 1610, 1590, 1460 cm$^1$.

Analysis: Calcd for C$_{14}$H$_{19}$NO.HCl: C, 66.26; H, 7.94; N, 5.52. Found: C, 65.80; H, 8.10; N, 5.63.

1,2,3,4-Tetrahydro-8-methoxy-N-2-propynyl-2-naphthalenamine White Solid: m.p. 84°–85° C.

$^1$HNMR (CDCl$_3$, TMS): 7.13–7.07 (t, 1H); 6.69–6.63 (q, 2H); 3.9 (m, 1H); 3.75 (s, 3H); 3.31 (m, 2H); 2.89–2.30 (m, 10H); 2.0 (m, 2H); 1.7 (m, 1H).

IR (mull): $v_{max}$ 3250, 3190, 1580, 1475, 1425, 1370 cm$^{-1}$.

Analysis: Calcd for C$_{14}$H$_{17}$NO: C, 77.60; H, 7.92; N, 7.25. Found: C, 77.86; H, 8.73; N, 6.89.

1,2,3,4-Tetrahydro-8-methoxy-N,N-di-2-propynyl-2-naphthalenamine Hydrochloride, White Solid: m.p. 182°–183° C.

$^1$HNMR (CDCl$_3$, TMS): 7.11–7.06 (t, 1H); 6.72–6.64 (q, 2H); 3.83 (s, 3H); 3.68 (s, 4H); 3.1–3.0 (m, 1H); 2.9–2.8 (m, 3H); 2.53–2.44 (m, 1H); 2.24–2.17 (m, 3H); 1.67–1.57 (m, 1H).

IR (mull): $v_{max}$ 3200, 2200, 2050, 1600 and 1450 cm$^{-1}$

Analysis: Calcd for C$_{17}$H$_{19}$NO.HCl: C, 70.46; H, 6.96; N, 4.83. Found: C, 70.33; H, 7.32; N, 5.13.

(±)-Cis and trans-2,6-dimethyl-4-(1,2,3,4-tetrahydro-8-methoxy-2-naphthalenyl)-morpholine to Yield Pure Cis Isomer of the Title Compound as an Oil and Trans Isomer of the Title Compound as a White Solid: m.p. 72–74° C.

Physical Data for Cis Isomer $^1$HNMR (CDCl$_3$, TMS): 7.17 (t, 1H); 6.7–6.6 (q, 2H); 3.82 (s, 3H); 3.7–3.5 (m, 2H); 3.0–2.4 (m, 8H); 2.0 (q, 1H); 1.9 (m, 2H); 1.5 (m, 1H); 1.20 (s, 3H); 1.19 (s, 3H).

IR (mull): $v_{max}$ 1590 and 1480 cm$^1$.

Analysis: Calcd for C$_{17}$H$_{25}$NO$_2$: C, 74.145; H, 9.15; N, 5.087. Found: C, 73.17; H, 9.17; N, 5.10.

Physical Data for Trans Isomer $^1$HNMR (CDCl$_3$, TMS): 7.14 (t, 1H); 65.66–6.64 (q, 2H); 3.83 (s, 3H); 3.76 –3.68 (m, 2H); 3.06–3.01 (q, 1H); 2.93–2.78 (m, 4H); 2.66–2.61 (m, 1H); 2.502.44 (q, 1H); 2.18–2.09 (m, 1H); 2.08–2.03 (m, 2H); 1.58–1.45 (m, 1H); 1.22 (s, 3H); 1.21 (s, 3H).

IR (mull): $v_{max}$ 1603, 1590 and 1480 cm$^{-1}$.

Analysis: Calcd for C$_{17}$H$_{25}$NO$_2$: C, 74.145; H, 9.15; N, 5.087. Found: C, 73.94; H, 9.30; N, 5.04.

8-Chloro-6-phenyl-N-(1,2,3,4-tetrahydro-8-methoxy-2-naphtha-lenyl)-4H-[1,2,4]triazolo[4,3-a][1,4] benzodiazepine-1-methanamine Off-white Solid: m.p. 138–150° C.

$^1$HNMR (CDCl$_3$, TMS): 7.61–7.38 (m, 5H); 7.09 (t, 1H); 6.66 (q, 2H); 5.53–5.48 (d, 1H); 4.13–4.06 (m, 1H); 3.80–3.70 (m, 3H); 3.4–3.2 (m, 2H); 3.1–2.7 (m, 5H); 2.4 (m, 1, H); 2.0 (m, 4H); 1.7 (m, 1H).

IR (mull): $v_{max}$ 2900, 2640, 1600, 1590, 1490 and 1460 cm$^1$.

Analysis: Calcd for C$_{28}$H$_{26}$N$_5$OCl: C, 69.49; H, 5.41; N, 14.47. Found: C, 68.71; H, 5.82; N, 13.92.

EXAMPLE 16

(±)-7-(1-Ethylpropylamino-5,6,7,8-tetrahydro-1-naphthalenol Hydrochloride (C-3, Chart C)

A solution of 1.0 g (3.5 mmol) N-(1-ethylpropyl)-1,2,3,4-tetrahydro-8-methoxy-2-naphthalenamine hydrochloride and 20 ml 48% HBr were heated to 110° C. The solution was allowed to reflux for 24 hours. When reaction was complete by TLC, 20% NaOH and H$_2$O were added to a pH 13. The mixture was extracted with EtOAc (3×400 mL) and the combined organic layers washed with brine, dried (MgSO$_4$) filtered and concentrated to yield product. The HCl salt was formed by using a MeOH/HCl solution. The title compound was recovered as a white solid by recrystallization using EtOAc/MeOH (0.85 g, 91%): m.p. 268° C.

$^1$HNMR (CDCl$_3$, TMS): 7.10 (t, 1H); 6.65 (t, 1H); 3.5–3.37 (m, 3H); 3.36–3.2 (m, 2H); 3.1–2.9 (m, 2H); 2.7 (q, 1H); 2.35 (m, 1H); 1.83 (m, 4H); 1.08–1.03 (m, 6H).

IR (mull): $v_{max}$ 3206, 1584, 1466 cm$^{-1}$.

Analysis: Calcd for $C_{15}H_{23}NO.HCl$: C, 66.77; H, 8.966; N, 5.19. Found: C, 66.32; H, 8.72; N, 5.37.

(±)-Trans-7-(3,5-dimethyl-1-piperidinyl)-5,6,7,8-tetrahydro-1-naphthalenol Hydrochloride (0.62 g, 65%): m.p. 273–276° C.

$^1$HNMR (CDCl$_3$, TMS): 6.96 (t, 1H); 6.62–6.59 (d, 2H); 3.6–2.7 (m, 8H); 2.3–1.7 (m, 6H); 1.24 (s, 3H); 1.033 (s, 3H).

IR (mull): $v_{max}$ 3328, 3047, 2816, 1629, 1488, 1460, and 1440 cm$^{-1}$.

Analysis: Calcd for $C_{17}H_{25}NO.HCl$: C, 69.02; H, 8.859; N, 4.735. Found: C, 66.15; H, 8.43; N, 4.82.

(±)-Cis-7-(3,5-dimethyl-1-piperidinyl)-5,6,7,8-tetra-hydro-1-naphthalenol Hydrochloride (0.63 g, 67%): m.p. 292–295° C.

$^1$HNMR (CDCl$_3$, TMS): 6.96(t, 1H); 6.67–6.57 (d, 2H); 3.6–2.7 (m, 8H); 2.2–1.7 (m, 6H); 1.22 (s, 3H); 1.10 (s, 3H).

IR (mull): $v_{max}$ 3093, 3014, 2551, 1590, and 1433 cm$^{-1}$.

Analysis: Calcd for $C_{17}N25O.HCl$: C, 69.02; H, 8.859; N, 4.735. Found: C, 68.58; H, 8.97; N, 4.69.

EXAMPLE 17

(±)-7-(Hexahydro-1(2H)-azocinyl)-5,6,7,8-tetrahydro-1-naphthalenol hydrochloride (C-3, Chart C)

A solution of 1 g (3.4 mmol) (±)-hexahydro-1-(1,2,3,4-tetrahydro8-methoxy-2-naphthalenyl)-H-azepine hydrochloride and 20 ml 48% HBr were heated to 110° C. The solution was allowed to reflux for 24 hours. When reaction was complete by TLC, 20% NaOH and H$_2$O were added to a pH 13. The mixture was extracted with EtOAc (3×400 mL) and the combined organic layers washed with brine, dried (MgSO$_4$) filtered and concentrated to yield product. The HCl salt was formed by using a MeOH/HCl solution. The title compound was recovered as a white solid by recrystallization using EtOAc/MeOH (0.73 g, 77%): m.p. 211–213° C.

$^1$HNMR (CDCl$_3$, TMS): 6.96 (t, 1H); 6.59 (d, 2H); 3.67 (m, 1H); 3.44 (m, 4H); 3.30 (t, 3H); 2.94 (m, 2H); 2.75 (q, 1H); 2.30 (m, 1H); 1.98–1.77 (m, 9H).

IR (mull): $v_{max}$ 3127, 2953, 2855, 2615, 2563, 1591, 1467 cm$^{-1}$.

Analysis: Calcd for $C_{16}H_{23}{}^{N}O.HCl$: C, 68.19; H, 8.58; N, 4.97. Found: C, 67.98; H, 8.80; N, 4.97.

EXAMPLE 18

(±)-α-Methyl-N-(1,2,3,4-tetrahydro-8-methoxy-2-naphthalenyl)-1,3-benzodioxole-5-ethanamine Hydrochloride To a solution of 1 g (5.6 mmol) 8-methoxy aminotetralin and 4.2 mL (28 mmol) (3,4-(methylenedioxy)phenyl)2-propanone in 30 mL MeOH/THF (1:1) was added HOAc dropwise to adjust the pH to 4–5. The reaction mixture stirred for 15 minutes under N$_2$, then 0.7 g (11.2 mmol) NaCNBH$_3$ was added. When the reaction was complete by TLC 1 N NaOH (20 mL) and H$_2$O (200 mL) were added to quench the reaction. The solution was extracted with CH$_2$Cl$_2$ (2×500 mL) and the combined organic layers were washed with brine, dried (MgSO$_4$), filtered and concentrated in vacuo. The resulting was purified by liquid chromatography on 400 g of silica gel 60 (230–400m), eluting with hexane/acetone (4:1). Fractions homogeneous by TLC were combined and concentrated in vacuo to give pure compound as an oil. The HCl salt was formed by using a MeOH/HCl solution. The title compound was recovered as a white solid by recrystallization using EtOAc/MeOH (1.27 g, 60%): m.p. 245–254° C.

$^1$HNMR (CDCl$_3$, TMS): 7.4–7.35 (m, 1H); 7.2–7.1 (m, 1H); 6.8–6.73 (m, 4H); 5.96 (s, 2H); 4.0–3.5 (m, 7H); 3.83 (s, 3H); 3.37 (s, 1H); 3.0–2.4 (m, 3H); 2.19 (s, 3H); 1.34 (s, 3H).

IR (mull): $v_{max}$ 2792, 2707, 2461, 1586, 1490, 1440, 1254 cm$^{-1}$.

Analysis: Calcd for $C_{21}H_{25}NO_5.HCl$: C, 67.102; H, 6.972; N, 3.727. Found: C, 67.31; H, 6.98; N, 3.84.

EXAMPLE 19

(±)-7-(Cyclopropylmethyl)amino-5,6,7,8-tetrahydro-1-naphthalenol Hydrochloride (C-3, Chart C)

A 100 mL dried round bottom flask equipped with a reflux condenser was charged with 7.52 ml (43.2 mmol) diphenylphosphine and THF in an N$_2$ atmosphere. To this colorless solution, 27 ml (43.2 mmol) N-butyl lithium was added. The solution became red and was allowed to stir for 10 minutes. 2.5 g (10.8 mmol) (±)-N-(cyclopropylmethyl)-1,2,3,4-tetrahydro-8-methoxy-2-naphthalenamine in 10 mL THF was added and the mixture heated to reflux (70° C.) for 30 hours. Water was added to quench the reaction and extracted with EtOAc (2×500+2×250 mL). The combined organic layers were washed with brine, dried (MgSO$_4$), filtered and evaporated in vacuo to yield an oil. The resulting oil was purified by liquid chromatography on 400 g of silica gel 60 (230–400 m), eluting with hexane/acetone (4:1–2:1). Fractions homogeneous by TLC were combined and concentrated in vacuo to give pure compound as an oil. The HCl salt was formed by using a MeOH/HCl solution. The title compound was recovered as a white solid by recrystallization using EtOAc/MeOH (1.43 g, 52%): m.p. 240–244° C.

$^1$HNMR (MeOH, TMS): (shifted 0.17 ppm) 6.76 (t, 1H); 6.42 (d, 2H); 3.17 (m, 1H); 2.95 (dd, 1H); 2.80–2.12 (m, 6H); 1.45–1.31 (m, 1H).

IR (mull): $v_{max}$ 3217, 2443, 1591, 1452, 1274 cm$^{-1}$.

Analysis: Calcd for $C_{14}H_{19}NO.HCl$: C, 66.40; H, 7.51; N, 5.53. Found: C, 65.11; H, 7.84; N, 5.48.

5,6,7,8-tetrahydro-7-(2-propenyl)amino-1-naphthalenol Hydrochloride (1.4 g, 67%): m.p. 241–242° C.

IR (mull): $v_{max}$ 3210, 2960, 2449, 2411 cm$^{-1}$.

Analysis: Calcd for $C_{13}H_{17}NO.HCl$: C, 65.129; H, 7.568; N, 5.843. Found: C, 65.28; H, 7.67; N, 5.93.

EXAMPLE 20

(±)-7-(Di-2-propenylamino)-5,6,7,8-tetrahydro-1-naphthalenol Hydrochloride (C-3, Chart C)

Synthesized using the above procedure (m.p. 173–175°)

$^1$HNMR (CDCl$_3$, TMS): 6.98 (t, 1H); 6.64 (q, 2H); 5.98–5.85 (m, 2H); 5.26–5.12 (m, 4H); 3.30–3.26 (m, 4H); 3.12 (m, 1H); 2.97–2.50 (m, 3H); 2.35 (m, 1H); 2.05 (m, 1H); 1.63 (m, 1H).

IR (mull): $v_{max}$ 3318, 3092, 2955, 2868, 1590, 1466, 1458 cm$^{-1}$.

Analysis: Calcd for $C_{16}H_{21}NO.HCl$: C, 68.68; H, 7.926; N, 5.00. Found: C, 68.21; H, 8.17; N, 5.14.

EXAMPLE 21

(±)-1,2,3,4-Tetrahydro-N-2(m-trifluoromethyl)benzyl-2-naphthalenamine Hydrochloride (C-2, Chart C)

To a solution of 1.4 g (10 mmol) β-tetralone and 7.16 mL (50 mmol) m-trifluoromethylbenzylamine in 30 mL MeOH/THF (1:1) was added HOAc dropwise to adjust the pH to 4–5. The reaction mixture stirred for 15 minutes under N$_2$, then 1.26 g (20 mmol) NaCNBH$_3$ was added. When the reaction was complete by TLC (24 h), 1 N NaOH (20 mL) and H$_2$O (200 mL) was added to quench the reaction. The solution was extracted with CH$_2$Cl$_2$ (3×500 mL) and the combined organic layers were washed with brine, dried (MgSO$_4$), filtered and concentrated in vacuo. The resulting yellow/black oil was purified by liquid chromatography on 400 g of silica gel 60 (230–400m), eluting with hexane/ethyl acetate (4:1). Fractions homogeneous by TLC were combined and concentrated in vacuo to give pure compound as a yellow oil. The HCl salt was formed by using a MeOH/HCl solution. The tide compound was recovered as a white solid by recrystallization using EtOAc/MeOH (2.71 g, 74%): m.p. 231–233° C.

$^1$HNMR (CDCl$_3$, TMS): 7.97–7.94 (m, 2H); 7.69–7.59 (m, 2H); 7.16–7.09 (m, 4H); 4.31 (m, 2H); 3.37–2.96 (m, 6H); 2.5 (m, 1H); 2.15 (m, 1H).

IR (mull): $v_{max}$ 2951, 2853, 2784, 2591, 2509, 1597, 1498, 1452, 1376, 1259, 1233 cm$^{-1}$.

Analysis: Calcd for C$_{18}$H$_{18}$NF$_3$.HCl: C, 63.25; H, 5.60; N, 4.098. Found: C, 63.00; H, 5.89; N, 3.99.

(±)-1,2,3,4-tetrahydro-N-2-benzyl-2-naphthalenamine Hydrochloride White Solid; m.p. 244°–246° C.

$^1$HNMR (CDCl$_3$, TMS):7.64 (m, 2H); 7.41–7.36 (m, 3H); 7.13–7.05 (m, 4H); 4.18–4.15 (m, 2H); 3.23 (m, 3H); 2.89 (m, 1H); 2.76 (m, 1H); 2.42 (m, 1H); 2.15 (m, 2H);

IR (mull): $v_{max}$ 3063, 3045, 2607, 2574, 2505, 2452, 2430, 1591, 1497, 1458, 1355 cm$^{-1}$.

Analysis: Calcd for C$_{17}$H$_{19}$N.HCl: C, 74.57; H, 7.36; N, 5.11. Found: C, 74.80; H, 7.19; N, 5.12.

(±)-N-(cyclopropylmethyl)-1,2,3,4-tetrahydro-2-naphthalenamine Hydrochloride White solid: m.p. 231–°233° C.

$^1$HNMR (CDCl$_3$, TMS): 7.16–7.09 (m, 4H); 3.57–1.94 (m, 8H); 1.28–0.44 (m, 5H).

IR (mull): $v_{max}$ 1716, 1613, 1596, 1583 cm$^{-1}$.

Analysis: Calcd for C$_{14}$H$_{19}$N.HCl: C, 70.72; H, 8.68; N, 5.89. Found: C, 70.63; H, 8.38; N, 6.04.

(±)-1,2,3,4-Tetrahydro-N-propyl-2-naphthalenamine Hydrochloride White Solid: 244–°246° C.

$^1$HNMR (CDCl$_3$, TMS): 7.16–7.12 (m, 4H); 3.52–1.84 (m, 11H); 1.05 (t, 3H).

IR (mull): $v_{max}$ 1609, 1593 cm$^{-1}$.

Analysis: Calcd for C$^1{}_3$H$_{19}$N.HCl: C, 69.16; H, 8.93; N, 6.20. Found: C, 69.10; H, 9.22; N, 6.25.

(±)-1,2,3,4-Tetrahydro-N-2-propynyl-2-naphthalenamine Hydrochloride White Solid: 255°–257° C.

$^1$HNMR (CDCl$_3$, TMS): 7.19–7.06 (m, 4H); 3.98–3.97 (d, 2H); 3.72–1.92 (m, 11H).

IR (mull): $v_{max}$ 1605, 1587 cm$^{-1}$.

Analysis: Calcd for C$_{13}$H$_{15}$N.HCl: C, 70.42; H, 7.27; N, 6.32. Found: C, 70.37; H, 7.48; N, 6.41.

(±)-1,2,3,4-Tetrahydro-N,N-di-2-propenyl-2-naphthalenamine Hydrochloride White Solid: m.p. 138°–139° C.

$^1$HNMR (CDCl$_3$, TMS): 7.18–7.12 (m, 4H); 6.41–5.46 (m, 6H); 3.81–1.71 (m).

IR (mull): $v_{max}$ 2426, 1605, 1585 cm$^{-1}$.

Analysis: Calcd for C$_{16}$H$_{21}$N.HCl: C, 72.85; H, 8.41; N, 5.31. Found: C, 72.76; H, 8.49; N, 5.37.

(±)-1,2,3,4-tetrahydro-N-2-propenyl-2-naphthalenamine Hydrochloride White Solid: m.p. 235°–237° C.

$^1$HNMR (CDCl$_3$, TMS): 7.07 (m, 4H); 6.00–5.87 (m, 1H); 5.23–5.07 (q, 2H); 3.36 (d, 2H); 3.02–2.57 (m, 5H); 2.06 (m, 1H); 1.61 (m, 1H); 1.35 (m, 1H).

IR (mull): $v_{max}$ 2444, 1648, 1609, 1591, 1497, 1462, 1442, and 1424 cm$^{-1}$.

Analysis: Calcd for C$_{13}$H$_{17}$N.HCl: C, 69.786; H, 8.109; N, 6.261. Found: C, 69.82; H, 8.11; N, 6.32.

EXAMPLE 22

(±)-N-(cyclopropylmethyl)-1,2,3,4-tetrahydro-8-methoxy-2-naphthalenamine Hydrochloride White Solid To a solution of 2.64 g (15 mmol) 8-methoxy tetralone, 6 g (60 mmol) methyl-cyclopropylamine.HCl and 4.92 g (60 mmol) NaOAc in 30 mL MeOH/THF (1:1) was added HOAc dropwise to adjust the pH to 4–5. The reaction mixture stirred for 15 minutes under N$_2$, then 1.26 g (20 mmol) NaCNBH$_3$ was added. When the reaction was complete by TLC (24h), 1 N NaOH (20 mL) and H$_2$O (200 mL) was added to quench the reaction. The solution was extracted with CH$_2$Cl$_2$ (2×500 mL) and the combined organic layers were washed with brine, dried (MgSO$_4$), filtered and concentrated in vacuo. The resulting oil was purified by liquid chromatography on 400 g of silica gel 60 (230–400 m), eluting with hexane/acetone (3:1). Fractions homogeneous by TLC were combined and concentrated in vacuo to give pure compound as an oil. The HCl salt was formed by using a MeOH/HCl solution. The title compound was recovered by recrystallization as a white solid using EtOAc/MeOH (1.77 g, 44%); m.p. 216–218° C.

$^1$HNMR (CDCl$_3$, TMS): 7.11 (t, 1H); 6.67 (q, 2H); 3.77 (s, 3H); 3.5–3.3 (m, 2H); 3.02 (m, 2H); 2.89 (m, 3H); 2.58 (m, 1H); 2.1 (m, 1H); 1.67 (s, 3H); 1.4 (m, 1H); 0.74 (m, 2H); 0.50 (m, 2H).

IR (mull): $v_{max}$ 3076, 2785, 2738, 2433, 1603, 1586, 1472, and 1257 cm$^{-1}$.

Analysis: Calcd for C$_{15}$H$_{21}$NO.HCl: C, 67.277; H, 8.281; N, 5.231. Found: C, 66.94; H, 8.43; N, 5.24.

EXAMPLE 23

1,2,3,4-Tetrahydro-8-methoxy-N,N-bis(2-methoxyethyl)-2-naphthalenamine (C-2, Chart C)

A solution of 1.76 g (10 mmol) 8-methoxy tetralone, 2.66 g (20 mmol) N,N-bis(-2-methoxyethyl)amine, and 25 mg p-toluenesulfonic acid in toluene was heated to reflux under a N$_2$ atmosphere. The flask was equipped with a Dean-Stark trap to collect H$_2$O. TLC analysis was used to monitor the reaction. After 48 hours, the solvent was removed in vacuo. The crude ene-amine was hydrogenated using 450 mg 10% pd/C in 50 mL MeOH at 50 psi H$_2$ for 24 hours. The reaction mixture was filtered over celite and the filtrate purified by liquid chromatography on 400 g of silica gel-60 (230–400 mesh), eluting with hexane/ethyl acetate/isopropanol (10:5:1). Fractions homogeneous by TLC were combined and concentrated in vacuo to give pure title compound as a yellow oil (2.3 g, 80%).

$^1$H NMR (CDCl$_3$,TMS): 7.10–7.04 (t, 1H); 6.70–6.63 (q, 2H); 3.80 (s, 3H); 3.43 (t, 4H); 3.35 (s, 6H); 3.01–2.79 (m, 8H); 2.38 (m, 1H); 2.02 (m, 1H); 1.64–1.55 (m, 1H).

IR (mull): $v_{max}$ 3000, 2950, 1590 and 1460 cm$^{-1}$.

Analysis: Calcd for C$_{17}$H$_{27}$NO$_3$: C, 69.59; H, 9.28; N, 4.77. Found: C, 69.64; H, 9.14; N, 5.34.

EXAMPLE 24

Cis-(±)-1,2,3,4-tetrahydro-1-(2-propenyl)-N-propyl-2-naphthalenamine Hydrochloride and trans-(±)-1,2,3,4-tetrahydro-1-(2-propenyl)-N-propyl-2-naphthalenamine Hydrochloride (E-3, Chart E)

To a solution of 9.31 g (50 mmol) 1,2,3,4-tetrahydro-1-(2-propenyl)-2-oxo-naphthalene and 20.6 mL (250 mmol) allylamine in 60 mL MeOH/THF (1:1) was added HOAc (about 32 mL) dropwise at 0–5° C. to adjust the pH to 4–5 under the nitrogen atmosphere. The reaction mixture was stirred for thirty minutes then 6.3 g (100 mmol) of sodium cyanoborohydride was added. The reaction was monitored by TLC analysis. After the reaction mixture was stirred at room temperature for 24 hours, the reaction was quenched with 20% sodium hydroxide until pH>13. The solution was extracted with methylene chloride (2×1 L). The combined organic layers were washed with brine, dried (MgSO$_4$), filtered and concentrated in vacuo. The resulting oil was purified by liquid chromatography on 800 g of silica gel 60 (230–400 m), eluting with hexane/acetone (4:1), and collecting 40 mL fractions. Fractions homogeneous by TLC were combined and concentrated in vacuo to give 7.9 g (69%) of the mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (4.7 g) was assigned as pure cis isomer. The mother liquor was free-based by treatment with saturated sodium bicarbonate to pH>8 and extracted with methylene chloride. The resulting oil was purified by liquid chromatography on 800 g silica gel 60 (230–400 m), eluting with hexane/ethyl acetate/methanol (40:10:1) and collecting 40 mL fractions. Fractions 50–61 afforded additional 1.6 g of pure cis isomer of the title compound after converting to HCl-salt and recrystallizing from ethyl acetate/methanol. Thus, 6.3 g of pure cis isomer of the title compound was isolated: m.p. 150–151° C. Fractions 62–84 gave 1.1 g of an oil which gave 1 g of pure trans isomer of the title compound as a white solid after converting to HCl-salt and recrystallizing from ethyl acetate/hexane: m.p. 186–187° C. Physical data for cis isomer:

$^1$HNMR (CDCl$_3$, TMS): 7.23–7.02 (m, 4H); 5.94–4.96 (m, 3H); 3.53–1.60 (m, 13H); 1.02 (t, J=7 Hz, 3H).

IR (mull): $v_{max}$ 1641 and 1590 cm$^{-1}$.

Analysis: Calcd for C$_{16}$H23N.HCl: C, 72.29; H, 9.10; N, 5.27. Found: C, 72.09; H, 9.16; N, 5.32.

Physical Data For Trans Isomer $^1$HNMR (CDCl$_3$, TMS): 7.15–7.12 (m, 4H); 5.69–5.07 (m, 3H); 3.50–1.64 (m, 13H); 0.95 (t, J=7 Hz, 3H).

IR (mull): $v_{max}$ 1641 and 1592 cm$^{-1}$.

Analysis: Calcd for C$_{16}$H$_{23}$N.HCl: C, 72.29; H, 9.10; N, 5.27. Found: C, 72.04; H, 9.07; N, 5.29.

Cis-(±)-1,2,3,4-Tetrahydro-N,1-di-(2-propenyl)-2-naphthalenamine Hydrochloride, White Solid: m.p. 1381°–139° C. and trans-(±)-1,2,3,4-tetrahydro-N,1-di-(2-propenyl)-n-propyl-2-naphtha-lenamine Hydrochloride, White Solid: 151°–153° C.

Physical Data For Cis Isomer $^1$HNMR (CDCl$_3$, TMS): 7.23–7.01 (m, 4H); 6.28–5.03 (m, 6H); 3.82–1.65 (m, 11H).

IR (mull): $v_{max}$ 1641 and 1589 cm$^{-1}$.

Analysis: Calcd for C$_{16}$H$_{21}$N.HCl: C, 72.85; H, 8.41; N, 5.31. Found: C, 72.86; H, 8.42; N, 5.27.

Physical Data For Trans Isomer $^1$HNMR (CDCl$_3$, TMS): 7.17–7.11 (m, 4H); 6.14–5.04 (m, 6H); 3.62–1.64 (m, 11H).

IR (mull): $v_{max}$ 1641 and 1589 cm$^{-1}$.

MS: Calcd for C$_{16}$H$_{21}$N: 227.1674. Found: 227.1660.

Analysis: Calcd for C$_{16}$H$_{21}$N.HCl: C, 72.85; H, 8.41; N, 5.31. Found: C, 72.91; H, 8.54; N, 5.37.

TLC (Silica Gel GF): Rf=0.32 in hexane-acetone (4:1).

EXAMPLE 25

Cis-(±)-1,2,3,4-tetrahydro-8-methoxy-1-(2-propenyl)-N-propyl-2-naphthalenamine Hydrochloride and trans-(±)-1,2,3,4-tetrahydro-8-methoxy-1-(2-propenyl)-N-propyl-2-naphthalenamine Hydrochloride (E-3, Chart E)

To a solution of 22 g (0.1 mol) 1,2,3,4-tetrahydro-1-(2-propenyl)-8-methoxy-2-oxo-naphthalene and 32.8 mL (0.4 mol) propylamine in 400 mL MeOH/THF (1:1) was added HOAc (about 80 mL) dropwise at 0–5° C. to adjust the pH to 4–5 under the nitrogen atmosphere. The reaction mixture was stirred for thirty minutes, then 12.6 g (0.2 mol) of sodium cyano-borohydride was added. The reaction was monitored by TLC analysis. After the reaction mixture was stirred at room temperature for 48 hours, the reaction was quenched with 20% sodium hydroxide until pH>13. The solution was extracted with ethyl acetate (2×1 L). The combined organic layers were washed with brine, dried (MgSO$_4$), filtered and concentrated in vacuo. The resulting oil was purified by liquid chromatography on 1 Kg of silica gel 60 (230–400 m), eluting with 4 L methylene chloride and 3 L methylene chloride-methanol (19:1), and collecting 40 mL fractions. Fractions 39–56 gave 3.4 g (13%) of the recovered diallyl ketone as a yellow oil. Fractions 58–70 gave 3.3 g (15%) of alcohol (reduction product of 3b, recrystallized from hexane/ethyl acetate, m.p. 75–76° C.). Fractions 72–112 afforded 15.5 g (60%) of a mixture of the desired cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (14 g) was assigned as pure cis isomer of the title compound: m.p. 199–201° C. The mother liquor was free-based by treatment with saturated sodium bicarbonate to pH>8 and extracted with methylene chloride. The resulting oil was purified by liquid chromatography on 600 g silica gel 60 (230–400 m), eluting with methylene chloride-methanol (20:1) and collecting 40 mL fractions. Fractions homogeneous by TLC were combined and concentrated. The resulting oil was converted to HCl-salt and recrystallized from ethyl acetate/hexane to give 2.6 g of the white solid assigned as pure trans isomer of the title compound: m.p. 178–180° C.

Physical Data For Cis Isomer $^1$HNMR (CDCl$_3$, TMS): 7.20–6.62 (m, 3H); 5.98–4.92 (m, 3H); 3.83 (s, 3H); 3.72–1.68 (m, 13H); 1.02 (t, J=7 Hz, 3H).

IR (mull): $v_{max}$ 1638, 1586 and 1567 cm$^{-1}$.

Analysis: Calcd for C$_{17}$H$_{25}$NO.HCl: C, 69.02; H, 8.86; N, 4.74. Found: C, 69.21; H, 8.97; N, 4.82.

Physical Data For Trans Isomer $^1$HNMR (CDCl$_3$, TMS): 7.27–6.68 (m, 3H); 5.32–4.86 (m, 3H); 3.81 (s, 3H); 3.62–1.82 (m, 13H); 0.93 (t, J=7 Hz, 3H).

IR (mull): $v_{max}$ 1640, 1606 and 1583 cm$^{-1}$.

Analysis: Calcd for C$_{17}$H$_{25}$NO.HCl: C, 69.02; H, 8.86; N, 4.74. Found: C, 68.25; H, 8.86; N, 4.86.

EXAMPLE 26

Cis-(±)-1,2,3,4-Tetrahydro-8-methoxy-N,1-di-(2-propenyl)-2-naphthalenamine Hydrochloride and trans-(±)-1,2,3,4-tetrahydro-8-methoxy-N,1-di-(2-propenyl)-2-naphthalenamine Hydrochloride (E-3, Chart E)

To a solution of 9 g (40 mmol) 1,2,3,4-tetrahydro-1-(2-propenyl)-8-methoxy-2-oxo-naphthalene (crude product obtained from alkylation) and 12 mL (160 mmol) allylamine in 160 mL MeOH/THF (1:1) was added HOAc (about 32 mL) dropwise at 0–5° C. to adjust the pH to 4–5 under the nitrogen atmosphere. The reaction mixture was stirred for thirty minutes then 5.0 g (80 mmol) of sodium cyanoborohydride was added. The reaction was monitored by TLC analysis. After the reaction mixture was stirred at room temperature for 48 hours, the reaction was quenched with 20% sodium hydroxide until pH>13. The solution was extracted with ethyl acetate (2×1 L). The combined organic layers were washed with brine, dried (MgSO$_4$), filtered and concentrated in vacuo. The resulting oil was purified by liquid chromatography on 800 g of silica gel 60 (230–400 m), eluting with 2 L methylene chloride and 4 L methylene chloride (20:1), and collecting 40 mL fractions. Fractions 105–106 gave 0.42 g (4.8%) of the alcohol. Fractions 107–122 afforded 8.56 g (83%) of the mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (6.15 g) was assigned as pure cis isomer, m.p. 187–188° C. The mother liquor was free-based by treatment with saturated sodium bicarbonate to pH>8 and extracted with methylene chloride. The resulting oil was purified by liquid chromatography on 800 g silica gel 60 (230–400 m), eluting with hexane/ethyl acetate/methanol (20: 10: 1), and collecting 40 mL fractions. Fractions 57–74 afforded a yellow oil which was converted to HCl-salt and recrystallized from ethyl acetate/hexane. The white solid thus isolated (1.2 g) was assigned as pure cis isomer, m.p. 143–144° C.

Physical Data For Cis Isomer $^1$HNMR (CDCl$_3$, TMS): 7.16–6.67 (m, 4H); 6.72–4.93 (m, 6H); 3.80 (s, 3H); 3.95– 164 (m, 11H).

IR (mull): $v_{max}$ 1601 and 1585 cm$^{-1}$.

Analysis: Calcd for C$_{17}$H$_{23}$NO.HCl: C, 69.49; H, 8.23; N, 4.77. Found: C, 69.41; H, 8.52; N, 4,79.

Physical Data For Trans Isomer $^1$HNMR (CDCl$_3$, TMS): 7.18–6.65 (m, 4H); 6.18–4.92 (m, 6H); 3.79 (s, 3H); 3.58–1.67 (m, 11H).

IR (mull): $v_{max}$ 1595 and 1587 cm$^{-1}$.

Analysis: Calcd for C$_{17}$H$_{23}$NO.HCl: C, 69.49; H, 8.23; N, 4.77. Found: C, 69.38; H, 8.48; N, 4.57.

EXAMPLE 27

Cis-(±)-1,2,3,4-tetrahydro-8-methoxy-1-(cyclopropylmethyl)-N-propyl-2-naphthalenamine Hydrochloride and trans-(±)-1,2,3,4-tetrahydro-8-methoxy-1-(cyclopropylmethyl)-N-propyl-2-naphthalenamine Hydrochloride (E-3, Chart E)

To a solution of 3.52 g (20 mmol) 1,2,3,4-tetrahydro-(cyclo-propylmethy)-2-oxo-naphthalene and 6.6 mL (80 mmol) n-propylamine in 80 mL MeOH/THF (1:1) was added HOAc (about 16 mL) dropwise at 0–5° C. to adjust the pH to 4–5 under the nitrogen atmosphere. The reaction mixture was stirred for thirty minutes then 2.5 g (40 mmol) of sodium cyanoborohydride was added. The reaction was monitored by TLC analysis. After the reaction ixture was stirred at room temperature for 48 hours, the reaction was quenched with 20% sodium hydroxide until pH>13. The solution was extracted with ethyl acetate (2×1 L). The combined organic layers were washed with brine, dried (MgSO$_4$), filtered and concentrated in vacuo. The resulting oil was purified by liquid chromatography on 800 g of silica gel 60 (230–400 m), eluting with methylene chloride-methanol (20:1), and collecting 40 mL fractions. Fractions 44–56 gave 0.6 g of the alcohol. Fractions 57–105 gave 4.3 g (78%) of a mixture of mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (3.2 g) was assigned as pure cis isomer of the title compound, 229–230° C. The mother liquor was concentrated in vacuo and recrystallized from hexane/-acetone to give a white solid (0.58 g), assigned as pure trans isomer of the title compound, m.p. 136–140° C.

Physical Data For Cis Isomer $^1$HNMR (CDCl$_3$, TMS): 7.17–6.66 (m, 3H); 3.80 (s, 3H); 3.88–1.26 (m, 13H); 1.04 (t, J=7 Hz, 3H); 1.02–0.00 (m, 5H).

IR (mull): $v_{max}$ 1600 and 1585 cm$^{-1}$.

Analysis: Calcd for C$_{18}$H$_{27}$NO.HCl: C, 69.77; H, 9.11; N, 4.52. Found: C, 69.53; H, 9.35; N, 4.61.

Physical Data For Trans Isomer $^1$HNMR (CDCl$_3$, TMS): 7.27–6.66 (m, 3H); 3.79 (s, 3H); 3.92–1.30 (m, 13H); 0.95 (t, J=7 Hz, 3H); 0.80–0.000 (m, 5H).

IR (mull): $v_{max}$ 1601 and 1587 cm$^{-1}$.

Analysis: Calcd for C$_{18}$H$_{27}$NO.HCl: C, 69.77; H, 9.11; N, 4.52. Found: C, 69.45; H, 9.17; N, 4.62.

EXAMPLE 28

Cis-(±)-1,2,3,4-Tetrahydro-8-methoxyl-1-(cyclopropylmethyl)-N-(2-propenyl)-2-naphthalenamine Hydrochloride and trans-(±)-1,2,3,4-tetrahydro-8-methoxy-1-(cyclopropylmethyl)-N-(2-propenyl)-2-naphthalenamine Hydrochloride (E-3, Chart E)

To a solution of 3.52 g (20 mmol) 1,2,3,4-tetrahydro-1-cyclo-propylmethyl)-8-methoxy-2-oxo-naphthalene and 6.0 mL (80 mmol) allylamine in 80 mL MeOH/THF (1:1) was added HOAc (about 16 mL) dropwise at 0–5° C. to adjust the pH to 4–5 under the nitrogen atmosphere. The reaction mixture was stirred for thirty minutes, then 2.5 g (40 mmol) of sodium cyanoborohydride was added. The reaction was monitored by TLC analysis. After the reaction mixture was stirred at room temperature for 48 hours, the reaction was quenched with 20% sodium hydroxide until pH>13. The solution was extracted with ethyl acetate (2×1 L). The combined organic layers were washed with brine, dried (MgSO$_4$), filtered, and concentrated in vacuo. The resulting oil was purified by liquid chromatography on 800 g of silica gel 60 (230–400 m), eluting with methylene chloride-methanol (20:1) and collecting 40 mL fractions. Fractions 31–77 afforded 4.83 g (89%) of a mixture of cis and trans isomers as a yellow oil. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (3.35 g) was assigned as pure cis isomer of the title compound, m.p. 214–215° C. The mother liquor was concentrated in vacuo and recrystallized from hexane/ethyl acetate to give 0.8 g of a white solid which was assigned as pure trans isomer of the title compound, m.p. 146–148° C.

Physical Data For Cis Isomer $^1$HNMR (CDCl$_3$, TMS): 7.18–6.6 4(m, 3H); 6.30–5.41 (m, 3H); 3.78 (m, 3H); 3.98–1.25 (m, 11H); 0.92–0.00 (m, 5H).

IR (mull): $v_{max}$ 1600 and 1585 cm$^{-1}$.

Analysis: Calcd for C$_{18}$H$_{25}$NO.HCl: C, 70.23; H, 8.51; N, 4.55. Found: C, 70.23: H, 8.70; N, 4.59.

Physical Data For Trans Isomer $^1$HNMR (CDCl$_3$, TMS): 7.26–7.09 (m, 3H); 6.73–5.46 (m, 3H); 3.79 (s, 3H); 3.92–1.22 (m, 11H); 0.92–0.00 (m, 5H).

IR (mull): $v_{max}$ 1604 and 1585 cm$^{-1}$.

Analysis: Calcd for C$_{18}$H$_{25}$NO.HCl: C, 70.23; H, 8.51; N, 4.55. Found: C, 69.97; H, 8.86; N, 4.64.

EXAMPLE 29

Cis-(±)-1,2,3,4-Tetrahydro-8-methoxy-N,1-di-(cyclopropylmethyl)-2-naphthalenamine Hydrochloride and trans- (±)-1,2,3,4-tetrahydro-8-methoxy-N,1-di-(cyclopropylmethyl)-2-naphthalenamine Hydrochloride (E-3, Chart E)

To a solution of 3.52 g (20 mmol) 1,2,3,4-tetrahydro-1-(cyclo-propylmethy)-8-methoxy-2-oxo-naphthalene and 8.6 g (80 mmol) cyclopropylmethylamine hydrochloride, and 6.6 g (80 mmol) sodium acetate monohydrate in 100 mL MeOH/THF (1:1) was added HOAc (about 16 mL) dropwise at 0–5° C. to adjust the pH to 4–5 under the nitrogen atmosphere. The reaction mixture was stirred for thirty minutes, then 2.51 g (40 mmol) of sodium cyanoborohydride was added. The reaction was monitored by TLC analysis. After the reaction mixture was stirred at room temperature for four days, the reaction was quenched with 20% sodium hydroxide until pH>13 and THF/MeOH was removed in vacuo. The concentrate was treated with 600 mL of ethyl acetate. The organic layer was extracted with 3N hydrochloric acid (2×100 mL), thus transferring the basic organic compounds into the aqueous layer and leaving the neutral and acidic compounds in the organic layer. After this organic layer was dried over anhydrous magnesium sulfate and concentrated in vacuo, there was isolated about 1.54 g (43%) of alcohol. Then the aqueous layer containing the desired products was basified by adding 20% sodium hydroxide, and was extracted with ethyl acetate (2×1 L). The combined organic layers were washed with brine, dried (MgSO$_4$), filtered and concentrated in vacuo. The resulting oil was purified by liquid chromatography on 400 g of silica gel 60 (230–400 m), eluting with hexane/acetone (4:1), and collecting 40 mL fractions. Fractions 32–70 afforded 2.3 g (40%) of the mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at –20° C.). The white solid isolated (1.63 g) was assigned as pure cis isomer of the title compound, m.p. 218–219° C. The mother liquor was free-based by treatment with saturated sodium bicarbonate to pH>8 and extracted with methylene chloride. The resulting oil was purified by liquid chromatography on 400 g silica gel 60 (230–400 m), eluting with hexane-acetone (4:1), and collecting 40 mL fractions. Fractions homogeneous by TLC were combined and concentrated to give a yellow oil which gave 0.45 g of pure tran isomer of the title compound as a white solid after converting to HCl-salt and recrystallizing from ethyl acetate/hexane: m.p. 149–150° C. (Note).

Physical Data For Cis Isomer $^1$HNMR (CDCl$_3$, TMS): 7.27–6.66 (m, 3H); 3.80 (s, 3H); 3.82–1.32 (m, 11H); 0.92–0.00 (m, 10H).

IR (mull): ν$_{max}$ 1602 and 1584 cm$^{-1}$.

Analysis: Calcd for C$_{19}$H$_{27}$NO.HCl: C, 70.90; H, 8.77; N, 4.35. Found: C, 70.88; H, 98.92 N, 4.52.

Physical Data For Trans Isomer $^1$HNMR (CDCl$_3$, TMS): 7.2–66.67 (m, 3H); 3.80 (s, 3H); 4.10–1.28 (m, 11H); 0.82–0.05 (m, 10H).

IR (mull): ν$_{max}$ 1602 and 1591 cm$^{-1}$.

Analysis: Calcd for C$_{19}$H$_{27}$NO.HCl: C, 70.90; H, 8.77; N, 4.35. Found: C, 70.66; H, 8.64; N, 5.03.

EXAMPLE 30

Cis-(±)-1,2,3,4-Tetrahydro-8-methoxy-1-(2-propenyl)-N-cyclopropylmethyl-2-naphthalenamine Hydrochloride and trans-(±)-1,2,3,4-tetrahydro-8-methoxy-1-(2-propenyl)-N-cyclopropylmethyl-2-naphthalenamine Hydrochloride (E-3, Chart E)

To a solution of 2.6 g (12 mmol) 1,2,3,4-tetrahydro-1-(2-propenyl)-2-oxo-8-methoxy-naphthalene, 5.16 g(48 mmol) cyclopropyl-methylamine hydrochloride, and 3.9 g (48 mmol) sodium acetate monohydrate in 60 mL MeOH/THF (1:1) was added HOAc (about 9.6 mL) dropwise at 0–5° C. to adjust the pH to 4–5 under the nitrogen atmosphere. The reaction mixture was stirred for 30 minutes and 1.5 g (24 mmol) of sodium cyanoborohydride was added. The reaction was monitored by TLC analysis. After the reaction mixture was stirred at room temperature for four days, the reaction was quenched with 20% sodium hydroxide until pH>13 and THF/MeOH was removed in vacuo. The concentrate was treated with 600 mL of ethyl acetate and extracted with 3N HCl (2×100 mL), thus transferring the basic organic compounds into aqueous layer and leaving the neutral and acidic compounds in the organic layer. After this organic layer was dried over anhydrous magnesium sulfate and concentrated in vacuo, there was isolated 0.84 g (32%) of alcohol. Then aqueous layer containing the desired products was basified with 20% sodium hydroxide and extracted with ethyl acetate (2×600 mL). The combined organic layers were washed with brine, dried (MgSO$_4$), filtered and concentrated in vacuo. The resulting oil was purified by liquid chromatography on 400 g of silica gel 60 (230–400 m), eluting with hexane/acetone (4:1), and collecting 40 mL fractions. Fractions 35–70 afforded 1.0 g (30%) of a mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at –20° C.). The white solid isolated (0.67 g) was assigned as pure cis isomer of the title compound, m.p. 186–187° C. The mother liquor was free-based by treatment with saturated sodium bicarbonate to pH>8 and extracted with methylene chloride. The resulting oil was purified by liquid chromatography on 400 g silica gel 60 (230–400 m), eluting with hexane-acetone (4:1) and collecting 40 mL fractions. Fractions 30–70 afforded 0.2 g of pure trans isomer of the title compound as a white solid after converting to HCl-salt and recrystallizing from ethyl acetate/hexane: m.p. 185–186° C.

Physical Data For Cis Isomer $^1$HNMR (CDCl$_3$, TMS): 7.26–6.67 (m, 3H); 5.96–4.92 (m, 3H); 3.80 (s, 3H); 3.78–1.28 (m, 11H); 0.72–0.42 (m, 5H).

IR (mull): ν$_{max}$ 1600 and 1584 cm$^{-1}$.

Analysis: Calcd for C$_{18}$H$_{25}$NO.HCl: C, 70.23; H, 8.51; N, 4.55. Found: C, 69.99; H, 8.63; N, 4.64.

Physical Data For Trans Isomer $^1$HNMR (CDCl$_3$, TMS): 7.26–667 (m, 3H); 6.02–4.92 (m, 3H); 3.80 (s, 3H); 3.92–1.28 (m, 11H); 0.78–0.42 (m, 5H).

IR (mull): ν$_{max}$ 1639 and 1595 cm$^{-1}$.

Analysis: Calcd for C$_{16}$H$_{25}$NO.HCl: C, 70.23; H, 8.51; N, 4.55. Found: C, 69.91; H, 8.57; N, 4.61.

EXAMPLE 31

Cis-(±)-1,2,3,4-Tetrahydro-5-methoxy-1-(2-propenyl)-N-propyl-2-naphthalenamine Hydrochloride and trans-(±)-1,2,3,4-tetra-hydro-5-methoxy-1-(2-propenyl)-N-propyl-2-naphthalenamine Hydrochloride (E-3, Chart E)

To a solution of 0.97 g (15 mmol) 1,2,3,4-tetrahydro-1-(2-pro-penyl)-5-methoxy-2-oxo-naphthalene and 1.8 mL (22.5 mmol) n-propyl-amine in 18 mL MeOH/THF (1:1) was added HOAc dropwise (about 3 mL) at 0–5° C. to adjust the pH to 4–5 under the nitrogen atmosphere. The reaction mixture was stirred for 30 minutes then 0.57 g (9.0 mmol) of sodium cyanoborohydride was added. The reaction was monitored by TLC analysis. After the reaction mixture was stirred at room temperature for 18 hours, the reaction was quenched with 20% sodium hydroxide until pH>13. The solution was extracted with methylene chloride (2×1 L). The combined organic layers were washed with brine, dried (MgSO$_4$), filtered and concentrated in vacuo. The resulting oil was purified by liquid chromatography on 400 g of silica gel 60 (230–400 m), eluting with hexane/ethyl acetate/methanol (40:10:1), and collecting 40 mL fractions. Fractions 32–46 afforded 0.9 g (78%) of light yellow oil, which was treated with excess anhydrous hydrochloric acid/methanol and concentrated in vacuo. The resulting solid was recrystallized from ethyl acetate/methanol to give 0.75 g of a pale yellow solid, assigned as a cis isomer of the title compound, m.p. 183–184° C. Fractions 47–77 afforded 0.1 g of a light yellow oil which was also converted into hydrochloric acid salt as above. Recrystallization from ethyl acetate/hexane gave a white solid, assigned as a trans isomer of the title compound, m.p. 197–198° C.

Physical Data For Cis Isomer $^1$HNMR (CDCl$_3$, TMS): 7.12–6.65 (m, 3H); 5.89–5.02 (m, 3H); 3.82 (s, 3H), 3.40–1.70 (m, 13H); 1.02 (t, J=7 Hz, 3H).

IR (mull): v$_{max}$ 1641 and 1586 cm$^{-1}$.

MS: Calcd for C$_{17}$H$_{25}$NO: 259.1936. Found: 259.1959.

Analysis: Calcd for C$_{17}$H$_{25}$NO.HCl: C, 69.02; H, 8.86; N, 4.74. Found: C, 68.64; H, 9.01; N, 4.62.

TLC (Silica Gel GF): R$_f$ =0.34 in hexane/ethyl acetate/methanol (40:10:1).

Physical Data For Trans Isomer $^1$HNMR (CDCl$_3$, TMS): 7.14–6.68 (m, 3H); 5.78–5.04 (m, 3H); 3.81 (s, 3H), 3.52–1.54 (m, 13H); 0.95 (t, J=7 Hz, 3H).

IR (mull): v$_{max}$ 1641 and 1588 cm$^{-1}$.

Analysis: Calcd for C$_{17}$H$_{25}$NO.HCl: C, 69.02; H, 8.86; N, 4.74. Found: C, 70.38; H, 8.93; N, 4.12.

EXAMPLE 32

Cis-(±)-1,2,3,4-tetrahydro-8-methoxy-2-(2-propenyl-amino)-1-naphthalenecarboxylic Acid Methyl Ester and trans-(±)-1,2,3,4-tetrahydro-8-methoxy-2-(2-propenylamino)-1-naphthalene-carboxylic Acid Methyl Ester (G-2, Chart G)

To a solution of 18.74 g (0.08 mol) 1,2,3,4-tetrahydro-8-methoxy-2-oxo-1-naphthalenecarboxylic acid, methyl ester and 30 mL (0.4 mol) allylamine in 320 mL MeOH/THF (1:1) was added HOAc (about 50 mL) dropwise at 0–5° C. to adjust the pH to 4–5 under the nitrogen atmosphere. The reaction mixture was stirred for 30 minutes, then 10 g (0.16 mol) of sodium cyanoborohydride was added. The reaction was monitored by TLC analysis. After the reaction mixture was stirred at room temperature for three days, the reaction was quenched with saturated sodium bicarbonate until the pH of the mixture was 8–9 (sodium hydroxide should not be used since methyl ester will be hydrolyzed in the strong base). The solution was extracted with methylene chloride (2×1 L). The combined organic layers were washed with brine, dried (MgSO$_4$), filtered and concentrated in vacuo. The resulting oil was purified by liquid chromatography on 1 kg of silica gel 60 (230–400 m), eluting with hexanethyl acetate (2:1), and collecting 40 mL fractions. Fractions 98–106 gave 4.2 g (19%) of light yellow oil, assigned as the trans isomer, the free base of the trans isomer. Fractions 107–139 gave 14.3 g (65%) of a light yellow oil, assigned as the cis isomer. Both oils were converted into HCl-salt by treatment of excess anhydrous hydrochloric acid/methanol (prepared by mixing acetyl chloride and methanol at 0° C.) and concentrated in vacuo. The cis isomer, the major product, was recrystallized from ethyl acetate/methanol to give a white solid, m.p. 223–225° C. N. The trans isomer, the minor product, was recrystallized from ethyl acetate/hexane to give a white solid, m.p. 170–173° C.

Physical Data For Cis Isomer $^1$HNMR (CDCl$_3$, TMS): 7.25–6.78 (m, 3H); 6.01–5.51 (m, 3H); 3.81 (s, 3H); 3.71 (s, 3H); 4.46–1.82 (m, 9H).

IR (mull): v$_{max}$ 1731, 1604 and 1579 cm$^{-1}$.

Analysis: Calcd for C$_{16}$H$_{21}$NO$_3$.HCl: C, 61.63; H, 7.11; N, 4.49. Found: C, 61.98; H, 7.34; N, 4.73.

Physical Data For Trans Isomer $^1$HNMR (CDCl$_3$, TMS): 7.26–6.85 (m, 3H); 6.01–5.51 (m, 3H); 3.81 (s, 3H); 3.71 (s, 3H); 4.23–2.02 (m, 9H).

IR (mull): v$_{max}$ 1735, 1632, 1592 and 1574 cm$^{-1}$.

Analysis: Calcd for C$_{16}$H$_{21}$NO$_3$.HCl: C, 61.63; H, 7.11; N, 4.49. Found: C, 61.47; H, 7.29; N, 4.56.

EXAMPLE 33

Cis-(±)-1,2,3,4-tetrahydro-8-methoxy-3-(2-propenyl)-N-propyl-2-naphthalenamine Hydrochloride and trans-(+)-1,2,3,4-tetra-hydro-8-methoxy-3-(2-propenyl)-N-propyl-2-naphthalenamine Hydrochloride (F-5, Chart F)

To a solution of 3.0 g (14 mmol) 1,2,3,4-tetrahydro-8-methoxy-2-oxo-3-(2-propenyl)naphthalene and 4.6 mL (56 mmol) n-propylamine in 70 mL MeOH/THF (1:1) was added HOAc (about 11 mL) dropwise at 0–5° C. to adjust the pH to 4–5 under the nitrogen atmosphere. The reaction mixture was stirred for 30 minutes then 1.8 g (28 mmol) of sodium cyanoborohydride was added. The reaction was monitored by TLC analysis. After the reaction mixture was stirred at room temperature for 24 hours, the reaction was quenched with 20% sodium hydroxide until pH>13. The solution was extracted with methylene chloride (2×1 L). The combined organic layers were washed with brine, dried (MgSO$_4$), filtered and concentrated in vacuo. The resulting oil was purified by liquid chromatography on 400 g of silica gel 60 (230–400 m), eluting with 1 L 10%, 2 L 25% acetone/methylene chloride. Fractions 21–70 gave 2.87 g (79%) of the mixture of cis and trans isomers. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (2.24 g) was assigned as pure cis isomer. The mother liquor was free-based by treatment with saturated sodium bicarbonate to pH>8 and extracted with methylene chloride. The resulting oil was purified by liquid chromatography on 400 g silica gel 60 (230–400 m), eluting with methylene chloride-acetone (3:1) and collecting 40 mL fractions. Fractions 24–31 afforded additional 0.14 g of pure 4 k after converting to HCl-salt and recrystallizing from ethyl acetate/-methanol. Thus, 2.38 g of pure cis isomer of the title compound was isolated: m.p. 216–219° C. Fractions 33–72 gave 0.4 g of an oil which gave 0.38 g of pure trans isomer of the title compound as a white solid after converting to HCl-salt and recrystallizing from ethyl acetate/hexane: m.p. 153–155° C.

Physical Data For Cis Isomer $^1$HNMR (CDCl$_3$, TMS): 7.27–6.65 (m, 3H); 5.92–4.95 (m, 3H); 3.78 (s, 3H); 3.54–1.55 (m, 13H); 1.02 (t, J=7 Hz, 3H).

IR (mull): v$_{max}$ 1604 and 1587 cm$^{-1}$.

Analysis: Calcd for C$_{17}$H$_{25}$NO.HCl: C, 69.02; H, 8.86; N, 4.74. Found: C, 68.97; H, 8.91; N, 4.92.

Physical Data For Trans Isomer
$^1$HNMR (CDCl$_3$, TMS): 7.26–6.65 (m, 3H); 5.88–5.06 (m, 3H); 3.78 (s, 3H); 3.38–1.60 (m, 13H); 0.99 (t, J=7 Hz, 3H).

IR (mull): $v_{max}$ 1605 and 1593 cm$^{-1}$.

Analysis: Calcd for C$_{17}$H$_{25}$NO.HCl: C, 69.02; H, 8.86; N, 4.74. Found: C, 63.73; H, 9.12; N, 4.94.

EXAMPLE 34

Cis-(±)-1,2,3,4-tetrahydro-8-methoxy-N,3-di-2-propenyl-2-naphthalenamine Hydrochloride and trans-(±)-1,2,3,4-tetrahydro-8-methoxy-N,3-di-2-propenyl-2-naphthalenamine Hydrochloride (F-5, Chart F)

To a solution of 3.24 g (15 mmol) 1,2,3,4-tetrahydro-8-methoxy-2-oxo-3-(2-propenyl)naphthalene and 4.5 mL (60 mmol) allylamine in 75 mL MeOH/THF (1:1) was added HOAc (about 12 mL) dropwise at 0–5° C. to adjust the pH to 4–5 under the nitrogen atmosphere. The reaction mixture was stirred for 30 minutes, then 1.9 g (30 mmol) of sodium cyanoborohydride was added. The reaction was monitored by TLC analysis. After the reaction mixture was stirred at room temperature for 24 hours, the reaction was quenched with 20% sodium hydroxide until pH>13. The solution was extracted with methylene chloride (2×1 L). The combined organic layers were washed with brine, dried (MgSO$_4$), filtered and concentrated in vacuo. The resulting oil was purified by liquid chromatography on 400 g of silica gel 60 (230–400 m), eluting with 2 L 10%, 1 L 25% methylene chloride/acetone, and collecting 40 mL fractions. Fractions 14–56 gave 3.3 g (86.3%) of the mixture of cis and trans products. The mixture was treated with excess anhydrous hydrochloric acid/methanol (prepared by mixing acetyl chloride and methanol at 0° C.) and concentrated in vacuo. The resulting solid was recrystallized by dissolving in ethyl acetate/methanol, concentrating on the steam bath until the crystal starting to appear and allowing the mixture to stand in the freezer (at −20° C.). The white solid isolated (2.74 g) was assigned as pure cis isomer of the title compound. The mother liquor was freebased by treatment with saturated sodium bicarbonate to pH>8 and extracted with methylene chloride. The resulting oil was purified by liquid chromatography on 400 g silica gel 60 (230–400 m), eluting with methylene chloride-acetone and collecting 40 mL fractions. Fractions 20–22 afforded additional 0.11 g of pure after converting to HCl-salt and recrystallizing from ethyl acetate/methanol. Thus, 2.85 g of pure cis isomer of the title compound was isolated: m.p. 165–167° C. Fractions 23–34 gave 0.48 g of an oil which gave 0.46 g of pure trans isomer of the title compound as a white solid after converting to HCl-salt and recrystallizing from ethyl acetate/hexane: m.p. 123–125° C.

Physical Data For Cis Isomer
$^1$HNMR (CDCl$_3$, TMS): 7.13–6.65 (m, 3H); 6.30–4.95 (m, 6H); 3.78 (s, 3H); 3.96–1.88 (m, 11H).

IR (mull): $v_{max}$ 1640 and 1587 cm$^{-1}$.

Analysis: Calcd for C$_{17}$H$_{23}$NO.HCl: C, 69.49; H, 8.23; N, 4.77. Found: C, 69.75; H, 8.48; N, 4.82.

Physical Data For Trans Isomer
$^1$HNMR (CDCl$_3$, TMS): 7.14–6.64 (m, 3H); 6.22–5.02 (m, 6H); 3.79 (s, 3H); 3.82–1.60 (m, 11H).

IR (mull): $v_{max}$ 1602, 1592 and 1582 cm$^{-1}$.

Analysis: Calcd for C$_{17}$H$_{23}$NO.HCl: C, 69.49; H, 8.23; N, 4.77. Found: C, 69.86; H, 8.43; N, 4.81.

EXAMPLE 35

Cis-(±)-5,6,7,8-tetrahydro-8-(2-propenyl)-7-(2-propenylamino)-1-naphthalenol Hydrochloride and (±)-2,3,3a,4,5,9b-hexahydro-2-methyl-3-(2-propenyl)(1H)benz(e)indol-9-ol Hydrochloride (E-4, Chart E)

A solution of 1.0 mL (6.0 mmol) diphenylphosphine in 12 mL THF in a three-neck, round-bottomed flask, equipped with a condenser and a septum, was treated with 4.4 mL (6.0 mmol) of n-butyllithium (1.6 M in hexane) at 0° C. under a nitrogen atmosphere. The mixture was stirred at room temperature for 10 minutes and 0.77 g (3.0 mmol) of cis-(±)-1,2,3,4-tetrahydro-8-methoxy-N,1-di-(2-propenyl)-2-naphtha-lenamine in 12 mL of THF was added. The red solution was refluxed (bath temperature 70° C.) for 48 hours. The reaction was quenched with water and extracted with ethyl acetate (2×500 mL). The organic layer was washed with brine, dried (MgSO$_4$), filtered and concentrated in vacuo to give a yellow oil. This oil was purified by liquid chromatography on 400 g silica gel 60 (230–400 m), eluting with 1 L 10% and 3 L 33% acetone/hexane, and collecting 40 mL fractions. Fractions 31–50 gave 0.32 g (44%) of free base of trans-(±)-2,3,3a,4,5,9b-hexahydro-2-methyl-(2-propenyl)(1H)(benz(e)indol hydrochloride as a light yellow oil. The oil was treated with excess anhydrous hydrochloric acid/methanol and concentrated in vacuo. Recrystallization from ethyl acetate-methanol afforded pure trans-(±)-2,3,3a,4,5,9b-hexahydro-2-methyl-(2-propenyl)(1H)(benz(e)indol hydrochloride as a white solid, m.p. 257°–258° C. Fractions 68–100 afforded 0.25 g (34%) of free base of the cis title compound as a light yellow oil. This oil was converted into HCl-salt as described above and recrystallized from ethyl acetate-methanol to give pure cis-(±)-5,6,7,8-tetrahydro-8-(2-propenyl)-7-(2-propenyl-amino)-1-naphthalenol hydrochloride, m.p. 190°–191° C.

Physical Data For Trans Isomer
$^1$HNMR (CDCl$_3$, TMS): 7.0–6.6 (m, 3H); 6.13–5.61 (m, 3H); 4.03–1.50 (m, 11H); 1.50, 1.48 (d, 3H).

IR (mull): $v_{max}$ 1606 and 1584 cm$^{-1}$.

Analysis: Calcd for C$_{16}$H$_{21}$NO.HCl: C, 68.68; H, 7.93; N, 5.01. Found: C, 68.64; H, 8.25; N, 5.15.

Physical Data For Cis Isomer
$^1$HNMR (CD$_3$OD,TMS): 7.00–6.00 (m, 3H); 6.03–5.50 (m, 6H); 3.83–1.60 (m, 11H).

IR (mull): $v_{max}$ 3400, 1610 and 1587 cm$^{-1}$.

Analysis: Calcd for C$_{16}$H$_{21}$NO.HCl: C, 68.68; H, 7.93; N, 5.01. Found: C, 68.64; H, 8.07; N, 4.98.

EXAMPLE 36

Cis-(±)-5,6,7,8-tetrahydro-8-(2-propenyl)-7-(propyl-amino)-1-naphthalenol Hydrochloride (E-4, Chart E)

A solution of 2.8 mL (16.0 mmol) diphenylphosphine in 16 mL THF in a three-neck, round-bottomed flask, equipped with a condenser and a septum, was treated with 10 mL (16.0 mmol) of n-butyllithium (1.6 M in hexane) at 0° C. under a nitrogen atmosphere. The mixture was stirred at room temperature for 10 minutes and 1.0 g (4.0 mmol) of cis-(±)-1,2,3,4-tetrahydro-8-methoxy-1-(2-propenyl)-N-propyl-2-naphthalenamine in 16 mL of THF was added. The red solution was refluxed (bath temperature 70° C.) for 48 hours. The reaction was quenched with water and extracted with ethyl acetate (2×500 mL). The organic layer was washed with brine, dried (MgSO$_4$), filtered and concentrated in vacuo to give a yellow oil. This oil was purified by liquid chromatography on 800 g silica gel 60 (230–400 m), eluting with 2 L 10% and 3 L 20% acetone/hexane, and collecting 40 mL fractions. Fractions 88–115 gave 0.85 g (87%) of free base of the title compound as a light oil. The oil was treated with excess anhydrous hydrochloric acid/methanol and concentrated in vacuo. Recrystallization from ethyl acetate-methanol afforded pure title compound as a white solid: m.p. 162–164° C.

$^1$HNMR (CD$_3$OD, TMS): 7.0–6.59 (m, 3H); 6.00–4.90 (m, 3H); 3.73–1.73 (m, 13H); 1.05 (t, J=7 Hz, 3H).

IR (mull): $v_{max}$ 3405, 1610 and 1588 cm$^{-1}$.

Analysis: Calcd for $C_{16}H_{23}NO \cdot HCl$: C, 68.19; H, 8.58; N, 4.97. Found: C, 67.85; H, 8.86; N, 4.87.

EXAMPLE 37
Cis(±)-1,2,3,4-tetrahydro-8-methoxy-1-(2-propenyl)-N-propyl-2-naphthalenyl Acetamide A solution of 3.5 g (13.5 mmol) of the free base of cis(±)-1,2,3,4-tetrahydro-8-methoxy-1-(2-propenyl)-N-propyl-2-naphtha-leneamine, 10 mL of acetic anhydride, 10 mL of pyridine, and 13.5 mL of methylene chloride was stirred at room temperature for four hours. The reaction was quenched with 10 mL of methanol, stirred for 30 minutes, and then quenched with 10 mL water. The mixture was extracted with methylene chloride (2×500 mL). The organic layer was washed with 10% aqueous sodium bisulfate, brine, 1 N sodium hydroxide, dried (MgSO$_4$), filtered, and concentrated in vacuo. The resulting oil was purified by liquid chromatography on 400 g of silica gel 60 (230–400 m), eluting with methylene chloride-acetone (9:1), and collecting 40 mL fractions. Fractions 24–42 gave 3.75 g (92%) of pure title compound as a colorless oil.

$^1$HNMR (CDCl$_3$, TMS): 7.14–6.63 (m, 3H); 5.80–4.83 (m, 3H); 4.06–3.92 (m, 1H); 3.80/3.76 (s, 3H); 3.85–1.24 (m, 11H); 2.14/2.10 (s, 3H); 0.92/0.90 (s, 3H).

IR (mull): $v_{max}$ 1643 and 1586 cm$^{-1}$.

MS: M$^+$ 301, other ions at m/z 260, 218, 200, 185, 169, 159, 145, 126.

Analysis: Calcd for $C_{19}H_{27}NO_2$: C, 75.71; H, 9.03; N, 4.65. Found: C, 75.21; H, 9.30; N, 4.64.

EXAMPLE 38
Cis(±)-1,2,3,4-Tetrahydro-8-methoxy-N,1-di-propyl-2-naphthalenamine Hydrochloride (E-3, Chart E)

A mixture of 2.95 g (10 mmol) cis(±)-1,2,3,4-tetrahydro-8-methoxy-1-(2-propenyl)-N-propyl-2-naphthalenamine, 0.3 g 10% palladium on carbon, and 100 mL methanol was shaken in a Parr hydrogenation apparatus under hydrogen atmosphere at 40 p.s.i. for two hours. TLC analysis showed no starting material remaining. The mixture was filtered through a Celite pad and concentrated in vacuo. The resulting solid was recrystallized from ethyl acetate/methanol to give 2.74 g (92%) of pure title compound as a white solid: m.p. 249°–250° C.

$^1$HNMR (CDCl$_3$, TMS): 7.16–6.73 (m, 3H); 3.68–3.55 (m, 1H); 3.38–1.20 (m, 14H); 1.04/0.93 (t, J=7 Hz, 6H).

IR (mull): $v_{max}$ 1601 and 1584 cm$^{-1}$.

Analysis: Calcd for $C_{17}H_{27}NO \cdot HCl$: C, 68.55; H, 9.48; N, 4.70. Found: C, 68.67; H, 9.50; N, 4.95.

EXAMPLE 39
Cis-(±)-1,2,3,4-Tetrahydro-8-methoxy-1-(2-propenyl)-N,N,-di-propyl)-2-naphthalenamine Hydrochloride (E-3, Chart E)

A round-bottomed flask, equipped with a Dean-Stark moisture trap, was charged with 7.05 g (40.0 mmol) of 8-methoxy-1-(2-propenyl)-2-tetralone, 11 mL (80.0 mmol) of dipropylamine, 76 mg of p-toluene-sulfonic acid monohydrate, and 100 mL of toluene. The mixture was refluxed under a nitrogen atmosphere. After 24 hours, another portion of 11 mL dipropylamine was added and continued refluxing for additional 24 hours. Aliquot was taken, concentrated in vacuo, and examined with $^1$HNMR for the enamine hydrogen peak. The reaction appeared to be 85% completion. The mixture was then concentrated in vacuo. The concentrate was dissolved in 100 mL THF and 13.8 mL (160 mmoL) allylbromide was added and the mixture was refluxed for 48 hours. The solvent was removed in vacuo and $^1$HNMR showed no enamine remaining. This crude product was dissolved in 160 mL 2-propanol/THF (1:1) and 5 mL of acetic acid was added under a nitrogen atmosphere. The mixture was treated with 5.03 g (80 mmol) of sodium cyanoboro-hydride and stirred at room temperature for 48 hours. The reaction was then quenched with 50 mL of water, stirred for 30 minutes, basified with saturated sodium bicarbonate and extracted with methylene chloride (2×600 mL). The organic layer was washed with water, brine, dried (MgSO$_4$), filtered and concentrated in vacuo. This crude product was purified by liquid chromatography on 560 g of silica gel 60 (230–400 m), eluting with 10% ethyl acetate/hexane (0.5% triethylamine), and collecting 40 mL fractions. Fractions 22–53 were combined and concentrated in vacuo. The resulting brown oil was repurified by the same column, but eluting this time with 2 L methylene chloride and 4 L methylene chloride-methanol (20:1), and collecting 40 mL fractions. Fractions 64–155 gave 2.96 g (24.5%) of the desired product as a yellow oil. This oil was treated with excess anhydrous hydrochloric acid/methanol and concentrated in vacuo. Recrystallization from ethyl acetate/methanol afforded 2.14 g of pure title compound as a white solid: m.p. 159°–160° C.

$^1$HNMR (CD$_3$OD, TMS): 7.18–6.74 (m, 3H); 5.78–4.89 (m, 3H); 3.80 (s, 3H); 3.58–1.74 (m, 16H), 1.05 (t, J=7 Hz, 6H). Decoupling experiment showed that the coupling constant of C-1 and C-2 protons is 4.31, indicating the protons are di-equatorial, thus this product is a cis compound.

IR (mull): $v_{max}$ 1640 and 1586 cm$^{-1}$.

Analysis: Calcd for $C_{20}H_{31}NO \cdot HCl$: C, 71.09; H, 9.55; N, 4.15. Found: C, 71.03; H, 9.79; N, 4.23.

EXAMPLE 40
Cis(±)1,2,3,4-tetrahydro-8-methoxy-N,N,1-tripropyl-2-naphthalenamine Hydrochloride A solution of 1.79 g (6.0 mmol) cis(±)-1,2,3,4-tetrahydro-8-methoxy-N,1-di-propyl-2-naphthalenamine hydrochloride (Example 47) 4.2 mL (48 mmol) of propionyl chloride, 9.6 mL of pyridine, and 24 mL of methylene chloride was stirred at room temperature under a nitrogen atmosphere. After 24 hours, TLC analysis showed no starting material remaining. The reaction was quenched with 4 mL of methanol and stirred for one hour. The mixture was then treated with water followed by 20% sodium hydroxide to pH 7–8, and extracted with ethyl acetate. The organic layer was washed with water, 10% sodium bisulfate, saturated sodium bicarbonate, brine, dried (MgSO$_4$), filtered and concentrated in vacuo. The brown oil was purified by liquid chromatography on 560 g of silica gel 60 (230–400 m), eluting with hexane-acetone (9:1), and collecting 40 mL fractions. Fractions 38–70 gave 1.8 g of a yellow oil. This oil was dissolved in 96 mL THF and treated with 0.91 g (24 mmol) of lithium aluminum hydride (Alfa) under a nitrogen atmosphere. The mixture was refluxed for five hours, cooled to room temperature, diluted with 200 mL THF, transferred into an Erlenmeyer flask equipped with a magnetic stirring bar, and added dropwise saturated sodium sulfate to destroy the excess lithium aluminum hydride. After the grey suspension became white, the mixture was diluted with ethyl acetate (800 mL) and dried over anhydrous magnesium sulfate. Filtration and concentration afforded a light yellow oil. This oil was purified by liquid chromatography on 800 g silica gel 60 (230–400 m), eluting with hexane-acetone (9:1), and collecting 40 mL fractions. Fractions 41–48 gave 1.27 g (70%) of a free base of 12 as a near colorless oil. About 0.5 g of this material was converted into hydrochloric acid salt by treating with HCl/methanol, and recrystallized from ethyl acetate/hexane to give pure title compound as a white solid: m.p. 152°–154° C.

¹HNMR (CDCl₃, TMS): 7.15–6.70 (m, 3H); 3.81 (s, 3H); 3.78–1.24 (m, 18H); 1.06/0.99/0.94 (3 t, J=7 Hz, 9H).

IR (mull): $v_{max}$ 1599 and 1588 cm⁻¹.

Analysis: Calcd for C₂₀H₃₃NO.HCl: C, 70.66; H, 10.08; N: 4.12. Found: C, 70.44; H, 10.22; N, 4.32.

EXAMPLE 41

Cis(±)-5,6,7,8-Tetrahydro-8-propyl-7-(propylamino)-1-naphthalenol Hydrochloride (E-4, Chart E)

A solution of 0.57 g (2.0 mmol) methoxy-amine cis(±)-1,2,3,4-tetrahydro-8-methoxy-N,1-di-propyl-2-naphthalenamine hydrochloride in 10 mL 48% hydrobromic acid was refluxed (bath temperature, 120° C.) for eight hours. TLC analysis showed no starting material remaining. The mixture was cooled to room temperature, treated with 20% sodium hydroxide to pH 7–8, and extracted with ethyl acetate. The organic layer was washed with brine, dried (MgSO₄), filtered, and concentrated in vacuo. The oil was converted to HCl-salt with excess anhydrous hydrochloric acid and recrystallized from ethyl acetate to give 0.36 g (64%) of pure title compound as a white solid: m.p. 244°–245° C.

¹HNMR (CD₃OD, TMS): 6.98–6.59 (m, 3H); 3.63–1.36 (m, 14H); 1.05/0.91 (2 t, J =7 Hz, 6H).

IR (mull): $v_{max}$ 3226, 1609 and 1586 cm⁻¹.

Analysis: Calcd for C₁₆H₂₆NO.HCl: C, 67.71; H, 9.23; N, 4.94. Found: C, 67.52; H, 8.82; N, 5.50.

Cis(±)-5,6,7,8-tetrahydro-7-(dipropylamino)-8-propyl-1-naphthalenol Hydrochloride, White Solid: m.p. 237°–239° C.

¹HNMR (CDCl₃, TMS): 7.01–6.61 (m, 3H); 3.82–1.22 (m, 19H); 1.03 (2 t, J=7 Hz, 6H); 0.93 (t, J=7 Hz, 3H).

IR (mull): $v_{max}$ 3400, 1607 and 1591 cm⁻¹.

Analysis: Calcd for C₁₉H₃₁NO: C, 70.02; H, 9.90; N, 4.30. Found: C, 69.99; H, 10.14; N, 4.39.

EXAMPLE 42

Cis-(±)-1,2,3,4-Tetrahydro-8-methoxy-2-(2-propenylamino)-1-Naphthalenemethanol Hydrochloride (G-4, Chart G)

A solution of 4.13 g (15 mmol) of the free base of the amino-ester cis(±)-1,2,3,4-tetrahydro-8-methoxy-2-(2-propenylamino)-1-naphthalenecarboxylic acid methyl ester in 30 mL THF cooled to 0–5° C. under the nitrogen atmosphere was treated with 1.14 g (30 mmol) of lithium aluminum hydride. The mixture was stirred at room temperature for 24 hours. TLC analysis showed no starting material remaining. The mixture was then quenched by dropwise addition of saturated sodium sulfate until the gray suspension became white. To this mixture 20 mL of methanol and 500 mL of THF was added and dried over anhydrous magnesium sulfate by stirring for about one hour. The mixture was filtered through a Celite pad and concentrated in vacuo. The crude product was purified by liquid chromatography on 400 g of silica gel (230–400 m), eluting with 1 L 25% and 2 L 50% acetone/hexane, and collecting 40 mL fractions. Fractions 42–95 afforded 3.22 g (87%) of the desired alcohol. Treatment with excess HCl/MeOH and recrystallization from ethyl acetate/methanol gave 2.24 g of pure title compound as a white solid: m.p. 203°–204° C.

¹HNMR (CDCl₃, TMS) 7.20–6.65 (m, 3H); 6.30–5.38 (m, 3H); 3.84 (s, 3H); 4.12–2.10 (m, 12H).

IR (mull): $v_{max}$ 3320, 1645, 1608 and 1585 cm⁻¹.

Analysis: Calcd for C₁₅H₂₁NO₂.HCl: C, 63.48; H, 7.81; N, 4.94. Found: C, 63.14; H, 7.92; N, 4.95.

Trans(±)-1,2,3,4-tetrahydro-8-methoxy-2-(2-propenyl-amino)-1-naphthalenemethanol Hydrochloride, White Solid: m.p. 161°–162° C.

¹HNMR (CDCl₃, TMS): 7.18–6.62 (m, 3H); 6.24–5.42 (m, 3H); 3.75 (s, 3H); 4.38–1.90 (m, 12H).

IR (mull): $v_{max}$ 3370, 1649, 1603 and 1594 cm⁻¹.

Analysis: Calcd for C₁₅H₂₁NO₂.HCl: C, 63.48; H, 7.81; N, 4.94. Found: C, 63.47; H, 7.92; N, 5.06.

EXAMPLE 43

Cis-(±)-1,2,3,4-tetrahydro-8-methoxy-2-propylamino-1-naphthalenemethanol Hydrochloride The mixture of 0.99 g (4.0 mmol) of cis-(±)-1,2,3,4-tetrahydro-8-methoxy-2-(2-propenylamino)-1-naphthalenemethanol hydrochloride, 0.5 g 10% Palladium on carbon, and 80 mL of 95% ethanol was shaken in a Parr shaker apparatus under 50 p.s.i. of hydrogen atmosphere. After 18 hours, the mixture was filtered through a Celite pad, concentrated in vacuo. The resulting oil was treated with excess HCl/MeOH and recrystallized from ethyl acetate/methanol to give pure title compound as a white solid: m.p. 233°–234° C.

¹HNMR (CDCl₃, TMS): 7.17–6.67 (m, 3H); 3.83 (s, 3H); 4.14–1.90 (m, 14H); 1.05 (t, J=7 Hz, 3H).

IR (mull): $v_{max}$ 3308, 1602, 1585 and 1561 cm⁻¹.

Analysis: Calcd for C₁₅H₂₃NO₂.HCl: C, 63.04; H, 8.47; N, 4.90. Found: C, 63.05; H, 8.54; N, 4.90.

EXAMPLE 44

(±)-1,2,3,4-Tetrahydro-8-methoxy-1-methylene-2-(2-propenyl 2-propylamino)-naphthalene Hydrochloride 1,2,3,4-Tetrahydro-8-methoxy-1-hydroxymethyl-2-(2-propenyl)-N-propyl naphthaleneamine was dissolved in a solution containing 2 mL pyridine and 4 mL methylene chloride, treated with 0.76 g (4 mmol) of p-toluenesulfonyl chloride, and the mixture was stirred for 24 hours. The mixture was quenched with 2 mL saturated sodium bicarbonate, followed by 2 mL methanol. After stirring the mixture for one hour, the solution was extracted with methylene chloride (2×300 mL). The organic layer was washed with water, saturated sodium bicarbonate, brine, dried (MgSO₄), filtered and concentrated to give a brown oil. This oil was purified by liquid chromatography on 400 g silica gel 60 (230–400 m), eluting with hexane-acetone (4:1), and collecting 40 mL fractions. Fractions 15–22 afforded 0.53 g of a light yellow oil, which was consistent with the structure of the tosylate by 1HNMR. This oil was then dissolved in 4 mL THF, treated with 2 mL (2 mmol) of potassium-t-butoxide (1 M in THF), and refluxed for two hours. The mixture was quenched with brine and extracted with methylene chloride (2×300 mL). The organic layer was washed with brine, dried (MgSO₄), filtered, and concentrated in vacuo. The concentrate was purified by liquid chromatography on 400 g of silica gel 60 (230 400 m), eluting with hexane-acetone (9:1), and collecting 40 mL fractions. Fractions 13–18 afforded 0.11 g of a light yellow oil which was converted into HCl-salt by treating with excess HCl/methanol. Recrystallization from ethyl acetate/hexane gave pure title compound as an off-white solid: m.p. 131°–133° C.

¹HNMR (CDCl₃, TMS): 7.28–6.78 (m, 3H); 6.18–5.92 (q, 2H); 6.60–5.24 (m, 3H); 4.50 (t, 1H); 3.84 (s, 3H); 3.83–1.55 (m, 10H); 0.91/–0.80 (t, 3H).

IR (mull): $v_{max}$ 1630, 1600 and 1580 cm⁻¹.

EXAMPLE 45

(+)-8-trifluoromethyl-2N-n-propylaminotetralin (H-9, Chart H)

The diastereomer of 8-trifluoromethyl-2N-[(R)-alpha-methylbenzyl-2N-n-propylaminotetralin which originated as the lower Rf compound in the reductive amination (vide supra) (8 g) was dissolved in ethanol (25 ml) and 2 N aq.

HCl. 10% palladium on carbon (4 g) was added and the slurry was hydrogenated in a Parr shaker at 50 p.s.i for 48 hr. The slurry was filtered through diatomaceous earth and the solvent removed under vacuum. The residue was partitioned between ether and 10% aq. sodium carbonate. The ether layer was washed with water and brine. After drying the solution over anhydrous sodium sulfate the solvent was removed under vacuum to afford 5.6 g of a clear liquid. The HCl salt (methanol/ether) gave a m.p. of 282° C.

EXAMPLE 46
(−)-8-trifluoromethyl-2N-n-propylaminotetralin (H-9, Chart H)

The diastereomer of 8-trifluoromethyl-2N-[(R)-alpha-methylbenzyl-2N-n-propylaminotetralin which originated as the higher Rf compound in the reductive amination (vide supra) was subjected to the hydrogenolysis procedure described above. The HCl salt (methanol/ether) gave a m.p. of 282° C.

EXAMPLE 47
(+)-8-trifluoromethyl-2-N,N-di-n-proplyamonotetralin (H-10, Chart H)

(+)-8-Trifluoromethyl-2N-n-propylaminotetralin (2 g), sodium carbonate (2.5 g), n-bromopropane (2.1 ml) and acetonitrile (18 ml) were heated to reflux for 16 hr. The solution was cooled and partitioned between ether and aq. sodium carbonate. The organic layer was washed with water and brine, then dried over sodium sulfate and the solvent removed under vacuum. The residual oil was converted into the fumarate salt (methanol/ether), m.p. 167° C., and an $[alpha]^{25}{}_D$=+30.74° (c=3.10, methanol).

EXAMPLE 48
(−)-8-trifluoromethyl-2-N,N-di-n-propylaminotetralin (H-10, Chart H)

(−)-8-Trifluoromethyl-2N-n-propylamino tetralin was substituted as in the alkylation reaction described above. The fumarate salt (methanol/ether) gave a m.p. of 167° C., and an $[alpha]^{25}{}_D$=−31.4° (c=2.67, methanol).

EXAMPLE 49
8-Bromo-2-N,N-di-n-propylaminotetralin (I-2, Chart I)

8-Bromo-2-tetralone (25 g), methanol (110 mL), tetrahydrofuran (110 mL), and n-dipropylamine (124 mL) were combined and cooled to 0° C. Glacial acetic acid (96 mL) was added. After 10 min sodium cyanoborohydride (15.5 g) was added and stirred at room temp for 18 hr. The solvents were removed under vacuum and ether added. The solution was extracted with aq. sodium carbonate. The ether layer was acidified with 2N HCl. The aqueous layer was extracted with ether from which starting material was isolated. The aqueous layer was made alkaline with 15% sodium hydroxide and extracted with ether. The ether layer was extracted with brine, dried over anhydrous sodium sulfate, and the solvent was removed under vacuum to give 11 g of a yellow liquid.

EXAMPLE 50
8-formyl-2-N,N-di-n-propylaminotetralin (I-3, Chart I)

8-Bromo-2-N,N-di-n-propylaminotetralin (7.6 g) in tetrahydrofuran (50 mL) was cooled to −75° C. t-Butyllithium (1.7 M in pentane, 32 mL) was added, followed after 15 min with dimethylformamide (9.5 mL). The solution warmed to room temp. Ether was added; the solution was extracted with water then with brine. It was dried over anhydrous sodium sulfate and the solvent removed under vacuum to give 1.6 g of a yellow liquid.

EXAMPLE 51
8-(5-oxazolyl)-2-N,N-di-n-propylaminotetralin (I-4, Chart I)

8-Formyl-2-N,N-di-n-propylaminotetralin (2 g), tosylmethyl isocyanide (1.5 g), methanol (15 mL), and potassium carbonate (2 g) were refluxed 2.75 hr. The methanol was removed under vacuum and ether was added. The solution was extracted with water, then with brine. It was dried over anhydrous sodium sulfate and the solvent removed under vacuum. Chromatography was done using a 2×30 cm flash silica gel column eluted with 25% ethylacetate in hexane. The HCL salt (2.3:1 ether:acetonitrile) gave a m.p. of 160° C.

EXAMPLE 52
8-Aminosulfonyl-2N-n-propylaminotetralin

8-Aminosulfonyl-2-tetralone (1.13 g, 5.0 mmol) was dissolved in a mixture of tetrahydrofuran (10 mls) and methanol (25 mls). Acetic acid (3.0 g, 50 mmol) and then n-propylamine (1.5 g, 25 mmol) were added. The mixture was stirred at room temperature for 45 minutes, and sodium cyanoborohydride (0.63 g, 10 mmol) was added. The mixture was stirred at room temperature for 18 hours, and the solvent was removed under vacuum. The residue was partitioned between 2:1 diethylether/tetrahydrofuran and dilute ammonium hydroxide (pH 9–10). The ether solution was again washed with dilute ammonium hydroxide, and the aqueous washings were back extracted 3 times with 2:1 diethylether/tetrahydrofuran. The combined organics were dried ($MgSO_4$), and the solvent was removed under vacuum to leave an amber oil (1.38 g). The compound was dissolved in a small amount of tetrahydrofuran and excess ethereal HCl was added. Diethylether was added, and the precipitate was centrifuged, washed with diethylether, and crystallized from methanol/diethylether to give the amine as an off-white solid (1.29 g, m.p. 257.5–258° C.).

EXAMPLE 53
8-Aminosulfonyl-2-(N-Allyl)tetralin

The compound was prepared in a similar manner to the preparation of the n-propylamine using 8-aminosulfonyl-2-tetralone (1.13 g, 5.0 mmol), allylamine (1.45 g, 25 mmol), acetic acid (3.0 g, 50 mmol), sodium cyanoborohydride (0.63 g, 10 mmol) in tetrahydrofuran (10 mls) and methanol (25 mls). The allylamine hydrochloride was obtained as a tan solid from methanol/diethylether (0.72 g, m.p. 268–268.5° C.).

EXAMPLE 54
8-Aminosulfonyl-2-(N,N-Dipropylamino)tetralin (J-7, Chart J)

A mixture of 8-aminosulfonyl-2-tetralone (1.13 g, 5.0 mmol), dipropylamine (2.6 g, 25 mmol), and p-toluenesulfonic acid monohydrate (0.10 g, 0.53 mmol) in benzene (30 mls) was refluxed through a Dean-Stark trap for 19 hours. Ethanol (30 mls) and platinum oxide (0.30 g) were added, and the mixture was hydrogenated in a Parr apparatus (50 psi) for 5 hours. The mixture was filtered, the catalyst was washed well with ethanol, and the combined filtrate was evaporated under vacuum. The dissolved in 2:1 diethylether/tetrahydrofuran and washed twice with dilute ammonium hydroxide (pH 9–10). The aqueous washings were back extracted with 2:1 diethylether/tetrahydrofuran, and the combined extracts were washed with brine and dried ($MgSO_4$). The solvent was removed under vacuum to leave a brown oil (1.58 g). The compound (1.30 g) was combined with p-toluenesulfonic acid (0.80 g) and the mixture was crystallized from methanol/diethylether to give the dipropylamine as a yellow solid (1.50 g, m.p. 192–194, 225–226° C.).

EXAMPLE 55

8-Aminosulfonyl-2-(N-(3-Phenylpropyl)amino)tetralin

The compound was prepared in a manner similar to the preparation of the dipropylamine above using 8-aminosulfonyl-2-tetralone (1.13 g, 5.0 mmol), 3-phenyl-1-propylamine (0.75 ml, 5.3 mmol), p-toluenesulfonic acid (0.10 g, 0.53 mmol), and platinum oxide (0.30 g) in benzene (20 mls) and ethanol (35 mls) to give a solid (1.71 g). The compound was crystallized from acetonitrile and converted to the hydrochloride salt as above. (m.p. 105–130° C.).

EXAMPLE 56

8-Thiocarboxamido-2-N,N-di-n-propylaminotetralin

8-Bromo-2-N,N,-di-n-propylaminotetralin (620, mg) is dissolved in THF and cooled to −78° C. t-Butyllithium (2 eg.) is added and the solution is stirred for five minutes. Trimethylsilylisothiocyanate (300 mg) is added and the solution is allowed to warm to 0° C. Water and ether are added and the reaction is extracted. The organic layer is washed with brine and dried over anhydrous sodium sulfate. Solvent removal under vacuum affords the title compound.

EXAMPLE 57

Octahydro-1-(1,2,3,4-tetrahydro-8-methoxy-2-naphthalenyl)-azocine Hydrochloride (C-2, Chart C)

To a solution of 1.76 g (10 mmol) 8-methoxy tetralone and 5.66 g (50 mmol) heptamethylenamine in 30 mL MeOH/THF (1:1) was added HOAc dropwise to adjust the pH to 4–5. The reaction mixture stirred for 15 minutes under $N_2$, then 1.26 g (20 mmol) $NaCNBH_3$ was added. When the reaction was complete by TLC (24 h), 1 N NaOH (25 mL) and $H_2O$ (200 mL) was added to quench the reaction. The solution was extracted with $CH_2Cl_2$ (2×500 mL) and the combined organic layers were washed with brine, dried ($MgSO_4$), filtered and concentrated in vacuo. The resulting was purified by liquid chromatography on 400 g of silica gel 60 (230–400 m), eluting with hexane/acetone (5:1). Fractions homogeneous by TLC were combined and concentrated in vacuo to give pure compound as an oil. The HCl salt was formed by using a MeOH/HCl solution. The title compound was recovered as a white solid by recrystallization using EtOAc/MeOH (2.65 g, 86%): mp. 211–213° C.

$^1$HNMR ($CDCl_3$, TMS): 7.13(t, 1H); 6.69 (t, 2H); 3.81 (s, 3H); 3.54 (m, 3H), 3.31–3.18 (m, 3H); 2.94–2.67 (m, 4H); 2.17 (m, 2H); 2.1–1.46 (m, 8H).

IR (mull): $v_{max}$ 2529, 2503, 1585, 1470, 1463, 1453, 1251 $cm^{-1}$.

Analysis: Calcd for $C_{18}H_{27}NO.HCl$: C, 69.769; H, 9.108; N, 4.521. Found: C, 69.6; H, 9.24; N, 4.65.

Utilizing a procedure similar to that of Example 1 but substituting the appropriate starting materials there is obtained Hexahydro-1-(1,2,3,4-tetrahydro-8-methoxy-2-naphthalenyl)-1H-azepine Hydrochloride White Solid: m.p. 236°–237° C.

$^1$HNMR ($CDCl_3$, TMS): 7.12–7.04 (t, 1H); 6.71–6.64 (q, 2H); 3.81 (s, 3H); 3.03–2.76 (m, 7H); 2.45 (q, 1H); 2.0 (m, 1H); 1.62 (m, 10H).

IR (mull): $v_{max}$ 3000, 2600, 2550, 1590, 1480 $cm^{-1}$.

Analysis: Calcd for $C_{17}H_{25}NO.HCl$: C, 69.017; H, 8.859; N, 4.735. Found: C, 68.91; H, 9.04; N, 4.67.

Hexahydro-1-(1,2,3,4-tetrahydro-2-naphthalenyl)-1H-Azepine Hydrochloride as a White Solid: m.p. 243–245° C.-Compound 57-3

EXAMPLE 58

(1-Hexahydroazepinyl)-5,6,7,8-tetrahydronaphthalene-1-carboxamide (L-5, Chart L)-Compound 58-1

Gaseous ammonia was bubbled through a solution of 7-(1-Hexahydroazepinyl)-5,6,7,8-tetrahydronaphthalene-1-arboxylic acid and 2.25 mL Triethylamine in 30 mL DMF. After 10 min, 1.75 mL diethylcyanophosphonate was added and the solution was stirred overnight with ammonia bubbling through the solution. Direct spot TLC showed no starting material remaining. The reaction mixture was evaporated and dissolved in 10 mL methanol. This mixture was flash chromatographed on 200 g silica gel eluting with chloroform first, followed by chloroform/4M $NH_3$ in methanol (95:5). Homogenous samples were combined and concentrated to yield 1 g of a solid. Crystallized from acetone. (Mpt.=141° C.)

EXAMPLE 59

(+)-1,2,3,4-tetrahydro-2-pyrrolidino-8-bromo-tetralin (C-3, Chart C)-Compound 59-1

8-Bromo-2-tetralone (40 g., 177 mmol) and pyrrolidine (3 eq) were dissolved in methanol (350 mL) with bromocresol green as an indicator. Hydrochloric acid (3 eq) in methanol was added. Pyrrolidine (2 eq) was added and the solution stirred at 0° C. for 30 minutes. Sodium cyanoborohydride (2 eq) was added and the solution stirred for another hour at 0° C. It was stirred at room temp for an hour then the solvents were removed under vacuum. Ether was added and sodium carbonate (sat'd, aq). The ether layer was washed with brine, dried over sodium sulfate, and stripped of solvent under vacuum. After chromatography, the yield of pure oil was 29 g, 58.5%. The racemate (21.6 g) and D-tartaric acid (1 eq) were dissolved in acetonitrile (1800 mL) and methanol (50 mL). The resulting white solid was recrystallized from acetonitrile until a constant optical rotation was achieved for the salt, $[\alpha]_D^{25}=+34.07°$, 165.0–166.5° C. mp. Yield of the title compound as an oil was 2 g, $[\alpha]^{25}=+61.27°$.

EXAMPLE 60

(+)-1,2,3,4-tetrahydro-2-pyrrolidino-naphthalene-8-yl-caboxamide (C-4, Chart C)-Compound 60-1

(+)-8-Bromo-2-pyrrolidinotetralin (1.84 g, 6.57 mmol) was dissolved in tetrahydrofuran (13 mL) and cooled to −78° C. t-Butyllithium (1.7 M in hexane, 2.1 eq) was added. After 10 min, trimethylsilylisocyanate (2.5 eq) was added. After 10 min, the bath was removed and the solution allowed to warm to room temp. Sodium carbonate (sat'd, aq) was added and the product extracted with ether/chloroform. The organic layer was washed with water, brine, and then was dried over sodium sulfate. It was stripped of solvent under vacuum to yield white solid. Recrystallization from acetonitrile gave 0.63 g (39.3%) of the hydrochloride of the title compound as white needles, 220.0–224.0° C., $[\alpha]^{25}=+90.62°$ (2 28.5–230.5°$_D$ C. mp for the hydrochloride salt).

Utilizing a procedure similar to that of Example 60, but substituting the appropriate bromotetralin there is obtained (−)-1,2,3,4-tetrahydro-2-pyrrolidino-naphthalene-8-yl-carboxamide (mp 228.5–230.5° C.)

(+)-1,2,3,4-tetrahydro-2-(1-piperidinyl)-naphthalene-8-yl-carboxamide (mp 229° C.)

(−)-1,2,3,4-tetrahydro-2-(1-piperidinyl)-naphthalene-8-yl-caboxamide (mp 229° C.).

The compound (+)1,2,3,4-tetrahydro-2-(1-pyrrolidinyl) naphthalene-8-yl-carboxamide and its salts, processes for preparing said compounds and methods of employing said compounds in therapy represent the best mode of carrying out the invention.

FORMULA
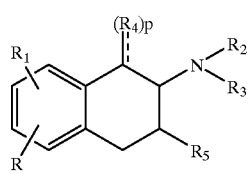
CHART A
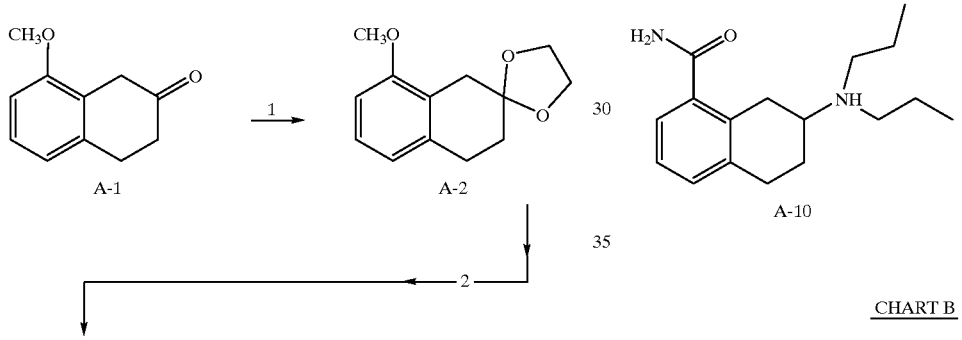
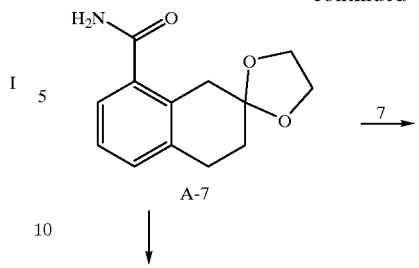
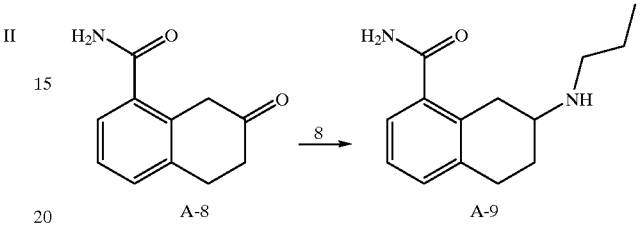
CHART B
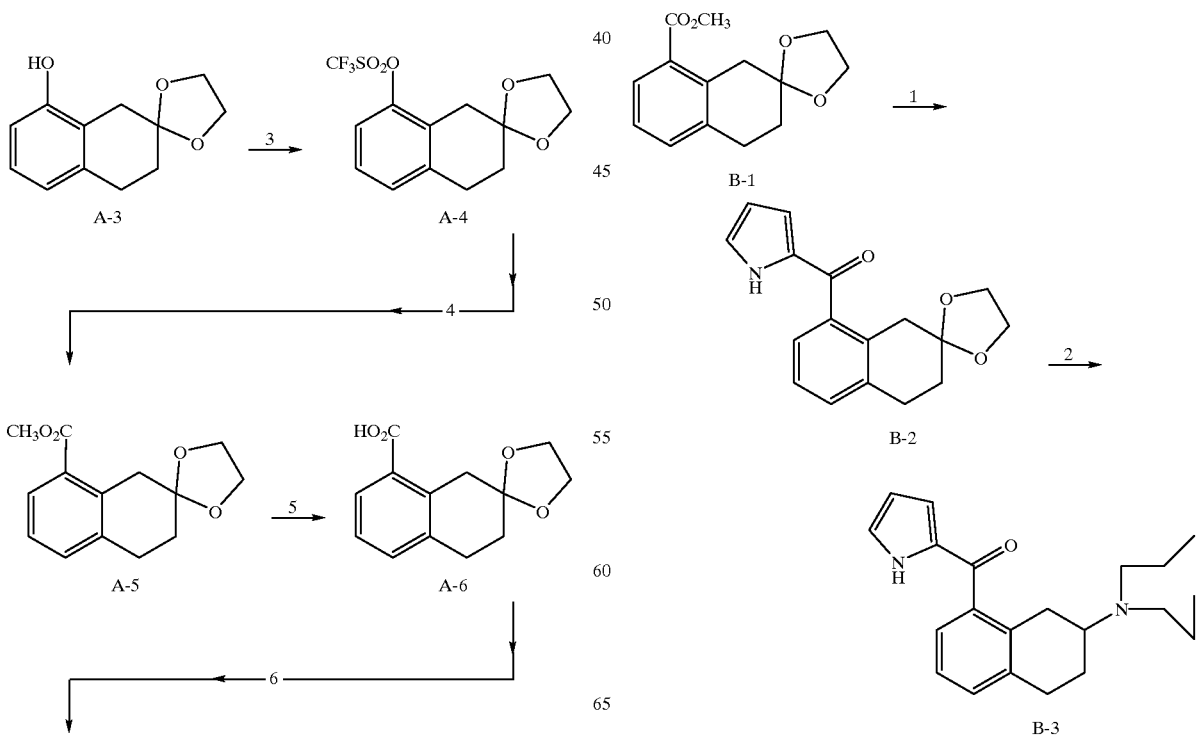

CHART C
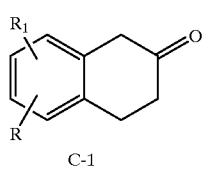
C-1
↓ 1
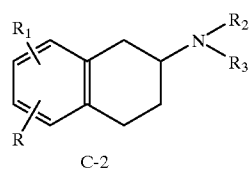
C-2
↓ 2
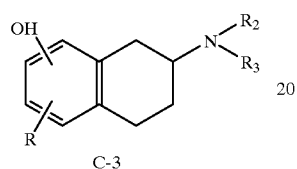
C-3
CHART D
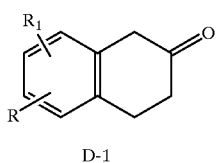
D-1
↓ 1
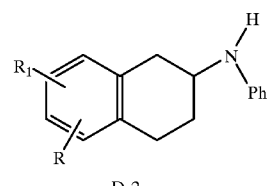
D-2
↓ 2
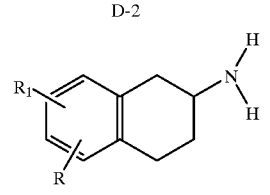
D-3
↓ 3
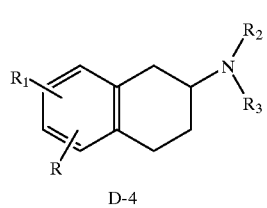
D-4
CHART E
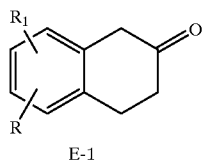
E-1
↓ 1
-continued
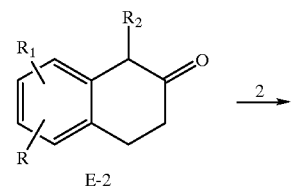
E-2
↓ 2
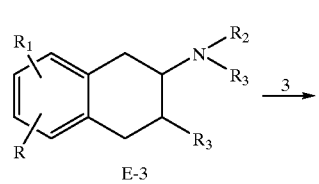
E-3
↓ 3
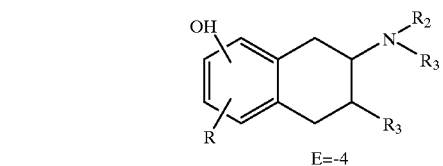
E-4
CHART F
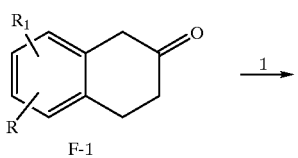
F-1
↓ 1
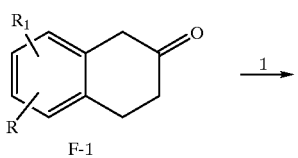
F-2
↓ 2
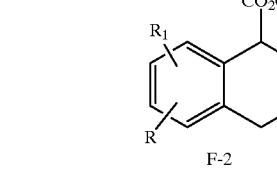
F-3
↓ 3
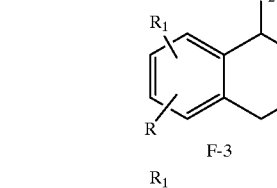
F-4
↓ 4
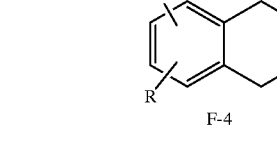
F-5
↓ 5
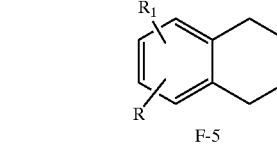
F-6

CHART G
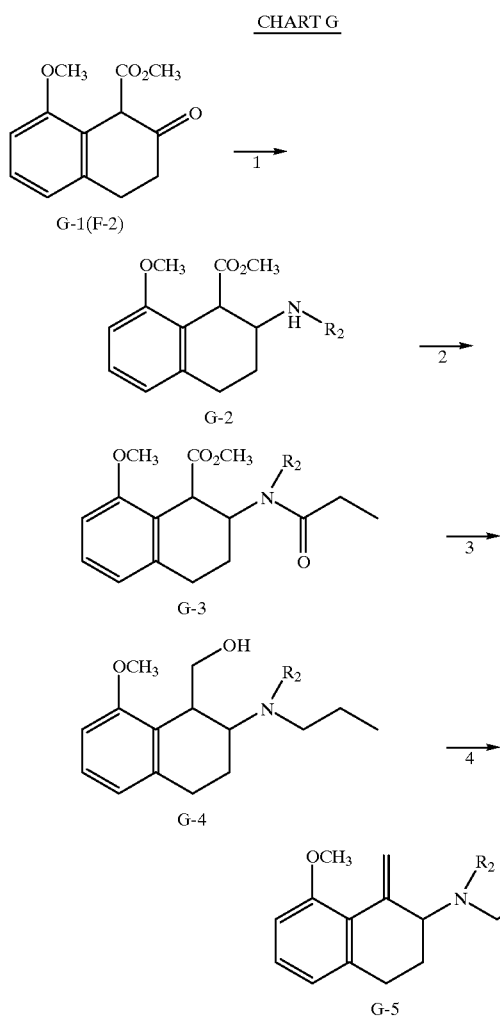
CHART H
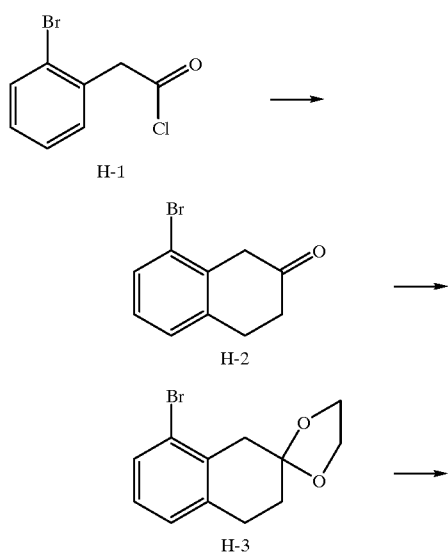
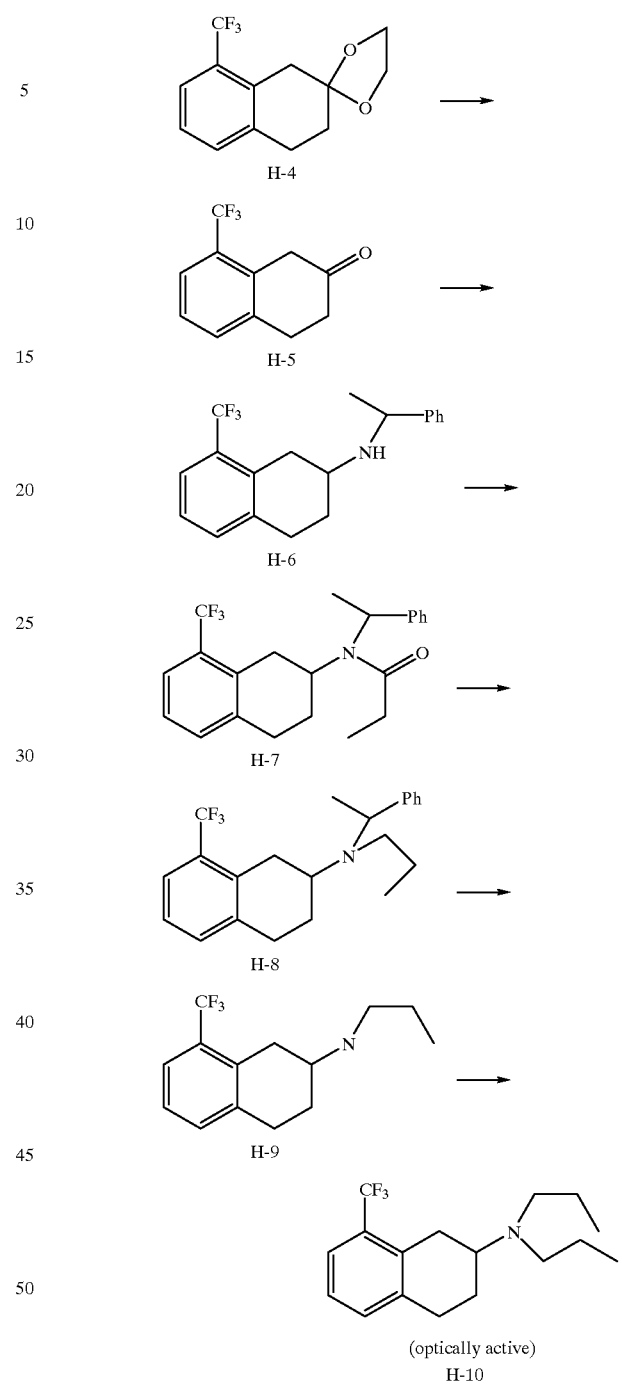

-continued
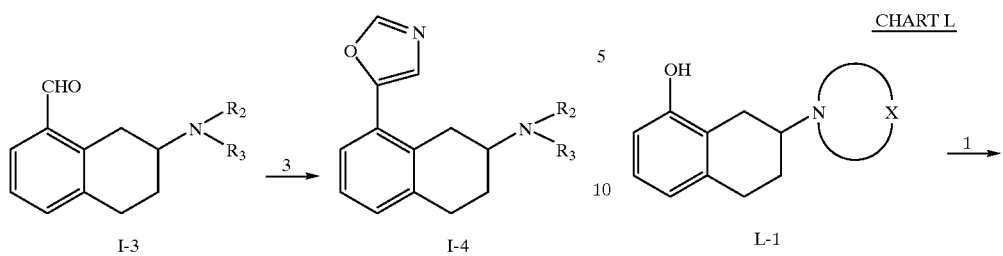
CHART J
CHART J
CHART K
CHART L
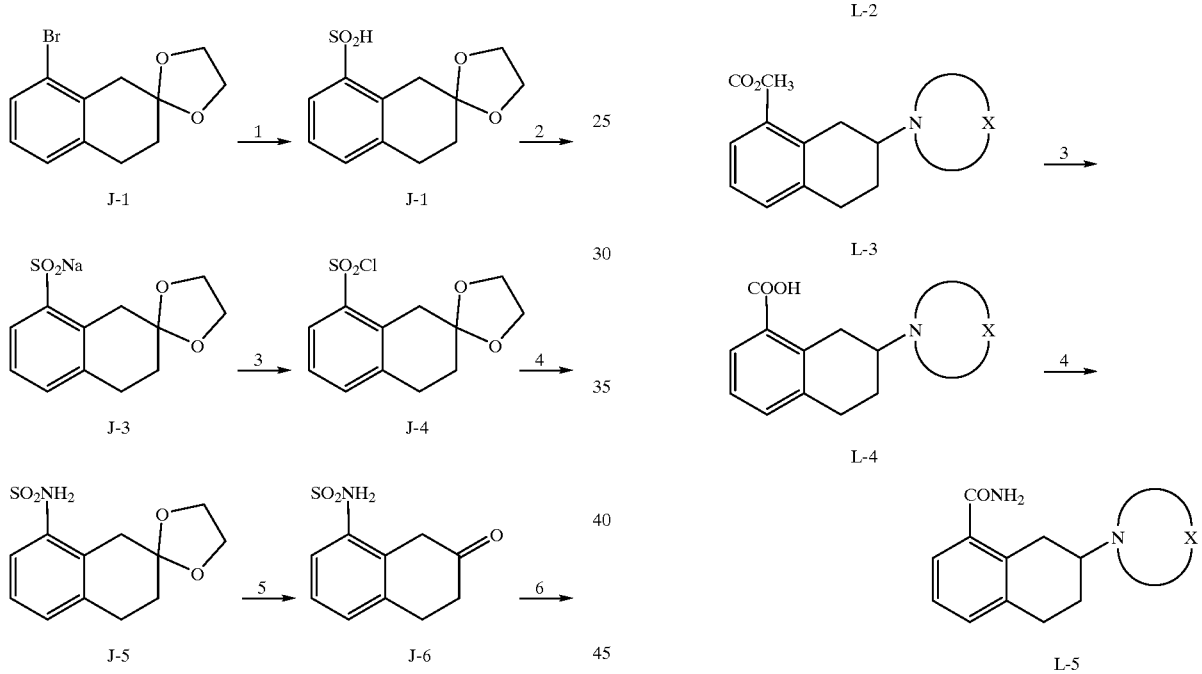
CHART M
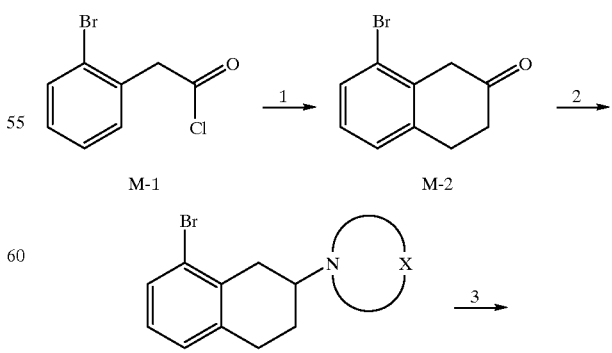

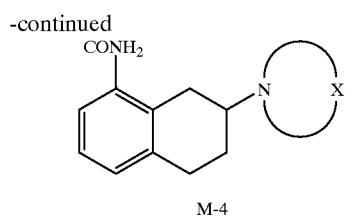

M-4

CHART N

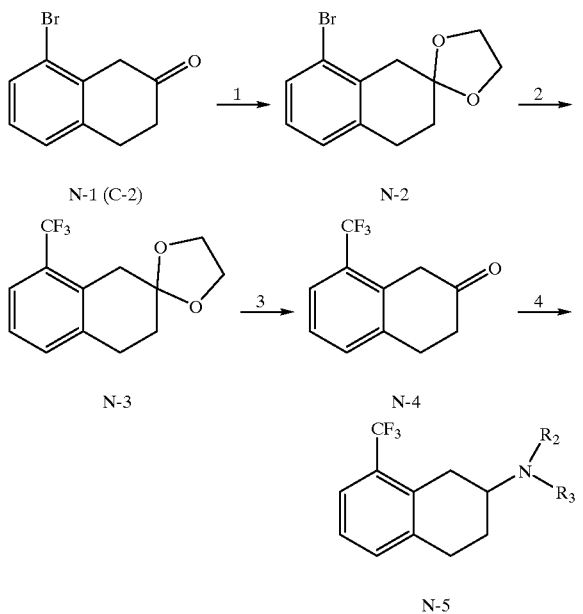

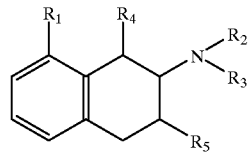

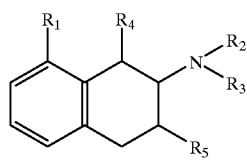

What is claimed is:
1. A compound having the formula

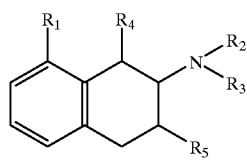

wherein,
R$_1$ is from the group —(CO)het and het wherein het is a five atom heterocyclic aromatic ring containing nitrogen, carbon, or optionally containing an additional heteroatom oxygen;
R$_2$ and R$_3$ is independently selected from
  (a) hydrogen
  (b) C$_{1-8}$ alkyl
  (c) C$_{2-8}$ alkenyl
  (d) C$_{2-8}$ alkynyl
  (e) (CH$_2$)$_m$—C$_{3-8}$ cycloalkyl
  (f) (CH$_2$)$_m$—C$_{3-8}$cycloalkenyl
  (g) (C$_2$)$_m$-aryl
  (h) trimethylsilylmethyl
  (i) allyl
R$_4$ and R$_5$ are independently
  (a) hydrogen
  (b) C$_{1-8}$ alkyl
  (c) C$_{2-8}$ alkenyl
  (d) C$_{2-8}$ alkynyl
  (e) (CH$_2$)$_m$—C$_{3-8}$cycloalkyl
  (f) (CH$_2$)$_m$—C$_{3-8}$cycloalkenyl
  (g) (CH$_2$)$_m$-aryl
  (h) (CH$_2$)$_m$—CO$_2$R$_6$
  (i) (CH$_2$)$_m$—OR$_6$
wherein,
  R$_6$ is hydrogen, C$_{1-4}$ alkyl or aryl,
  m is 0–4,
or a pharmaceutically acceptable addition salt thereof.

2. A compound of claim 1 having the formula

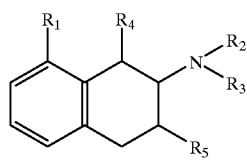

wherein,
R$_1$ is a five atom heterocyclic aromatic ring containing nitrogen, carbon, or optionally containing an additional heteroatom oxygen,
R$_2$ and R$_3$ is independently selected from
  (a) hydrogen
  (b) C$_{1-8}$ alkyl
  (c) C$_{2-8}$ alkenyl
  (d) C$_{2-8}$ alkynyl
  (e) (CH$_2$)$_m$—C$_{3-8}$ cycloalkyl
  (f) (CH$_2$)$_m$—C$_{3-8}$cycloalkenyl
  (g) (CH$_2$)$_m$-aryl
  (h) trimethylsilylmethyl
  (i) allyl
R$_4$ and R$_5$ are independently
  (a) hydrogen
  (b) C$_{1-8}$ alkyl
  (c) C$_{2-8}$ alkenyl
  (d) C$_{2-8}$ alkynyl
  (e) (CH$_2$)$_m$—C$_{3-8}$cycloalkyl
  (f) (CH$_2$)$_m$—C$_{3-8}$cycloalkenyl
  (g) (CH$_2$)$_m$-aryl
  (h) (CH$_2$)$_m$—CO$_2$R$_6$
  (i) (CH$_2$)$_m$—OR$_6$
wherein,
  R$_6$ is hydrogen, C$_{1-4}$ alkyl or aryl,
or a pharmaceutically acceptable addition salt thereof.

3. A compound according to claim 1 wherein R is hydrogen, R$_1$ is 5-oxazolyl; R$_2$ and R$_3$ may be the same or different and are selected from the group of hydrogen and (C$_1$–C$_8$)alkyl.

4. A compound according to claim 1 and selected from the group consisting of
  8-(Oxazol-5-yl)-1,2,3,4-tetrahydro-2,N,N-di-n-propylaminonaphthalene and the hydrochloride thereof,
  8-(3-Bromo-isoxazol-5-yl-1,2,3,4,-tetrahydro-2-N,N-di-n-propylaminonaphthalene and the hydrochloride thereof.

5. A compound according to claim 1 which is,
(1,2,3,4-tetrahydro-2-N,N-dicyclopropylmethylaminonaphthalene-8-yl)(2-pyrrole)-ketone.

6. A compound according to claim 1, 8-(oxazol-5-yl)-1,2,3,4-tetrahydro-2,N,N-di-n-propylaminonaphthalene and the hydrochloride thereof.

* * * * *